US007678560B2

(12) United States Patent
Damude et al.

(10) Patent No.: US 7,678,560 B2
(45) Date of Patent: Mar. 16, 2010

(54) Δ 5 DESATURASE AND ITS USE IN MAKING POLYUNSATURATED FATTY ACIDS

(75) Inventors: Howard Glenn Damude, Hockessin, DE (US); Dana M. Walters Pollak, Media, PA (US); Zhixiong Xue, Chadds Ford, PA (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 421 days.

(21) Appl. No.: 11/748,629

(22) Filed: May 15, 2007

(65) Prior Publication Data

US 2007/0292924 A1 Dec. 20, 2007

Related U.S. Application Data

(60) Provisional application No. 60/801,172, filed on May 17, 2006.

(51) Int. Cl.
*C12N 1/00* (2006.01)
*C12N 15/74* (2006.01)
*C07H 21/04* (2006.01)
(52) U.S. Cl. .................. 435/254.11; 435/471; 536/23.2
(58) Field of Classification Search ........................ None
See application file for complete search history.

(56) References Cited

U.S. PATENT DOCUMENTS

| 5,972,664 | A | 10/1999 | Knutzon et al. |
| 6,075,183 | A | 6/2000 | Knutzon et al. |
| 7,125,672 | B2 | 10/2006 | Picataggio et al. |
| 7,189,559 | B2 | 3/2007 | Damude et al. |
| 7,192,762 | B2 | 3/2007 | Maccol et al. |
| 7,198,937 | B2 | 4/2007 | Xue et al. |
| 7,202,356 | B2 | 4/2007 | Pollak et al. |
| 2006/0168687 | A1 | 7/2006 | Renz et al. |
| 2006/0246556 | A1* | 11/2006 | Napier et al. ............... 435/128 |

FOREIGN PATENT DOCUMENTS

| WO | 2004076617 A2 | 9/2004 |
| WO | WO 2006/012325 A1 | 2/2006 |
| WO | WO 2006/012326 A1 | 2/2006 |

OTHER PUBLICATIONS

Renz, A. et al., Database EBI Accession No. ADR49327 and abstract WO2004/076617, *Phaeodactylum tricornutum* delta-5 desaturase, Dec. 2, 2004, BASF Plant Sci GmbH.
Domergue, F. et al., Database EBI Accession No. Q8RXB1, Delta 5 fatty acid desaturase D5, Jun. 1, 2002, European Journal of Biochemistry.
Domergue, Frederic et al., Cloning and functional characterization of *Phaeodactylum tricornutum* front-end desaturases involved in eicosapentaenoic acid biosynthesis, European Journal of Biochemistry, 2002, pp. 4105-4113, vol. 269, FEBS 2002.
Meyer, Astrid et al., Biosynthesis of Docosahexaenoic Acid in *Euglena gracilis*: Biochemical and Molecular Evidence for the Involvement of a Delta-4-Fatty Acyl Group Desaturase, 2003, pp. 9779-9788, vol. 42, American Chemical Society.
Wallis, James G. et al., The Delta-8-Desaturase of *Euglena gracilia*: An Alternate Pathway for Synthesis of 20-Carbon Polyunsaturated Fatty Acids, Archives of Biochemistry and Biophysics, 1999, pp. 307-316, vol. 365, No. 2, Academic Press.
International Search Report, International Application No. PCT/US2007/011776, International Filing Date: May 16, 2007, Date of International Search Report: Jan. 31, 2008.
J. Dyerberg et al., Fatty Acid Composition of the Plasma Lipids in Greenland Eskimos, Amer. J. Clin. Nutr., 1975, vol. 28:958-966.
J. Dyerberg et al., Eicosapentaenoic Acid and Prevention of Thrombosis and Atherosclerosis?, Lancet., 1978, vol. 2:117-119.
H. Shimokawa, Beneficial Effects of Eicosapentaenoic Acid on Endothelial Vasodilator Functions in Animals and Humans, World Rev. Nutr. Diet, 2001, vol. 88:100-108.
C. Von Schacky et al., 3 Fatty Acids From Eskimos to Clinical Cardiology—What Took Us So Long?, World Rev. Nutr. Diet, 2001, vol. 88:90-99.
National Center for Biotechnology Information General Identifier No. 6842049, Jun. 21, 2000, H.P. Cho et al., Cloning, Expression, and Fatty Acid Regulation of the Human Delta-5 Desaturase, Accession No. AF199596.
National Center for Biotechnology Information General Identifier No. 7861969, May 17, 2000, A.E. Leonard et al., CDNA Cloning and Characterization of Human Delta5-Desaturase Involved in the Biosynthesis of Arachidonic Acid, Accession No. AF22673.
National Center for Biotechnology Information General Identifier No. 11386008, Aug. 31, 2001, R. Zolfaghari et al., Fatty Acid Delta-5 Desaturase MRNA is Regulated by Dietary Vitamin A and Exogenous Retinoic Acid in Liver of Adult Rats, Accession No. AF320509.
Natiional Center for Biotechnology Information General Identifier No. 16151828, Oct. 16, 2001, T. Matsuzaka et al., Dual Gene Regulation of Mouse Delta-5 and -6 Desaturases by SREBP-1 and PPAR Alpha, Accession No. AB072976.
National Center for Biotechnology Information General Identifier No. 20069122, Apr. 8, 2002, X. Qui et al., Identification of Delta 4 Fatty Acid Desaturase From Thraustochytrium SP, Involved in the Biosynthesis of Docosahexanoic Acid by Heterologous Expression in Saccharomyces Cerevisiae and Brassica Juncea, Accession No. AF489588.

(Continued)

*Primary Examiner*—Elizabeth F McElwain
(74) *Attorney, Agent, or Firm*—Lynne M. Christenbury

(57) ABSTRACT

The present invention relates to a Δ5 desaturase, which has the ability to convert dihomo-γ-linolenic acid (DGLA; 20:3 ω-6) to arachidonic acid (ARA; 20:4 ω-6) and/or eicosatetraenoic acid (ETA; 20:4 ω-3) to eicosapentaenoic acid (EPA; 20:5 ω-3). Isolated nucleic acid fragments and recombinant constructs comprising such fragments encoding Δ5 desaturase along with a method of making long chain polyunsaturated fatty acids (PUFAs) using this Δ5 desaturase in oleaginous yeast are disclosed.

17 Claims, 11 Drawing Sheets

OTHER PUBLICATIONS

National Center for Biotechnology Information General Identifier No. 23894017, Apr. 15, 2005, E. Hornung et al., Specific Formation of Arachidonic Acid by a Front-End Delta5-Desaturase From *Phytophthora megasperma*, Accession No. AJ510244.

National Center for Biotechnology Information General Identifier No. 16033739, Mar. 24, 2005, H. Hong et al., Isolation and Characterization of Delta 5 FA Desaturase From Phythium Irregulare by Heterologous Expression in *Saccharomyces cerevisiae* and Oilseed Crops, Accession No. AF419297.

Natioanl Center for Biotechnology Information General Identifer No. 3859487, Nov. 11, 1998, D.S. Knutzon et al., Identification of Delta5-Desaturase From *Mortierella alpina* by Heterologous Expression in Bakers' Yeast and Canola, AF067654.

National Center for Biotechnology Information General Identifier No. 4150955, Apr. 17, 2003, T. Saito et al., A Second Functional Delta5 Fatty Acid Desaturase in the Cellular Slime Mould *Dictyostelium discoideum*, Accession No. AB022097.

National Center for Biotechnology Information General Identifier No. 16033740, Mar. 24, 2005, H. Hong et al., Isolation and Characterization of a Delta5 FA Desaturase From Pythium Irregulare by Heterologous Expression in *Saccharomyces cerevisiae* and Oilseed Crops, Accession No. AAL13311.

National Center for Biotechnology Information General Identifier No. 23894018, Apr. 15, 2005, E. Hornung et al., Specific Formation of Arachidonic Acid by a Front-End Delta5-Desaturase From *Phytophthora megasperma*, Accession No. CAD53323.

National Center for Biotechnology Information General Identifier No. 19879687, Aug. 23, 2002, F. Domergue et al., Cloning and Functional Characterization of *Phaeodactylum tricornutum* Front-End Desaturases Involved in Eicosapentaenoic Acid Biosynthesis, Accession No. AAL92562.

National Center for Biotechnology Information General Identifier No. 66812304, Aug. 17, 2006, L. Eichinger et al., The Genome of the Social Amoeba *Dictyostelium discoideum*, Accession No. XP640331.

U.S. Appl. No. 60/915,733, filed May 3, 2007, Howard Glenn Damude et al.

U.S. Appl. No. 10/840,579, filed May 6, 2004, Stephen K. Picataggio et al.

U.S. Appl. No. 10/840,325, filed May 6, 2004, Narendra S. Yadav et al.

U.S. Appl. No. 10/869,630, filed Jun. 16, 2004, Stephen K. Picataggio et al.

U.S. Appl. No. 10/882,760, filed Jul. 1, 2004, Narendra S. Yadav et al.

U.S. Appl. No. 10/985,254, filed Nov. 10, 2004, Narendra S. Yadav et al.

U.S. Appl. No. 10/985,691, filed Nov. 10, 2004, Narendra S. Yadav et al.

U.S. Appl. No. 11/024,544, filed Dec. 29, 2004, Narendra S. Yadav et al.

U.S. Appl. No. 11/166,993, filed Jun. 24, 2005, Howard Glenn Damude et al.

U.S. Appl. No. 11/183,664, filed Jul. 18, 2005, Stephen K. Picataggio et al.

U.S. Appl. No. 11/185,301, filed Jul. 20, 2005, Zhixiong Xue et al.

U.S. Appl. No. 11/190,750, filed Jul. 27, 2005, Stephen K. Picataggio et al.

U.S. Appl. No. 11/198,975, filed Aug. 8, 2005, Quinn Qun Zhu et al.

U.S. Appl. No. 11/225,354, filed Sep. 13, 2005, Zhixiong Xue et al.

U.S. Appl. No. 11/253,882, filed Oct. 19, 2005, Daniel Joseph Macool et al.

U.S. Appl. No. 11/264,784, filed Nov. 1, 2005, Howard Glenn Damude et al.

U.S. Appl. No. 11/264,737, filed Nov. 1, 2005, Howard Glenn Damude et al.

U.S. Appl. No. 11/265,761, filed Nov. 2, 2005, Howard Glenn Damude et al.

U.S. Appl. No. 60/795,810, filed Apr. 28, 2006, Howard Glenn Damude et al.

U.S. Appl. No. 60/793,575, filed Apr. 20, 2006, Zhixiong Xue et al.

U.S. Appl. No. 60/796,637, filed May 1, 2006, Narendra S. Yadav et al.

U.S. Appl. No. 60/801,172, filed May 17, 2006, Howard Glenn Damude et al.

U.S. Appl. No. 60/853,563, filed Oct. 23, 2006, Howard Glenn Damude et al.

U.S. Appl. No. 60/855,177, filed Oct. 30, 2006, Zhixiong Xue et al.

U.S. Appl. No. 11/601,563, filed Nov. 16, 2006, Howard Glenn Damude et al.

U.S. Appl. No. 11/601,564, filed Nov. 16, 2006, Howard Glenn Damude et al.

U.S. Appl. No. 11/635,258, filed Dec. 7, 2006, Howard Glenn Damude et al.

U.S. Appl. No. 11/613,420, filed Dec. 20, 2006, John E. Seip et al.

U.S. Appl. No. 60/909,790, filed Apr. 3, 2007, Howard Glenn Damude et al.

U.S. Appl. No. 60/911,925, filed Apr. 16, 2007, Howard Glenn Damude et al.

U.S. Appl. No. 60/910,831, filed Apr. 10, 2007, Howard Glenn Damude et al.

International Preliminary Report on Patentability and Written Opinion in corresponding PCT application PCT/US2007/011776, dated Nov. 27, 2008.

* cited by examiner

| Pos | Sequence | SEQ ID |
|---|---|---|
| 1 | M G K G G D G G A Q A A V S G T D A S L - - - A E V S S V D S K S V H V V L Y G | SEQ ID NO:18 (Pavlova lutheri).pro |
| 1 | M G R G G D S S G Q A A H P A A E L A V P S D R A E V S N A D S K A L H I - V L Y G | SEQ ID NO:64 (Pavlova salina).pro |
| 1 | M K - - - - S - K R Q A L P - - - - - - - - - - - - - - - - - - - - - L T - I D | SEQ ID NO:16 (Euglena gracillis).pro |
| 1 | M S - - - - T L D R Q S I F T I K E L E S I S Q R I H D G D E E A M K F I - I I D | SEQ ID NO:63 (Rhizopus stolonifer).pro |
| 1 | M S - - - - T L D R Q S I F T I K E L E S I S Q R I H D G D E E A M K F I - I I D | SEQ ID NO:51 (Rhizopus stolonifer).pro |
| 37 | K R V - D V T K F Q K A H P G G S K V F R I F Q E R D A T E Q F E S Y H S P K A | SEQ ID NO:18 (Pavlova lutheri).pro |
| 41 | K R V - D V T K F Q R T H P G G S K V F R - F Q D R D D A T D A F M V M H S Q E A | SEQ ID NO:64 (Pavlova salina).pro |
| 14 | G T T Y D V T E F I E D H P G G A Q V L L T H V G K D A S D V F H A M H P E S A | SEQ ID NO:16 (Euglena gracillis).pro |
| 37 | K K V Y D V T E F I E D H P G G A Q V L L T H V G K D A S D V F H A M H P E S A | SEQ ID NO:63 (Rhizopus stolonifer).pro |
| 37 | K K V Y D V T E F I E D H P G G A Q V L L T H V G K D A S D V F H A M H P E S A | SEQ ID NO:51 (Rhizopus stolonifer).pro |
| 76 | I K M M E G M L K K S E D A P A S V P L P S R S T M G T E F K E M I E R H K R A | SEQ ID NO:18 (Pavlova lutheri).pro |
| 80 | I K M M E G M L K K S E D A P A D T P L P S Q S P M G K D F K A M L E R H V A A | SEQ ID NO:64 (Pavlova salina).pro |
| 54 | F D K L K R - M P K I - N P S S E L P P Q A A V N E A Q E D F R K L R E E L I A T | SEQ ID NO:16 (Euglena gracillis).pro |
| 77 | Y E V L N N Y F V G D V Q E T V V T E K S S S S A Q F A V E M R Q L R D Q L K K E | SEQ ID NO:63 (Rhizopus stolonifer).pro |
| 77 | Y E V L N N Y F V G D V Q E T V V T E K S S S S A Q F A V E M R Q L R D Q L K K E | SEQ ID NO:51 (Rhizopus stolonifer).pro |
| 116 | G L Y D P C P L D E L F K L T I V L A P I F V G A Y L V - - - - R S G V - S P L | SEQ ID NO:18 (Pavlova lutheri).pro |
| 120 | G Y Y D P C P L D E L F K L S L V L L P T F A G M Y M L - - - - K A G V G S P L | SEQ ID NO:64 (Pavlova salina).pro |
| 93 | G M F D A S P L W Y S Y K I S T T L G L V L G Y F L M V Q Y Q M - - - - - Y F | SEQ ID NO:16 (Euglena gracillis).pro |
| 117 | G Y F H S S K L F Y A Y K V L S T L A I C I A G L S P L L Y A Y G R T S T L A V V | SEQ ID NO:63 (Rhizopus stolonifer).pro |
| 117 | G Y F H S S K L F Y A Y K V L S T L A I C I A G L S L L Y A Y G R T S T L A V V | SEQ ID NO:51 (Rhizopus stolonifer).pro |
| 151 | A G A L - S M G F G F Y L D G W L A H D Y L H H A V F K G S V N T L V K A N N A M | SEQ ID NO:18 (Pavlova lutheri).pro |
| 156 | C G A L - M V S F G W Y L D G W L A H D Y L H H S V F K G S V A R T V G W N N A A | SEQ ID NO:64 (Pavlova salina).pro |
| 128 | I G A V L L G M H Y Q Q M G W L S H D I C H H Q T F - K N R - - - - - N W N N L V | SEQ ID NO:16 (Euglena gracillis).pro |
| 157 | A S A I - T V G I F W Q Q C G W L A H D F G H H Q C F E D R - - - - - T W N D V L | SEQ ID NO:63 (Rhizopus stolonifer).pro |
| 157 | A S A I - T V G I F W Q Q C G W L A H D F G H H Q C F E D R - - - - - T W N D V L | SEQ ID NO:51 (Rhizopus stolonifer).pro |
| 191 | G Y A L G - F L Q G Y D V A W W R A R H N T H H V C T N E D G S D P D I K T A P | SEQ ID NO:18 (Pavlova lutheri).pro |
| 196 | G Y F L G - F V Q G Y A V E W W R A R H N T H H V C T N E D G S D P D I K T A P | SEQ ID NO:64 (Pavlova salina).pro |
| 163 | G L V F G N G L Q G F S V T W W K D R H N A H H S A T N V Q G H D P D I D N L P | SEQ ID NO:16 (Euglena gracillis).pro |
| 192 | V V F L G N F C Q G F S L S W W K N K H N T H H A S T N V H G Q D P D I D T A P | SEQ ID NO:63 (Rhizopus stolonifer).pro |
| 192 | V V F L G N F C Q G F S L S W W K N K H N T H H A S T N V H G Q D P D I D T A P | SEQ ID NO:51 (Rhizopus stolonifer).pro |

Figure 8B

```
                   250                260                270                280
     230  L L I Y - - - - - - - - - - V R E N P S I A K R L - - - N F F Q R W Q Q Y Y Y    SEQ ID NO:18 (Pavlova lutheri).pro
     235  L L I Y - - - - - - - - - - V R N K P S I A K R L - - - N A F Q R Y Q Q Y Y Y    SEQ ID NO:64 (Pavlova salina).pro
     203  L L A W S E - - - - - - D D V T R A S P I L S R K L I Q F Q - - - - - Q Y Y F    SEQ ID NO:16 (Euglena gracillis).pro
     232  V L L W D E Y A S A A Y Y A S L D Q E P T M V S R F L A E Q V L P H Q T R Y F F    SEQ ID NO:63 (Rhizopus stolonifer).pro
     232  V L L W D E Y A S A A Y Y A S L D Q E P T M V S R F L A E Q V L P H Q T R Y F F    SEQ ID NO:51 (Rhizopus stolonifer).pro 290                300                310                320
     256  V P T M A I L D L Y W R L E S I A Y Y A V R - - L P K M W M Q A A - - - - - -    SEQ ID NO:18 (Pavlova lutheri).pro
     261  V P V M A I L D L Y W R L E S I A Y Y A M R - - L P K M L P Q A L - - - - - -    SEQ ID NO:64 (Pavlova salina).pro
     230  L V I C I L L R F I W C F Q S V - - L T V R S L - K D R D N Q F Y R S Q Y K K    SEQ ID NO:16 (Euglena gracillis).pro
     272  F I L - A F A R L S W A L Q S L S Y S F K K E S I N K S R Q L N L F - - - - -    SEQ ID NO:63 (Rhizopus stolonifer).pro
     272  F I L - A F A R L S W A L Q S L S Y S F K K E S I N K S R Q L N L F - - - - -    SEQ ID NO:51 (Rhizopus stolonifer).pro 330                340                350                360
     287  - - - - A L A A H Y A L L C W V F A A H L N L I P L M M - V A R G F            SEQ ID NO:18 (Pavlova lutheri).pro
     292  - - - - A L V A H Y A L V A W V F A G N Y H L L P L V T - V L R G F            SEQ ID NO:64 (Pavlova salina).pro
     266  E A I G L A L H W T L K T L F H L F - F M P S I - L T S L L V F F V S E L V G G F  SEQ ID NO:16 (Euglena gracillis).pro
     305  E R V C I V G H W A L S A - F C I Y S W C S N V Y Y H M V L F F L V S Q A T T G Y  SEQ ID NO:63 (Rhizopus stolonifer).pro
     305  E R V C I V G H W A L F A - F C I Y S W C S N V Y Y H M V L F F L V S Q A T T G Y  SEQ ID NO:51 (Rhizopus stolonifer).pro 370                380                390                400
     316  A T G I V V F A T H Y G E D I L D R E H V E G M T L V E Q T A K T S R N I T G G    SEQ ID NO:18 (Pavlova lutheri).pro
     321  G T G I T V F A T H Y G E D I L D A D Q V R H M T L V E Q T A L T S R N I S G G    SEQ ID NO:64 (Pavlova salina).pro
     305  G I A L V F M N H Y P L E K I G D S V W D G H G F S V G Q I H E T M N I R R G    SEQ ID NO:16 (Euglena gracillis).pro
     344  T L A L V F A L N H N G M P V I T E E K A E S M E F F E I Q V I T G R D V T L S    SEQ ID NO:63 (Rhizopus stolonifer).pro
     344  T L A L V F A L N H N G M P V I T E E K A E S M E F F E I Q V I T G R D V T L S    SEQ ID NO:51 (Rhizopus stolonifer).pro 410                420                430                440
     356  W L V N V L T G F I S L Q T E H H H L F P M M M P T G N L M T I Q P E V R D F F K K  SEQ ID NO:18 (Pavlova lutheri).pro
     361  W L V N V L T G F I S L Q T E H H H L F P M M M P T G N L M T I Q P E V R A F F K K  SEQ ID NO:64 (Pavlova salina).pro
     345  I I T D W F F G G L N Y Q I E H H H L W P T L P R H N L T A V S Y Q V E Q L C Q K    SEQ ID NO:16 (Euglena gracillis).pro
     384  P L G D W F M G G L N Y Q I E H H H V F P N M P R H N L P T V K P M V K S L C Q K    SEQ ID NO:63 (Rhizopus stolonifer).pro
     384  P L G D W F M G G L N Y Q I E H H H V F P N M P R H N L P T V K P M V K S L C Q K    SEQ ID NO:51 (Rhizopus stolonifer).pro 450                460                470
     396  H G L E Y R E G N L F Q C V H Q N I K A L A F E H L L H                              SEQ ID NO:18 (Pavlova lutheri).pro
     401  H G L E Y R E G N L L E C V V R Q N I R A L A F E H L L L                            SEQ ID NO:64 (Pavlova salina).pro
     385  H N L P Y R N P L P H E G L V I L L R Y L A V F A R M A E K Q P A G K A L            SEQ ID NO:16 (Euglena gracillis).pro
     424  Y D I N Y H D T G F L K G T L E V L Q T L D I T S K L S L - Q L S K K S F            SEQ ID NO:63 (Rhizopus stolonifer).pro
     424  Y D I N Y H D T G F L K G T L E V L Q T L D I T S K L S L - Q L S K K S F            SEQ ID NO:51 (Rhizopus stolonifer).pro
```

| Fatty Acid | Clone | Gene | Fatty acid composition (wt.%) | | | | | | | | | | | | | | |
|---|---|---|---|---|---|---|---|---|---|---|---|---|---|---|---|---|---|
| | | | 16:0 | 16:1 | 18:0 | 18:1 | LA | GLA | ALA | STA | EDA | SCI | DGLA | ARA | ETrA | JUP | ETA | EPA |
| None | pY98 | MaD5 | 9.5 | 9.5 | 0.7 | 37.4 | 42.8 | 0.0 | 0.0 | 0.0 | 0.0 | 0.0 | 0.0 | 0.0 | 0.0 | 0.0 | 0.0 | 0.0 |
| | pDMW367 | EgD5 | 9.8 | 10.0 | 0.3 | 24.1 | 55.7 | 0.0 | 0.0 | 0.0 | 0.0 | 0.0 | 0.0 | 0.0 | 0.0 | 0.0 | 0.0 | 0.0 |
| EDA | pY98 | MaD5 | 9.8 | 8.2 | 0.8 | 39.7 | 34.1 | 0.0 | 0.0 | 0.0 | 7.1 | 0.2 | 0.0 | 0.0 | 0.0 | 0.0 | 0.0 | 0.0 |
| | pDMW367 | EgD5 | 9.6 | 7.7 | 0.9 | 33.6 | 39.4 | 0.0 | 0.0 | 0.0 | 8.1 | 0.8 | 0.0 | 0.0 | 0.0 | 0.0 | 0.0 | 0.0 |
| DGLA | pY98 | MaD5 | 12.0 | 6.8 | 1.4 | 38.8 | 19.3 | 0.6 | 0.0 | 0.0 | 0.0 | 0.0 | 18.2 | 3.0 | 0.0 | 0.0 | 0.0 | 0.0 |
| | pDMW367 | EgD5 | 12.4 | 6.9 | 0.9 | 32.8 | 22.9 | 1.1 | 0.0 | 0.0 | 0.0 | 0.0 | 13.7 | 9.3 | 0.0 | 0.0 | 0.0 | 0.0 |
| ETrA | pY98 | MaD5 | 8.9 | 7.2 | 1.0 | 41.2 | 17.2 | 0.0 | 12.1 | 0.0 | 0.0 | 0.0 | 0.0 | 0.0 | 11.7 | 0.6 | 0.0 | 0.0 |
| | pDMW367 | EgD5 | 8.8 | 7.2 | 0.6 | 35.8 | 18.4 | 0.0 | 16.2 | 0.0 | 0.0 | 0.0 | 0.0 | 0.0 | 12.3 | 0.7 | 0.0 | 0.0 |
| ETA | pY98 | MaD5 | 11.9 | 6.5 | 0.8 | 38.5 | 12.2 | 0.0 | 0.0 | 0.4 | 0.0 | 0.0 | 0.0 | 0.0 | 0.0 | 0.0 | 26.1 | 3.6 |
| | pDMW367 | EgD5 | 10.4 | 7.1 | 0.6 | 30.2 | 16.2 | 0.0 | 0.0 | 0.9 | 0.0 | 0.0 | 0.0 | 0.0 | 0.0 | 0.0 | 23.6 | 11.0 |

B

| Fatty Acid | Clone | Gene | % delta-5 desat | Ratio Desat Eg/Ma | Ratio Prod/By-Prod | Ratio Prod/By-Prod Eg/Ma | Ratio n-6/n-3 |
|---|---|---|---|---|---|---|---|
| None | pY98 | MaD5 | | | | | |
| | pDMW367 | EgD5 | | | | | |
| EDA | pY98 | MaD5 | 3.4 | 2.7 | | | 0.68 |
| | pDMW367 | EgD5 | 8.9 | | | | 1.76 |
| DGLA | pY98 | MaD5 | 14.0 | 2.9 | 4.17 | | 1.17 |
| | pDMW367 | EgD5 | 40.3 | | 4.52 | 1.08 | 1.27 |
| ETrA | pY98 | MaD5 | 4.9 | 1.0 | | | |
| | pDMW367 | EgD5 | 5.1 | | | | |
| ETA | pY98 | MaD5 | 12.0 | 2.6 | 2.44 | | |
| | pDMW367 | EgD5 | 31.8 | | 6.25 | 2.56 | |

Δ5 DESATURASE AND ITS USE IN MAKING POLYUNSATURATED FATTY ACIDS

This application claims the benefit of U.S. Provisional Patent Application 60/801,172, filed May 17, 2006.

FIELD OF THE INVENTION

This invention is in the field of biotechnology. More specifically, this invention pertains to the identification of nucleic acid fragments encoding a delta 5 fatty acid desaturase enzyme and the use of this desaturase in making long chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg, J. et al., *Amer. J. Clin. Nutr.*, 28:958-966 (1975); Dyerberg, J. et al., *Lancet*, 2(8081):117-119 (Jul. 15, 1978); Shimokawa, H., *World Rev. Nutr. Diet*, 88:100-108 (2001); von Schacky, C. and Dyerberg, J., *World Rev. Nutr. Diet*, 88:90-99 (2001)). And, numerous other studies document wide-ranging health benefits conferred by administration of ω-3 and/or ω-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts (even those natively limited to LA and ALA fatty acid production) can be substantially altered to result in high-level production of various long-chain ω-3/ω-6 PUFAs. Whether this is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) may all require expression of a Δ5 desaturase.

Most Δ5 desaturase enzymes identified so far have the primary ability to convert dihomo-γ-linolenic acid (DGLA; 20:3 ω-6) to ARA, with secondary activity in converting eicosatetraenoic acid (ETA; 20:4 ω-3) to EPA (where DHA is subsequently synthesized from EPA following reaction with an additional $C_{20/22}$ elongase and a Δ4 desaturase). The Δ5 desaturase has a role in both the Δ6 desaturase/Δ6 elongase pathway (which is predominantly found in algae, mosses, fungi, nematodes and humans and which is characterized by the production of γ-linoleic acid (GLA; 18:3 ω-6) and/or stearidonic acid (STA; 18:4 ω-3)) and the Δ9 elongase/Δ8 desaturase pathway (which operates in some organisms, such as euglenoid species and which is characterized by the production of eicosadienoic acid (EDA; 20:2 ω-6) and/or eicosatrienoic acid (ETrA; 20:3 ω-3)) (FIG. 1).

Based on the role Δ5 desaturase enzymes play in the synthesis of e.g., ARA, EPA and DHA, there has been considerable effort to identify and characterize these enzymes from various sources. As such, numerous Δ5 desaturases have been disclosed in both the open literature (e.g., GenBank Accession No. AF199596, No. AF226273, No. AF320509, No. AB072976, No. AF489588, No. AJ510244, No. AF419297, No. AF07879, No. AF067654 and No. AB022097) and the patent literature (e.g., U.S. Pat. Nos. 5,972,664 and 6,075,183; see also commonly owned, co-pending Provisional Applications No. 60/801,119 (filed May 17, 2006) disclosing amino acid and nucleic acid sequences for a Δ5 desaturase enzyme from *Peridium* sp. CCMP626; and No. 60/915,733 (filed May 3, 2007) disclosing amino acid and nucleic acid sequences for a □5 desaturase enzyme from *Euglena anabaena*.

Applicants have identified and isolated new genes encoding □5 desaturases that are be suitable for heterologous expression in a variety of host organisms for use in the production of ω-3/ω-6 fatty acids. Specifically new genes encoding Δ5 desaturase from *Euglena gracilis* have been discovered.

SUMMARY OF THE INVENTION

The present invention relates to new genetic constructs encoding polypeptides having Δ5 desaturase activity, and their use in algae, bacteria, yeast, euglenoids and fungi for the production of PUFAs.

Accordingly the invention provides an isolated nucleic acid molecule selected from the group consisting of:
  (a) an isolated nucleotide sequence encoding a Δ5 desaturase enzyme as set forth in SEQ ID NO:2;
  (b) an isolated nucleotide sequence that hybridizes with (a) under the following hybridization conditions: 0.1×SSC, 0.1% SDS, 65° C. and washed with 2×SSC, 0.1% SDS followed by 0.1×SSC, 0.1% SDS; and,
  (c) an isolated nucleotide sequence that is completely complementary to (a) or (b).

In another embodiment the invention provides an isolated nucleic acid molecule comprising a first nucleotide sequence encoding a Δ5 desaturase enzyme of at least 449 amino acids that has at least 95% identity based on BLASTP algorithms when compared to a polypeptide having the sequence as set forth in SEQ ID NO:2;
or a second nucleotide sequence comprising the complement of the first nucleotide sequence.

In other embodiments the invention provides genetic chimera of the nucleic acid molecules encoding the Δ5 desaturases described herein and transformed host cells comprising the same.

In another embodiment the invention provides a method for the production of arachidonic acid comprising:
  a) providing a host cell comprising:
    (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
    (ii) a source of dihomo-γ-linoleic acid;
  b) growing the host cell of step (a) under conditions wherein the nucleic acid fragment encoding the Δ5 desaturase polypeptide is expressed and the dihomo-γ-linoleic acid is converted to arachidonic acid; and,
  c) optionally recovering the arachidonic acid of step (b).

Similarly the invention provides a method for the production of eicosapentaenoic acid comprising:

a) providing a host cell comprising:
   (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
   (ii) a source of eicosatetraenoic acid;
b) growing the host cell of step (a) under conditions wherein the nucleic acid fragment encoding the Δ5 desaturase polypeptide is expressed and the eicosatetraenoic acid is converted to eicosapentaenoic acid; and,
c) optionally recovering the eicosapentaenoic acid of step (b).

BRIEF DESCRIPTION OF THE DRAWINGS AND SEQUENCE LISTINGS

FIG. 3 shows a portion of an alignment between and among Δ5 desaturase proteins and Δ8 desaturase proteins using a Clustal W analysis (MegAlign™ program of DNASTAR software).

Figure 4:
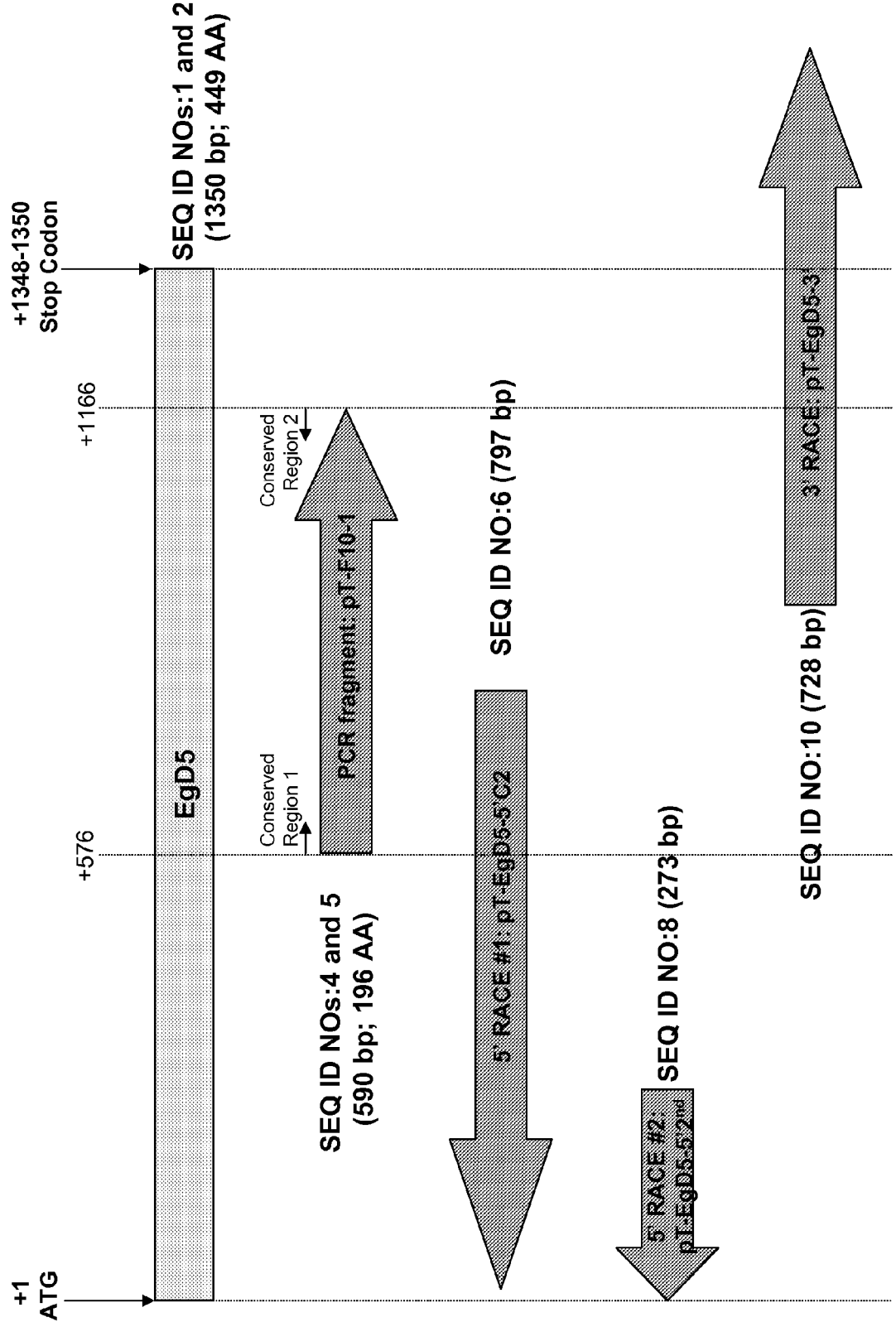

FIG. 4 graphically represents the relationship between SEQ ID NOs:1, 2, 4, 5, 6, 8 and 10, each of which relates to the *Euglena gracilis* Δ5 desaturase.

Figure 5:
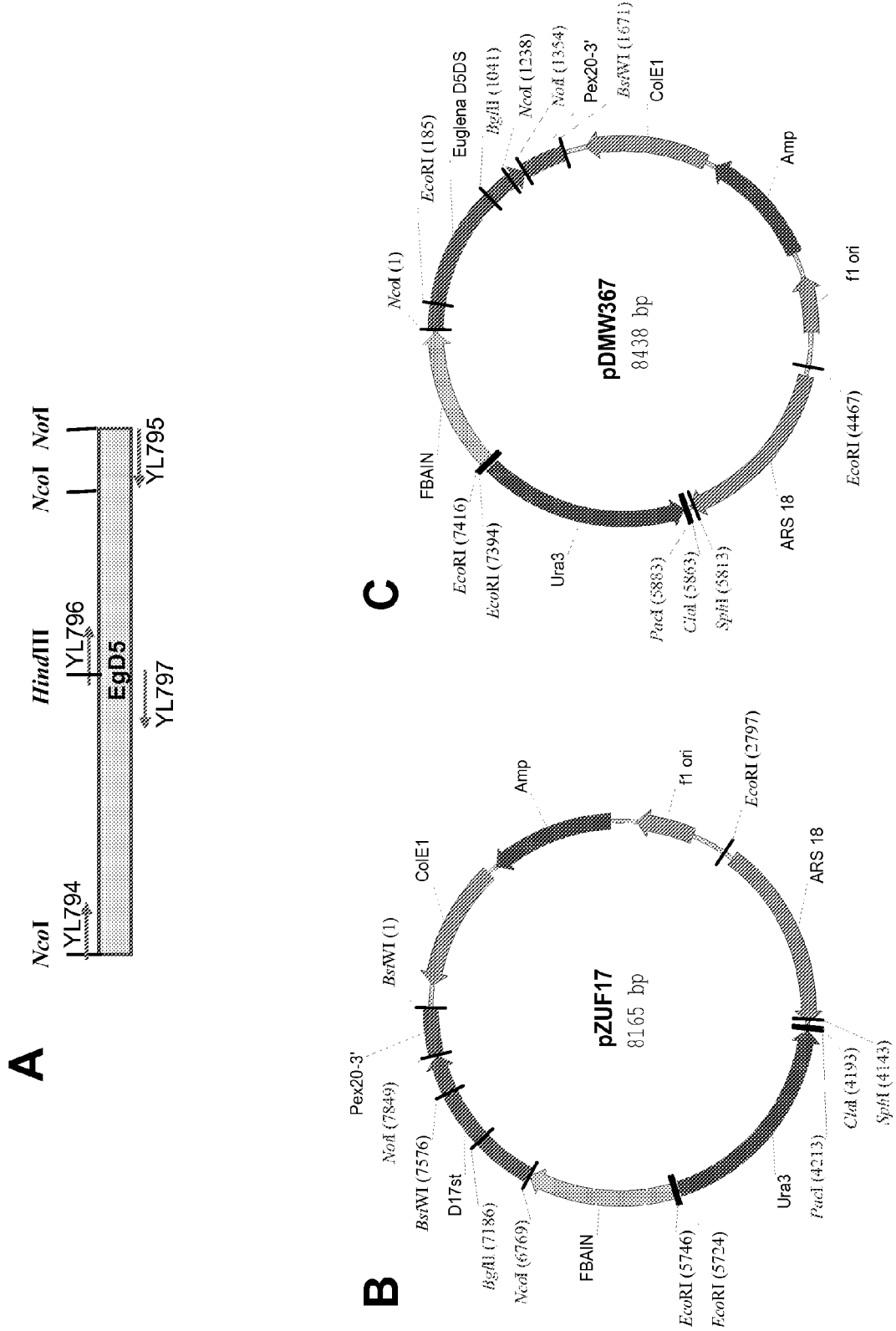

FIG. 5A illustrates the cloning strategy utilized for amplification of the *Euglena gracilis* Δ5 desaturase gene (EgD5). FIG. 5B is a plasmid map of pZUF17, while FIG. 5C is a plasmid map of pDMW367.

Figure 6:

FIG. 6 provides plasmid maps for the following: (A) pKUNF12T6E; (B) pEgD5S; and, (C) pDMW369.

FIG. 7 shows a comparison of the DNA sequence of the *Euglena gracilis* Δ5 desaturase gene (designated as "EgD5"; SEQ ID NO:1) and the synthetic gene (designated as "EgD5S"; SEQ ID NO:3) codon-optimized for expression in *Yarrowia lipolytica*.

FIGS. 8A and 8B show a Clustal V alignment (with default parameters) of a *Pavlova lutheri* Δ8 desaturase (SEQ ID NO:18), a *Pavlova salina* Δ8 desaturase (SEQ ID NO:64), a *Euglena gracilis* Δ8 desaturase (SEQ ID NO:16) and two different *Rhizopus stolonifer* Δ6 fatty acid desaturases (SEQ ID NOs:51 and 63).

Figure 9:
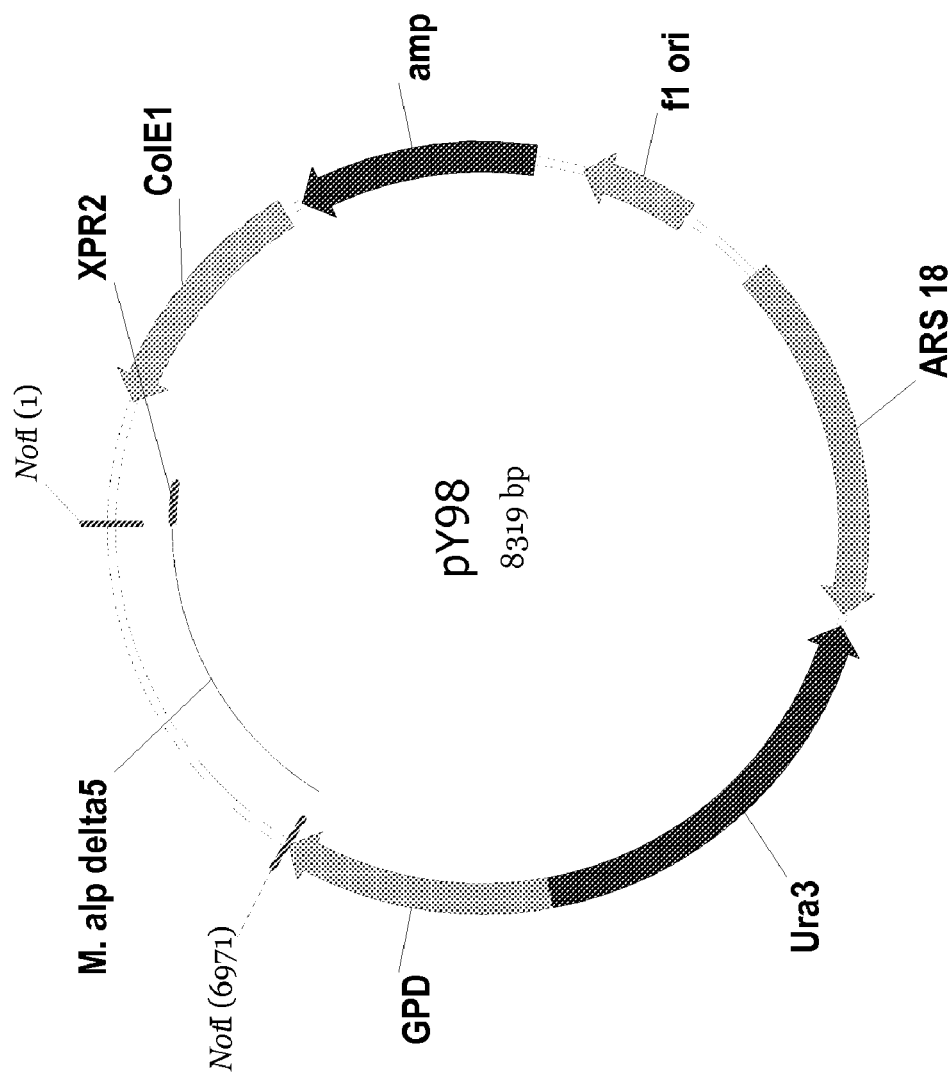

FIG. 9 provides a plasmid map for pY98.

FIG. 10A provides the fatty acid profiles for *Yarrowia lipolytica* expressing pY98 (SEQ ID NO:76; comprising a *Mortierella alpina* Δ5 desaturase gene designated as "MaD5") or pDMW367 (SEQ ID NO:23; comprising the *Euglena gracilis* Δ5 desaturase gene designated as "EgD5") and fed various substrates. FIG. 10B provides a comparison of the ω-3 and ω-6 substrate specificity of MaD5 versus EgD5.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-26, 48, 49, 51-54, 61-64, 67-72 and 75-76 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Euglena gracilis* Δ5 desaturase ("EgD5") | 1 (1350 bp) | 2 (449 AA) |
| Synthetic Δ5 desaturase, derived from *Euglena gracilis*, codon-optimized for expression in *Yarrowia lipolytica* ("EgD5S") | 3 (1350 bp) | 2 (449 AA) |
| *Euglena gracilis* EgD5-fragment of pT-F10-1 | 4 (590 bp) | 5 (196 AA) |
| *Euglena gracilis* EgD5-fragment of pT-EgD5-5'C2 | 6 (797 bp) | — |
| *Euglena gracilis* EgD5-5' sequence relative to SEQ ID NO: 4 | 7 (559 bp) | — |
| *Euglena gracilis* EgD5-fragment of pT-EgD5-5'2$^{nd}$ | 8 (273 bp) | — |
| *Euglena gracilis* EgD5-5' sequence relative to SEQ ID NO: 6 | 9 (20 bp) | — |
| *Euglena gracilis* EgD5-fragment of pT-EgD5-3' | 10 (728 bp) | — |
| *Euglena gracilis* EgD5-3' sequence relative to SEQ ID NO: 4 | 11 (464 bp) | — |

TABLE 1-continued

Summary Of Nucleic Acid And Protein SEQ ID Numbers

| Description and Abbreviation | Nucleic acid SEQ ID NO. | Protein SEQ ID NO. |
|---|---|---|
| *Pythium irregulare* Δ5 desaturase (GenBank Accession No. AAL13311) | — | 12 (456 AA) |
| *Phytophthora megasperma* Δ5 desaturase (Gen Bank Accession No. CAD53323) | — | 13 (477 AA) |
| *Phaeodactylum tricornutum* Δ5 desaturase (Gen Bank Accession No. AAL92562) | — | 14 (469 AA) |
| *Dictyostelium discoideum* Δ5 desaturase (Gen Bank Accession No. XP_640331) | — | 15 (467 AA) |
| *Euglena gracilis* Δ8 desaturase (PCT Publications No. WO 2006/012325 and No. WO 2006/012326) | — | 16 (421 AA) |
| *Pavlova lutheri* (CCMP459) Δ8 desaturase | 17 (1269 bp) | 18 (423 AA) |
| Conserved Region 1 | — | 19 (7 AA) |
| Conserved Region 2 | — | 20 (7 AA) |
| *Thalassiosira pseudonana* Δ8 sphingolipid desaturase (GenBank Accession No. AAX14502) | — | 21 (476 AA) |
| Plasmid pZUF17 | 22 (8165 bp) | — |
| Plasmid pDMW367 | 23 (8438 bp) | — |
| Plasmid pKUNF12T6E | 24 (12,649 bp) | — |
| Synthetic $C_{18/20}$ elongase gene derived from *Thraustochytrium aureum* (U.S. Pat. No. 6,677,145), codon-optimized for expression in *Yarrowia lipolytica* ("EL2S") | 25 (819 bp) | 26 (272 AA) |
| Plasmid pEgD5S | 48 (4070 bp) | — |
| Plasmid pDMW369 | 49 (8438 bp) | — |
| *Rhizopus stolonifer* Δ6 fatty acid desaturase (NCBI Accession No. AAX22052) | — | 51 (459 AA) |
| *Pavlova lutheri* Δ8 desaturase-portion of cDNA insert from clone eps1c.pk002.f22 (5' end of cDNA insert) | 52 (695 bp) | — |
| *Pavlova lutheri* Δ8 desaturase-fully sequenced EST eps1c.pk002.f22:fis (full insert sequence) | 53 (1106 bp) | — |
| *Pavlova lutheri* Δ8 desaturase-translation of nucleotides 1-864 of fully sequenced EST eps1c.pk002.f22:fis (full insert sequence; SEQ ID NO: 53) | — | 54 (287 AA) |
| *Pavlova lutheri* Δ8 desaturase-full 5' end sequence from genome walking | 61 (1294 bp) | — |
| *Pavlova lutheri* Δ8 desaturase-assembled sequence | 62 (1927 bp) | — |

TABLE 1-continued

Summary Of Nucleic Acid And Protein SEQ ID Numbers

| Description and Abbreviation | Nucleic acid SEQ ID NO. | Protein SEQ ID NO. |
|---|---|---|
| *Rhizopus stolonifer* Δ6 fatty acid desaturase (NCBI Accession No. ABB96724) | — | 63 (459 AA) |
| *Pavlova salina* Δ8 desaturase | — | 64 (427 AA) |
| *Mortierella alpina* Δ5 desaturase | 67 (1338 bp) | 68 (446 AA) |
| Plasmid pY5-22 | 69 (6473 bp) | — |
| Plasmid pY5-22GPD | 70 (6970 bp) | — |
| *Yarrowia lipolytica* glyceraldehyde-3-phosphate dehydrogenase promoter (GPD) | 71 (968 bp) | — |
| Plasmid pYZDE2-S | 72 (8630 bp) | — |
| Plasmid pKR136 | 75 (6339 bp) | — |
| Plasmid pY98 | 76 (8319 bp) | — |

SEQ ID NOs:27-30 correspond to degenerate oligonucleotide primers 5-1A, 5-1B, 5-1C and 5-1D, respectively, that encode Conserved Region 1.

SEQ ID NOs:31-34 correspond to degenerate oligonucleotide primers 5-5AR, 5-5BR, 5-5CR and 5-5DR, respectively, that encode Conserved Region 2.

SEQ ID NOs:35-40 correspond to primers ODMW480, CDSIII 5' primer, ODMW479, DNR CDS 5', YL791 and YL792, respectively, used for 5' RACE.

SEQ ID NOs:41-43 correspond to primers ODMW469, AUAP and ODMW470, respectively, used for 3' RACE.

SEQ ID NOs:44-47 correspond to primers YL794, YL797, YL796 and YL795, respectively, used for amplification of the full length cDNA of EgD5.

SEQ ID NO:50 corresponds to primer T7, used for sequencing the *Pavlova lutheri* (CCMP459) cDNA library.

SEQ ID NOs:55 and 56 correspond to primers SeqE and SeqW, respectively, used for sequencing *Pavlova lutheri* (CCMP459) clones.

SEQ ID NOs:57 and 58 correspond to the universal primer AP1 and primer GSP PvDES, respectively, used for amplification of genomic *Pavlova lutheri* (CCMP459) DNA.

SEQ ID NOs:59 and 60 correspond to primers M13-28Rev and PavDES seq, respectively, used for sequencing *Pavlova lutheri* (CCMP459) genomic inserts.

SEQ ID NOs:65 and 66 correspond to AP primer and Smart IV oligonucleotide primer, respectively, used for *Euglena gracilis* cDNA synthesis.

SEQ ID NOs:73 and 74 are primers GPDsense and GPDantisense, respectively, used for amplifying the GPD promoter.

DETAILED DESCRIPTION OF THE INVENTION

All patents, patent applications, and publications cited herein are incorporated by reference in their entirety. This specifically includes the following commonly owned, co-pending applications: U.S. Pat. No. 7,125,672, U.S. Pat. No. 7,189,559, U.S. Pat. No. 7,192,762, U.S. Pat. No. 7,198,937, U.S. Pat. No. 7,202,356, U.S. patent applications Ser. No. 10/840,579 and Ser. No. 10/840,325 (filed May 6, 2004) now U.S. Pat. Nos. 7,238,482 and 7,214,491, U.S. patent application Ser. No. 10/869,630 (filed Jun. 16, 2004) now U.S. Pat. No. 7,259,255, U.S. patent application Ser. No. 10/882,760 (filed Jul. 1, 2004) now U.S. Pat. No. 7,267,976, U.S. patent application Ser. No. 10/985,254 and Ser. No. 10/985,691 (filed Nov. 10, 2004), wherein Ser. No. 10/985,691 is now U.S. Pat. No. 7,504,259, U.S. patent application Ser. No. 11/024,544 (filed Dec. 29, 2004) now U.S. Pat. No. 7,273,746, U.S. patent application Ser. No. 11/166,993 (filed Jun. 24, 2005) now U.S. Pat. No. 7,256,033, U.S. patent application Ser. No. 11/183,664 (filed Jul. 18, 2005) now U.S. Pat. No. 7,459,546, U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005) now U.S. Pat. No. 7,465,564, U.S. patent application Ser. No. 11/225,354 (filed Sep. 13, 2005) now U.S. Pat. No. 7,264,949, U.S. patent application Ser. No. 11/253,882 (filed Oct. 19, 2005) now U.S. Pat. No. 7,470,532, U.S. patent application Ser. s No. 11/264,784 and 11/264,737 (filed Nov. 1, 2005) now U.S. Pat. Nos. 7,588,931 and 7,550,286, U.S. patent application Ser. No. 11/265,761 (filed Nov. 2, 2005), U.S. Patent Application No. 60/795,810

(filed Apr. 28, 2006), U.S. Patent Application No. 60/793,575 (filed Apr. 20, 2006), U.S. Patent Application No. 60/796,637 (filed May 2, 2006), U.S. Patent Application No. 60/801,172 and No. 60/801,119 (filed May 17, 2006), U.S. Patent Application No. 60/853,563 (filed Oct. 23, 2006), U.S. Patent Application No. 60/855,177 (filed Oct. 30, 2006), U.S. patent applications Ser. Nos. 11/601,563 and Ser. No. 11/601,564 (filed Nov. 16, 2006), U.S. patent application Ser. No. 11/635,258 (filed Dec. 7, 2006), U.S. patent application Ser. No. 11/613,420 (filed Dec. 20, 2006), U.S. Patent Application No. 60/909,790 (filed Apr. 3, 2007), U.S. Patent Application No. 60/910,831 (filed Apr. 10, 2007) and U.S. Patent Application No. 60/915,733, (filed May 3, 2007).

Applicants have identified a novel *Euglena gracilis* Δ5 desaturase enzyme and gene encoding the same that may be used for the manipulation of biochemical pathways for the production of healthful PUFAs. Thus, the subject invention finds many applications.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used.

The following definitions are provided.
"Open reading frame" is abbreviated ORF.
"Polymerase chain reaction" is abbreviated PCR.
"American Type Culture Collection" is abbreviated ATCC.
"Polyunsaturated fatty acid(s)" is abbreviated PUFA(s).
"Triacylglycerols" are abbreviated TAGs.

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in U.S. Patent Publication No. 2005/0136519.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA or ERA | cis-11,14,17-eicosatrienoic | 20:3 ω-3 |
| Sciadonic | SCI | cis-5,11,14-eicosatrienoic | 20:3b ω-6 |
| Juniperonic | JUP | cis-5,11,14,17-eicosatetraenoic | 20:4b ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

Figure 1:
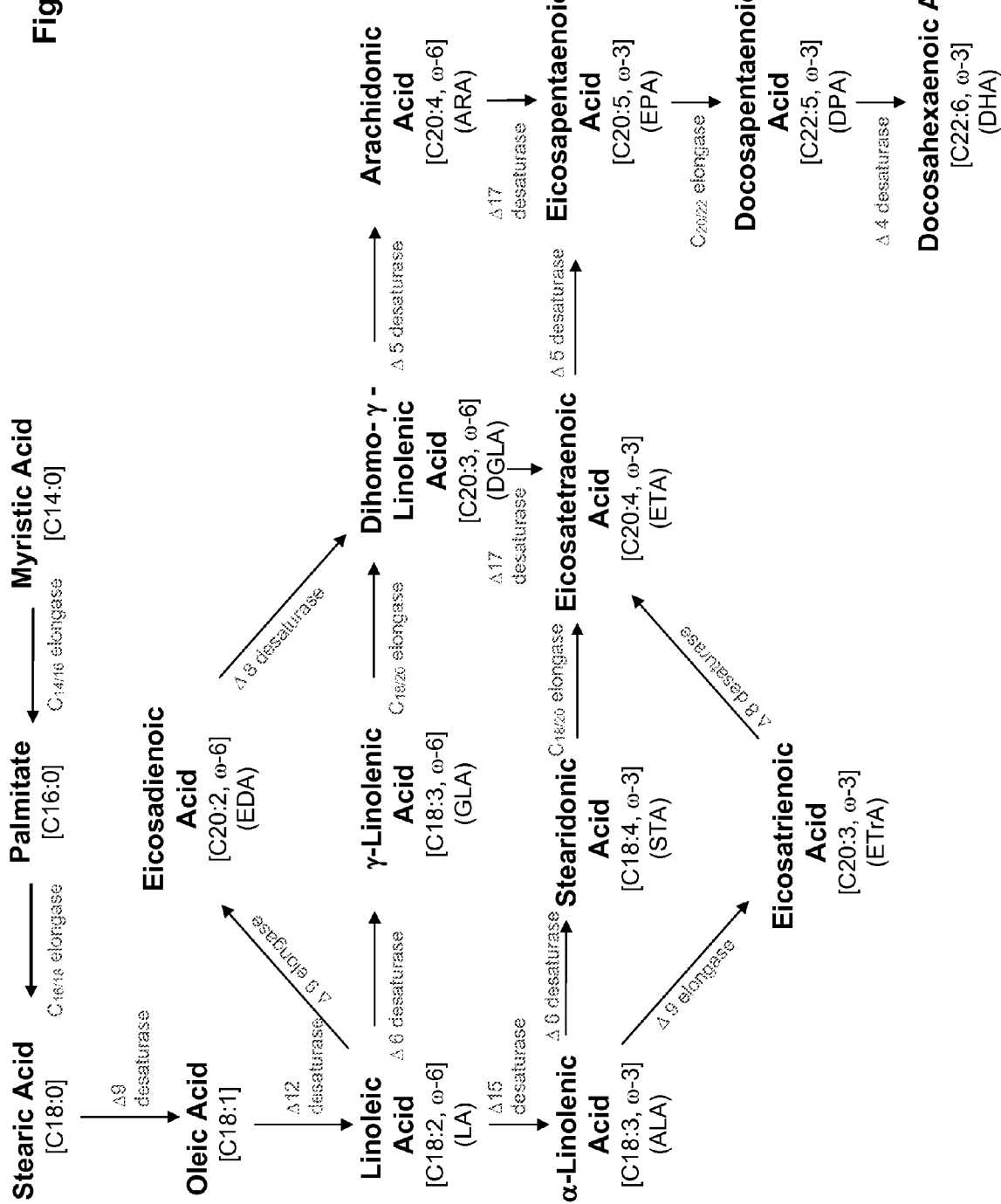
FIG. 1 illustrates the ω-3/ω-6 fatty acid biosynthetic pathway.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "Δ6 desaturase/Δ6 elongase pathway" will refer to a PUFA biosynthetic pathway that minimally includes at least one Δ6 desaturase and at least one $C_{18/20}$ elongase, thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "Δ9 elongase/Δ8 desaturase pathway" will refer to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the Δ9 elongase/Δ8 desaturase pathway, sciadonic acid (SCI) and juniperonic acid (JUP) also can be produced by the action of a Δ5 desaturase on either EDA or ETrA, respectively. They are considered to be "by-product fatty acids" since neither can be further converted to EPA by the action of other metabolic pathway enzymes.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ5 desaturases that catalyze the conversion of DGLA to ARA and/or ETA to EPA. Other desaturases include: 1.) Δ17 desaturases that desaturate a fatty acid between the $17^{th}$ and $18^{th}$ carbon atom numbered from the carboxyl-terminal end of the molecule and which, for example, catalyze the conversion of ARA to EPA and/or DGLA to ETA; 2.) Δ6 desaturases that catalyze the conversion of LA to GLA and/or ALA to STA; 3.) Δ12 desaturases that catalyze the conversion of oleic acid to LA; 4.) Δ15 desaturases that catalyze the conversion of LA to ALA and/or GLA to STA; 5.) Δ4 desaturases that catalyze the conversion of DPA to DHA; 6.) Δ8 desaturases that catalyze the conversion of EDA to DGLA and/or ETrA to ETA; and, 7.) Δ9 desaturases that catalyze the conversion of palmitate to palmitoleic acid (16:1) and/or stearate to oleic acid. In the art, Δ15 and Δ17 desaturases are also occasionally referred to as "omega-3 desaturases", "w-3 desaturases", and/or "ω-3 desaturases", based on their ability to convert ω-6 fatty acids into their ω-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

The term "EgD5" refers to a Δ5 desaturase enzyme (SEQ ID NO:2) isolated from *Euglena gracilis*, encoded by SEQ ID NO:1 herein. Similarly, the term "EgD5S" refers to a synthetic Δ5 desaturase derived from *Euglena gracilis* that is codon-optimized for expression in *Yarrowia lipolytica* (i.e., SEQ ID NOs:3 and 2).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in U.S. Patent Publication No. 2005/0132442.

Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., EPA). In like manner, a Δ9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase).

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ("euglenoids") found living in freshwater, marine, soil and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

As used herein, the terms "isolated nucleic acid fragment" or "isolated nucleic acid molecule" will be used interchangeably and refer to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular euglenoid proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the invention herein also includes isolated nucleic acid fragments that are complementary to the complete sequences as reported in the accompanying Sequence Listing, as well as those substantially similar nucleic acid sequences.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the present invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant euglenoid polypeptide as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and, 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, CABIOS, 5:151-153 (1989); Higgins, D.G. et al., Comput. Appl. Biosci., 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, CABIOS, 5:151-153 (1989); Higgins, D. G. et al., Comput. Appl. Biosci., 8:189-191(1992)) and found in the MegAlign™ v 6.1 program of the LASERGENE bioinformatics computing suite (DNASTAR Inc.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Although preferred ranges are described above, any integer amino acid identity from 39% to 100% may be useful in describing the present invention, such as 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. With regard to the BLASTP algorithm used herein, default parameters will include the Robinson and Robinson amino acid frequencies (Robinson A. B., Robinson L. R., *Proc. Natl Acad. Sci. U.S.A.*, 88:8880-8884 (1991)), the BLOSUM62 scoring matrix and the gap cost $\Delta(g)=11+g$.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

An Overview: Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and, 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ6 desaturase/Δ6 elongase pathway", ω-6 fatty acids are formed as follows: (1) LA is converted to GLA by a Δ6 desaturase; (2) GLA is converted to DGLA by a $C_{18/20}$ elongase; and, (3) DGLA is converted to ARA by a Δ5 desaturase. Alternatively, the "Δ6 desaturase/Δ6 elongase pathway" can be utilized for formation of ω-3 fatty acids as follows: (1) LA is converted to ALA, the first of the ω-3 fatty acids, by a Δ15 desaturase; (2) ALA is converted to STA by a Δ6 desaturase; (3) STA is converted to ETA by a $C_{18/20}$ elongase; (4) ETA is converted to EPA by a Δ5 desaturase; (5) EPA is converted to DPA by a $C_{20/22}$ elongase; and, (6) DPA is converted to DHA by a Δ4 desaturase. Optionally, ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize a Δ9 elongase and Δ8 desaturase. More specifically, LA and ALA may be converted to EDA and ETrA, respectively, by a Δ9 elongase; then, a Δ8 desaturase converts EDA to DGLA and/or ETrA to ETA.

It is contemplated that the particular functionalities required to be expressed in a specific host organism for production of ω-3/ω-6 fatty acids will depend on the host cell (and its native PUFA profile and/or desaturase/elongase profile), the availability of substrate, and the desired end product(s). One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or, 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of a Novel *Euglena gracilis* Δ5 Desaturase

In the present invention, a nucleotide sequence (SEQ ID NO:1) has been isolated from *Euglena gracilis* encoding a Δ5 desaturase (SEQ ID NO:2), designated herein as "EgD5".

Comparison of the EgD5 nucleotide base and deduced amino acid sequences to public databases reveals that the most similar known sequences are about 39% identical to the amino acid sequence of EgD5 reported herein over a length of 449 amino acids using a BLASTP search algorithm. More preferred amino acid fragments are at least about 70%-80% identical to the sequences herein, where those sequences that are at least about 80%-90% identical are particularly suitable and those sequences that are at least about 90%-95% identical are most preferred. Similarly, preferred EgD5 encoding nucleic acid sequences corresponding to the instant ORF are those encoding active proteins and which are at least about 70%-80% identical to the nucleic acid sequences of EgD5 reported herein, where those sequences that are at least about 80%-90% identical are particularly suitable and those sequences that are at least about 90%-95% identical are most preferred.

In alternate embodiments, the instant EgD5 desaturase sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one preferred embodiment of the invention herein, EgD5 was codon-optimized for expression in *Yarrowia lipolytica*. This was possible by first determining the *Y. lipolytica* codon usage profile (see PCT Publication No. WO 04/101757 and U.S. Pat. No. 7,125,672) and identifying those codons that were preferred. Then, for further optimization of gene expression in *Y. lipolytica*, the consensus sequence around the 'ATG' initiation codon was determined. This optimization resulted in modification of 196 bp of the 1350 bp coding region (14.5%) and optimization of 189 codons of the total 449 codons (42%). None of the modifications in the codon-optimized gene ("EgD5S"; SEQ ID NO:3) changed the amino acid sequence of the encoded protein (SEQ ID NO:2). As described in Example 11, the codon-optimized gene was 36% more efficient desaturating DGLA to ARA than the wildtype gene, when expressed in *Y. lipolytica*.

One skilled in the art would be able to use the teachings herein to create various other codon-optimized Δ5 desaturase proteins suitable for optimal expression in alternate hosts (i.e., other than *Yarrowia lipolytica*), based on the wildtype EgD5 sequence. Accordingly, the instant invention relates to any codon-optimized Δ5 desaturase protein that is derived from the wildtype EgD5 (i.e., encoded by SEQ ID NO:2). This includes, but is not limited to, the nucleotide sequence set forth in SEQ ID NO:3, which encodes a synthetic Δ5 desaturase protein (i.e., EgD5S) that was codon-optimized for expression in *Yarrowia lipolytica*.

Identification and Isolation of Homologs

Any of the instant desaturase sequences (i.e., EgD5, EgD5S) or portions thereof may be used to search for Δ5 desaturase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ5 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ5 desaturase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., Proc. Natl. Acad. Sci. U.S.A., 82:1074 (1985); or strand displacement amplification (SDA), Walker, et al., Proc. Natl. Acad. Sci. U.S.A., 89:392 (1992)]; and 3.) methods of library construction and screening by complementation.

For example, genes encoding similar proteins or polypeptides to the Δ5 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing ARA [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in Human Genetic Diseases: A Practical Approach, K. E. Davis Ed., (1986) pp 33-50, IRL: Herndon, Va.; and Rychlik, W., In Methods in Molecular Biology, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., Proc. Natl Acad. Sci. U.S.A., 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., Proc. Natl Acad. Sci. U.S.A., 86:5673 (1989); Loh et al., Science, 243:217 (1989)).

In other embodiments, any of the Δ5 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the Δ5 desaturase nucleic acid fragments described herein are exchanged with a functional domain in an alternate desaturase gene to thereby result in a novel protein.

Methods for Production of Various ω-3 and/or ω-6 Fatty Acids

It is expected that introduction of chimeric genes encoding the Δ5 desaturases described herein (i.e., EgD5, EgD5S or other mutant enzymes, codon-optimized enzymes or homologs thereof), under the control of the appropriate promoters, will result in increased production of ARA and/or EPA in the transformed host organism, respectively. As such, the present invention encompasses a method for the direct production of PUFAs comprising exposing a fatty acid substrate (i.e., DGLA or ETA) to the desaturase enzymes described herein (e.g., EgD5, EgD5S), such that the substrate is converted to the desired fatty acid product (i.e., ARA or EPA, respectively).

More specifically, it is an object of the present invention to provide a method for the production of ARA in a host cell (e.g., oleaginous yeast), wherein the host cell comprises:

(i) an isolated nucleotide molecule encoding a Δ5 desaturase polypeptide having at least 95% identity when compared to a polypeptide having an amino acid sequence as set forth in SEQ ID NO:2, based on BLASTP algorithms; and, (ii) a source of dihomo-γ-linoleic acid;

wherein the host cell is grown under conditions such that the Δ5 desaturase is expressed and the DGLA is converted to ARA, and wherein the ARA is optionally recovered.

The person of skill in the art will recognize that the broad substrate range of the Δ5 desaturase may additionally allow for the use of the enzyme for the conversion of ETA to EPA. Accordingly the invention provides a method for the production of EPA, wherein the host cell comprises:

(i) an isolated nucleotide molecule encoding a Δ5 desaturase polypeptide having at least 95% identity when compared to a polypeptide having an amino acid sequence as set forth in SEQ ID NO:2, based on BLASTP algorithms; and, (ii) a source of eicosatetraenoic acid;

wherein the host cell is grown under conditions such that the Δ5 desaturase is expressed and the ETA is converted to EPA, and wherein the EPA is optionally recovered.

Alternatively, each Δ5 desaturase gene and its corresponding enzyme product described herein can be used indirectly for the production of ω-3 fatty acids (see U.S. Patent Publication No. 2005/0136519). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ5 desaturases described herein (e.g., EgD5, EgD5S or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases, $C_{20/22}$ elongases) to result in higher levels of production of longer-chain ω-3 fatty acids (e.g., EPA, DPA and DHA). The particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ5 desaturase, based on the complete sequences described herein, the complement of those complete sequences, substantial portions of those sequences, codon-optimized desaturases derived therefrom and those sequences that are substantially homologous thereto.

Expression Systems, Cassettes and Vectors

The genes and gene products of the instant sequences described herein may be expressed in heterologous host cells. Expression in recombinant hosts may be useful for the production of various PUFA pathway intermediates, or for the modulation of PUFA pathways already existing in the host for the synthesis of new products heretofore not possible using the host.

Expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate host cells via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of the instant Δ5 desaturase ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see U.S. patent application Ser. No. 11/265,761, corresponding to PCT Publication No. WO 2006/052870 for preferred transcriptional initiation regulatory regions for use in Yarrowia lipolytica). Any one of a number of regulatory sequences can be used, depending upon whether constitutive or induced transcription is desired, the efficiency of the promoter in expressing the ORF of interest, the ease of construction and the like.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and, 6.) the codon usage within the cloned gene, such that its frequency approaches the frequency of preferred codon usage of the host cell. Each of these types of modifications are encompassed in the present invention, as means to further optimize expression of the Δ5 desaturases described herein.

Transformation of Host Cells

Once the DNA encoding a polypeptide suitable for expression in an appropriate host cell has been obtained (e.g., a chimeric gene comprising a promoter, ORF and terminator), it is placed in a plasmid vector capable of autonomous replication in the host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell.

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in PCT Publications No. WO 2004/101757 and No. WO 2005/003310.

Following transformation, substrates suitable for the instant Δ5 desaturases (and, optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis

Knowledge of the sequences of the present Δ5 desaturases will be useful for manipulating ω-3 and/or ω-6 fatty acid biosynthesis in various host cells. This may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication No. WO 2006/055322 [U.S. Patent Publication No. 2006-0094092-A1], PCT Publication No. WO 2006/052870 [U.S. Patent Publication No. 2006-0115881-A1] and PCT Publication No. WO 2006/052871 [U.S. Patent Publication No. 2006-0110806-A1], respectively, as are desirable manipulations in the TAG biosynthetic pathway and the TAG degradation pathway (and associated techniques thereof).

Preferred Hosts for Recombinant Expression of Δ5 Desaturases

Host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention were initially isolated for expression in an oleaginous yeast (and in particular *Yarrowia lipolytica*); however, it is contemplated that because transcription, translation and the protein biosynthetic apparatus are highly conserved, any bacteria, yeast, algae, euglenoid and/or fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Specific teachings applicable for transformation of oleaginous yeasts (i.e., *Yarrowia lipolytica*) include U.S. Pat. No. 4,880,741 and U.S. Pat. No. 5,071,764 (incorporated herein by reference) and Chen, D. C. et al. (*Appl. Microbiol. Biotechnol.*, 48(2):232-235 (1997)). Specific teachings applicable for engineering ARA, EPA and DHA in *Y. lipolytica* are provided in U.S. patent application Ser. No. 11/264,784, Ser. No. 11/265,761 and Ser. No. 11/264,737, respectively. Detailed means for the synthesis and transformation of expression vectors comprising Δ5 desaturases in oleaginous yeast (i.e., *Yarrowia lipolytica*) are provided in PCT Publications No. WO 2004/101757 and No. WO 2006/052870. The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (GenBank Accession No. Z50020) and/or the Lip2 gene locus (GenBank Accession No. AJ012632)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast Ura⁻ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997).

Other preferred microbial hosts include oleaginous bacteria, algae, euglenoids and other fungi; and, within this broad group of microbial hosts, of particular interest are microorganisms that synthesize ω-3/ω-6 fatty acids. Thus, for example, transformation of *Mortierella alpina* (which is commercially used for production of ARA) with any of the present Δ5 desaturase genes under the control of inducible or regulated promoters could yield a transformant organism capable of synthesizing increased quantities of ARA. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

Irrespective of the host selected for expression of the Δ5 desaturases described herein, multiple transformants must be screened in order to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

Fermentation Processes for Omega Fatty Acid Production

The transformed host cell is grown under conditions that optimize expression of chimeric desaturase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in *Yarrowia lipolytica*. This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details.

Oils for Use in Foodstuffs, Health Food Products, Pharmaceuticals and Animal Feeds The market place currently supports a large variety of food and feed products, incorporating ω-3 and/or ω-6 fatty acids (particularly ARA, EPA and DHA). It is contemplated that the oils of the invention comprising long-chain PUFAs will function in food and feed products to impart the health benefits of current formulations. More specifically, oils of the invention containing ω-3 and/or ω-6 fatty acids will be suitable for use in a variety of food and feed products including, but not limited to: food analogs, meat products, cereal products, baked foods, snack foods and dairy products (see U.S. Patent Publication No. 2006/0094092 for details).

Additionally the present oils may be used in formulations to impart health benefits in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2nd ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol Biotechnol.*, 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G., and Nishida I., *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C/min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Euglena gracilis Growth Conditions, Lipid Profile and mRNA Isolation

Euglena gracilis was obtained from Dr. Richard Triemer's lab at Michigan State University (East Lansing, Mich.). From 10 mL of actively growing culture, a 1 mL aliquot was transferred into 250 mL of Euglena gracilis (Eg) Medium in a 500 mL glass bottle. Eg medium was made by combining 1 g of sodium acetate, 1 g of beef extract (Catalog #U126-01, Difco Laboratories, Detroit, Mich.), 2 g of Bacto® tryptone (Catalog #0123-17-3, Difco Laboratories) and 2 g of Bacto® yeast extract (Catalog #0127-17-9, Difco Laboratories) in 970 mL of water. After filter sterilizing, 30 mL of soil-water supernatant (Catalog #15-3790, Carolina Biological Supply Co., Burlington, N.C.) was aseptically added to give the final Eg medium. Euglena gracilis cultures were grown at 23° C. with a 16 h light, 8 h dark cycle for 2 weeks with no agitation.

Figure 2:
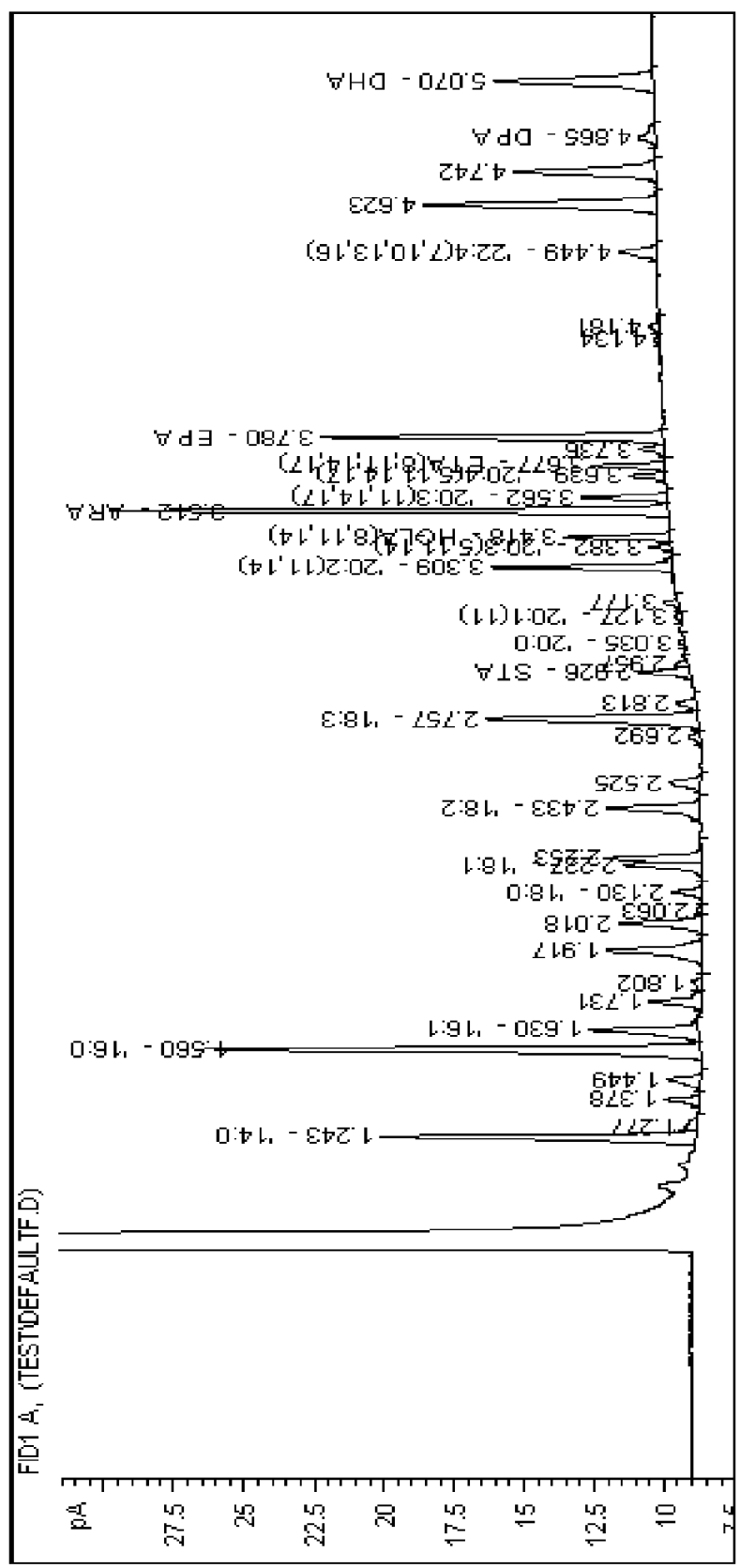
FIG. 2 shows a chromatogram of the lipid profile of an *Euglena gracilis* cell extract as described in Example 1.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 µL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 µL injected from hexane layer) were separated and quantified using a Hewlett-Packard 6890 Gas Chromatograph fitted with an Omegawax 320 fused silica capillary column (Catalog #24152, Supelco Inc., Bellefonte, Pa.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog #U-99-A, Nu-Chek Prep, Inc., Elysian, Minn.) and the resulting chromatogram is shown in FIG. 2.

The remaining 2 week culture (240 mL) was pelleted by centrifugation at 1,800×g for 10 min, washed once with water and re-centrifuged. Total RNA was extracted from the resulting pellet using the RNA STAT-60Tm reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 µg of mRNA was obtained.

Example 2

Euglena gracilis cDNA Synthesis cDNA was synthesized directly from the Euglena gracilis mRNA as follows. Specifically, the mRNA was primered with adapter primer AP (SEQ ID NO:65) from Invitrogen's 3'-RACE kit (Carlsbad, Calif.), in the presence of the Smart IV oligonucleotide (SEQ ID NO:66) from the BD-Clontech Creator™ Smart™ cDNA library kit (Mississauga, ON, Canada). The reverse transcription was done with Superscript II reverse transcriptase from the 3'-RACE kit according to the protocol of the Creator™ Smart™ cDNA library kit.

The 1$^{st}$ strand cDNA synthesis mixture was used as template for PCR amplification, using AP as the 3' primer and CDSIII 5' primer (SEQ ID NO:36) as the 5' primer (supplied with the BD-Clontech Creator™ Smart™ cDNA library kit).

Amplification was carried out with Clontech Advantage cDNA polymerase mix at 94° C. for 30 sec, followed by 20 cycles of 94° C. for 10 sec and 68° C. for 6 min. A final extension at 68° C. for 7 min was performed.

Example 3

Isolation of a Portion of the Coding Region of the Euglena gracilis Δ5 Desaturase Gene The present Example describes the identification of a portion of the Euglena gracilis gene encoding Δ5 desaturase (designated herein as "EgD5" (SEQ ID NOs:1 and 2)), by use of primers derived from conserved regions of other known Δ5 and Δ8 desaturase sequences.

Various considerations were made when evaluating which desaturases might enable design of degenerate primers suitable to isolate the Euglena gracilis Δ5 desaturase. Specifically, the Applicants knew that only Δ5, Δ6 and Δ8 desaturase sequences comprise a conserved 'HPGG' motif at their N-terminus (wherein the 'HPGG' domain is part of the well-known cytochrome B5 domain); in contrast, Δ9 desaturases possess a 'HPGG' motif of the cytochrome B5 domain at their C-terminus, while both Δ17 and Δ12 desaturases lack the cytochrome B5 domain. It was assumed that a Δ9 elongase/Δ8 desaturase pathway operated in Euglena gracilis; thus, among the desaturases sharing the N-terminal conserved 'HPGG' motif, only Δ5 and Δ8 desaturases were expected within the organism. Finally, although only a few Δ8 desaturase sequences are known, numerous Δ5 desaturase are publicly available. The Applicants selected those Δ5 desaturase sequences that possessed lower homology to "traditional" Δ5 desaturase genes and that also shared high homology to one another.

Based on the above, the four Δ5 desaturases and two Δ8 desaturases shown below in Table 3 were aligned, using the method of Clustal W (slow, accurate, Gonnet option; Thompson et al., Nucleic Acids Res., 22:4673-4680 (1994)) of the MegAlign™ program of DNASTAR software.

TABLE 3

Δ5 And Δ8 Desaturases Aligned To Identify Regions Of Conserved Amino Acids

| Desaturase | Organism | Reference | SEQ ID NO: |
|---|---|---|---|
| Δ5 | Pythium irregulare | GenBank Accession No. AAL13311 | 12 |
| Δ5 | Phytophthora megasperma | GenBank Accession No. CAD53323 | 13 |
| Δ5 | Phaeodactylum tricornutum | GenBank Accession No. AAL92562 | 14 |
| Δ5 | Dictyostelium discoideum | GenBank Accession No. XP_640331 | 15 |
| Δ8 | Euglena gracilis | PCT Publications No. WO 2006/012325 and No. WO 2006/012326 | 16 |
| Δ8 | Pavlova lutheri | Example 12 (infra) | 18 |

Figure 3:
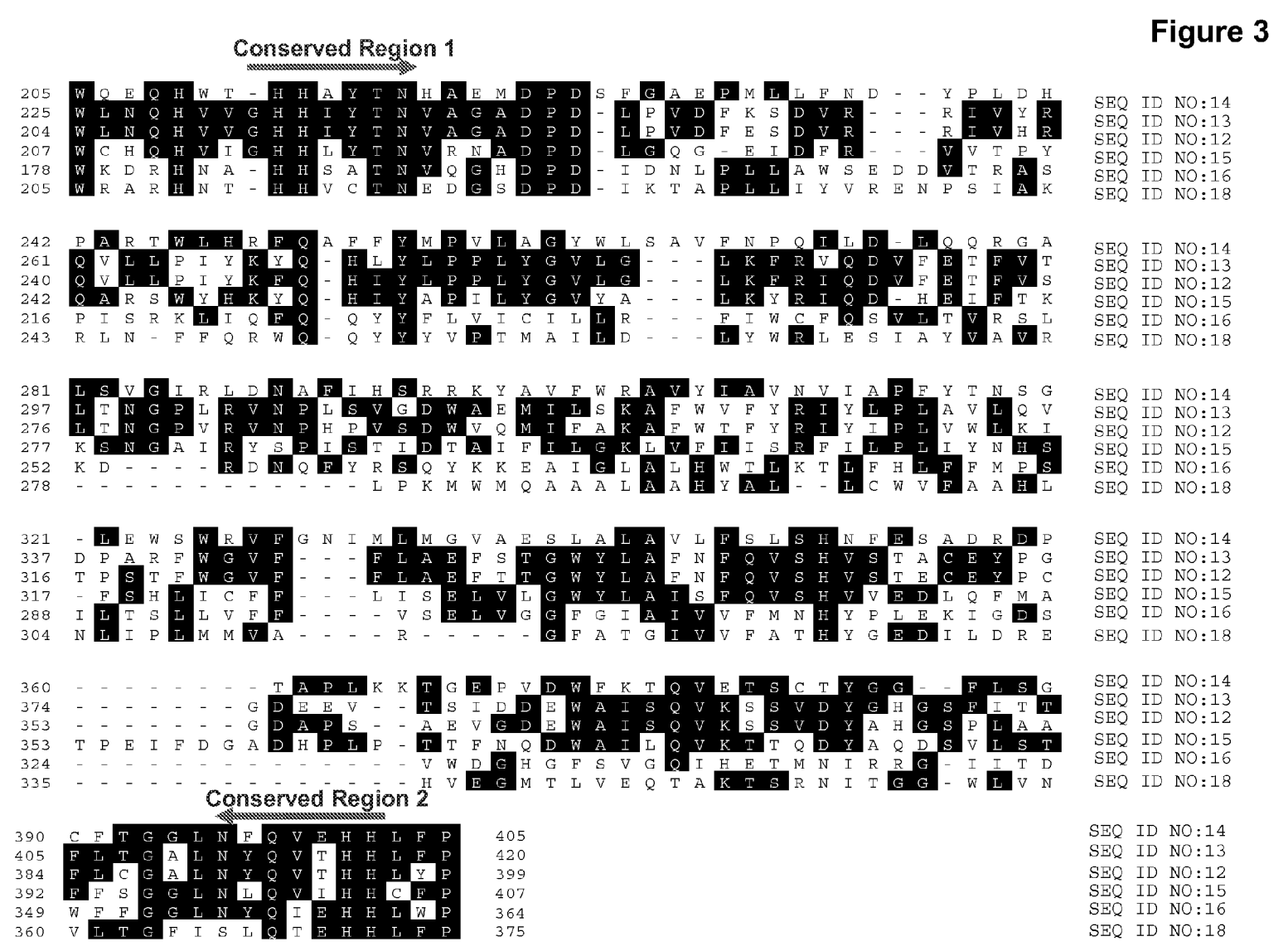

FIG. 3 shows a portion of the resulting alignment, containing several stretches of conserved amino acid sequence among the 6 different organisms. Based on this alignment, two sets of degenerate oligonucleotides were designed to amplify a portion of the coding region of the Δ5 desaturase gene from Euglena gracilis, corresponding to the regions of FIG. 3 that are labeled as "Conserved Region 1" and "Conserved Region 2". Specifically, the conserved amino acid sequence GHH(I/V)YTN (SEQ ID NO:19) was designed to correspond to Conserved Region 1, while the conserved amino acid sequence N(Y/F)Q(V/I)EHH (SEQ ID NO:20) was designed to correspond to Conserved Region 2. In order to reduce the degeneracy of the oligonucleotides, 4 sets of oligonucleotides (i.e., 5-1A, 5-1B, 5-1C and 5-1D) were designed to encode Conserved Region 1; and, 4 sets of oligonucleotides (i.e., 5-5AR, 5-5BR, 5-5CR and 5-5DR) were designed to encode the anti-sense strand of Conserved Region 2.

TABLE 4

Degenerate Oligonucleotides Used To Amplify
The Δ5 Desaturase Gene From *Euglena gracilis*

| Oligonucleotide Name | Sequence | SEQ ID NO |
|---|---|---|
| 5-1A | GGHCAYCAYRTBTAYACAAA | SEQ ID NO: 27 |
| 5-1B | GGHCAYCAYRTBTAYACCAA | SEQ ID NO: 28 |
| 5-1C | GGHCAYCAYRTBTAYACGAA | SEQ ID NO: 29 |
| 5-1D | GGHCAYCAYRTBTAYACTAA | SEQ ID NO: 30 |
| 5-5AR | TGRTGVACAAYYTGRWARTT | SEQ ID NO: 31 |
| 5-5BR | TGRTGVACTAYYTGRWARTT | SEQ ID NO: 32 |
| 5-5CR | TGRTGVACCAYYTGRWARTT | SEQ ID NO: 33 |
| 5-5DR | TGRTGVACGAYYTGRWARTT | SEQ ID NO: 34 |

[Note:
The nucleic acid degeneracy code used for SEQ ID NOs: 27 to 34 was as follows: R = A/G; Y = C/T; W = A/T; B = G/T/C; V = G/A/C; and H = A/C/T.]

Based on the full-length sequences of the Δ5 sequences of Table 3, it was hypothesized that the *Euglena gracilis* Δ5 gene fragment amplified as described above would be about 600 bp in length (lacking about 210 amino acids at its N-terminal and 70 amino acids at its C-terminal).

A total of sixteen different PCR amplifications were conducted, as all combinations of the primers were tested (i.e., primer 5-1A was used with each of 5-5AR, 5-5BR, 5-5CR and 5-5DR, individually; similarly, primer 5-1B was used with each of 5-5AR, 5-5BR, 5-5CR and 5-5DR; etc.). The PCR amplifications were carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer, 10 ng cDNA of *E. gracilis* and 1 µl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.). One fragment of the approximate expected size was then further purified following gel electrophoresis in 1% (w/v) agarose and then cloned into the pGEM-T-easy vector (Promega, Madison, Wis.). The ligated DNA was used to transform cells of *E. coli* DH10B and transformants were selected on LB (1% bacto-tryptone, 0.5% bacto-yeast extract and 1% NaCl) agar containing ampicillin (100 µg/mL). Analysis of the plasmid DNA from a group of 12 transformants confirmed the presence of the insert with the expected size (plasmids were designated as "pT-F10-1", "pT-F10-2", "pT-F10-3", etc. to "pT-F10-12").

Sequence analyses showed that pT-F10-1 contained a 590 bp fragment (SEQ ID NO:4), which encoded 196 amino acids (SEQ ID NO:5) (including amino acids that corresponded to Conserved Region 1 and 2). Identity of the *Euglena* sequence was determined by conducting BLAST (Basic Local Alignment Search Tool; Altschul, S. F., et al., *J. Mol. Biol.*, 215: 403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). SEQ ID NO:4 was compared for similarity to all publicly available protein sequences contained in the "nr" database, using the BLASTX algorithm (Gish, W. and States, D. J., *Nature Genetics*, 3:266-272 (1993)) provided by the NCBI.

The results of the BLASTX comparison summarizing the sequence to which SEQ ID NO:4 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the translated amino acid sequence of SEQ ID NO:4 (i.e., SEQ ID NO:5) had 38% identity and 53% similarity with the amino acid sequence of the Δ8-sphingolipid desaturase of *Thalassiosira pseudonana* (GenBank Accession No. AAX14502; SEQ ID NO:21), with an Expectation value of 5E-28; additionally, the partial fragment of SEQ ID NO:4 had 37% identity and 52% similarity with the Δ5 fatty acid desaturase of *Phaeodactylum tricornutum* (GenBank Accession No. AAL92562; SEQ ID NO:14), with an Expectation value of 7E-28.

Example 4

Isolation of the 5° Coding Region of the *Euglena gracilis* Δ5 Desaturase Gene

To isolate the N-terminal portion of the putative Δ5 desaturase identified in Example 3, a modified 5' RACE technique based on RACE protocols from two different companies (i.e., Invitrogen and BD-Clontech) was utilized.

Briefly, the double-stranded cDNA of *Euglena gracilis* (Example 2) was used as the template in a 5' RACE experiment, comprising two separate rounds of PCR amplification. In the first round of PCR amplification, the oligonucleotide primers consisted of a gene specific oligonucleotide (i.e., ODMW480; SEQ ID NO:35) and the generic oligonucleotide CDSIII 5' primer (SEQ ID NO:36) from the BD-Clontech Creator™ Smart™ cDNA library kit. The PCR amplifications were carried out in a 50 µl total volume, comprising: 25 µl of LA Taq™ pre-mix (TaKaRa Bio Inc., Otsu, Shiga, 520-2193, Japan), 10 pmole of each primer and 1 µl of Taq DNA polymerase (Epicentre Technologies, Madison, WI). The thermocycler conditions were set for 35 cycles at 95° C. for 1 min, 56° C. for 30 sec and 72° C. for 1 min, followed by a final extension at 72° C. for 10 min.

The second round of PCR amplification used 1 µl of the product from the first round PCR reaction as template. Primers consisted of a gene specific oligonucleotide (i.e., ODMW479; SEQ ID NO:37) and the generic oligonucleotide DNR CDS 5' (SEQ ID NO:38), supplied with BD-Clontech's Creator™ Smart™ cDNA library kit. Amplification was conducted as described above.

The products of the second round PCR reaction were electrophoresed in 1% (w/v) agarose. Products between 400 bp and 800 bp were then purified from the gel and cloned into the pGEM-T-easy vector (Promega, Madison, Wis.). The ligated DNA was used to transform *E. coli* DH10B and transformants were selected on LB agar containing ampicillin (100 µg/mL).

Analysis of the plasmid DNA from one transformant comprising the 5' region of the putative Δ5 desaturase gene confirmed the presence of the expected plasmid, designated pT-EgD5-5° C.2. Sequence analyses showed that pT-EgD5-5'C2 contained a fragment of 797 bp (SEQ ID NO:6), which over-lapped with 238 bp from the 5' end of the 590 bp fragment of pT-F10-1 (Example 3, SEQ ID NO:4) and additionally provided 559 bp of 5' upstream sequence (SEQ ID NO:7) (FIG. 4). The sequence of pT-EgD5-5'C2 also corrected the sequence corresponding to Conserved Region 1, resulting from use of a degenerate oligonucleotide for initial PCR amplification of the 590 bp fragment in pT-F10-1 (Example 3). However, there was no translation initiation codon in the extended 797 bp fragment of SEQ ID NO:6.

A second round of the modified 5' RACE was carried out as described above, except that oligonucleotides YL791 (SEQ ID NO:39) and YL792 (SEQ ID NO:40) were used as gene-specific primers. Products between 200 bp and 400 bp were then purified from a gel and cloned into the pGEM-T-easy vector (Promega, Madison, Wis.). The ligated DNA was transformed into *E. coli* DH10B and transformants were selected on LB agar containing ampicillin (100 µg/mL).

Analysis of the plasmid DNA from one transformant comprising the 5' region of the putative Δ5 desaturase gene confirmed the presence of the expected plasmid, designated pT-EgD5-5'2$^{nd}$. Sequence analyses showed that pT-EgD5-5'2$^{nd}$ contained a fragment of 273 bp (SEQ ID NO:8), which over-lapped with 253 bp of the 5' end of the DNA fragment in pT-EgD5-5'C2 described above and additionally provided 20 bp of 5' upstream sequence (SEQ ID NO:9). Seventeen (17) bp of the 20 bp encoded the N-terminal portion of the putative Δ5 desaturase gene, including the translation initiation codon, thus providing the complete 5' sequence of the gene.

Example 5

Isolation of the 3° Coding Region of the *Euglena gracilis* Δ5 Desaturase Gene

To isolate the C-terminal portion of the putative Δ5 desaturase identified in Example 3, a 3' RACE technique was utilized. The methodology was described above in Example 4; however, the primers used on both the first and second round of PCR amplification were as shown below in Table 5.

TABLE 5

Oligonucleotide Primers Used For 3' RACE

| PCR Amplification | Gene Specific Oligonucleotide | Generic Oligonucleotide |
|---|---|---|
| 1$^{st}$ Round | ODMW469 (SEQ ID NO: 41) | AUAP (SEQ ID NO: 42) |
| 2$^{nd}$ Round | YL470 (SEQ ID NO: 43) | AUAP (SEQ ID NO: 42) |

* Primer AUAP was supplied in Invitrogen's 3'-RACE kit (Carlsbad, CA)

Following isolation and purification of products (i.e., 400-800 bp), the fragments were cloned into the pGEM-T-easy vector (Promega) and transformed into *E. coli* DH10B, as in Example 4.

Analysis of the plasmid DNA from one transformant comprising the 3' region of the Δ5 desaturase gene confirmed the presence of the expected plasmid, designated pT-EgD5-3'. Sequence analyses showed that pT-EgD5-3' contained a fragment of 728 bp (SEQ ID NO:10), which over-lapped with 264 bp from the 3' end of the 590 bp fragment of pT-F10-1 (Example 3, SEQ ID NO:4) and provided 464 bp of additional 3' downstream sequence (SEQ ID NO:11). The first 184 bp of the 464 bp fragment included within pT-EgD5-3' encoded the C-terminal coding region (including the translation stop codon) of the putative Δ5 desaturase gene. The sequence of pT-EgD5-3' also corrected the sequence corresponding to Conserved Region 2, resulting from use of a degenerate oligonucleotide for initial PCR amplification of the 590 bp fragment in pT-F10-1 (Example 3).

After 2 rounds of 5' RACE and one round of 3' RACE, the DNA sequence of the entire putative *Euglena gracilis* Δ5 desaturase (EgD5) coding region was determined. As shown in FIG. 4, the EgD5 CDS was 1350 bp in length (SEQ ID NO:1) and encoded a polypeptide with 449 amino acids (SEQ ID NO:2), based on alignment of SEQ ID NOs:4, 6, 8 and 10. The results of BLASTP searches using the full length EgD5 gene as the query sequence showed that it shared 39% identity and 56% similarity with the Δ5 fatty acid desaturase of Phaeodactylum tricornutum (GenBank Accession No. AAL92562; SEQ ID NO:14), with an Expectation value of 1E-80. Additionally, the full length EgD5 gene shared 37% identity and 55% similarity with the Δ8-sphingolipid desaturase of *Thalassiosira pseudonana* (GenBank Accession No. AAX14502; SEQ ID NO:21), with an Expectation value of 3E-75.

Example 6

Generation of Construct pDMW367, Comprising EgD5

The present Example describes the generation of pDMW367, comprising a chimeric FBAIN::EgD5::Pex20-3' gene (FIG. 5C). This was designed to integrate the chimeric gene into the genome of *Yarrowia lipolytica* and then study the function of the *Euglena gracilis* Δ5 desaturase in *Yarrowia lipolytica*.

Based on the full length cDNA of EgD5 (SEQ ID NO:1), oligonucleotides YL794 and YL797 (SEQ ID NOs:44 and 45, respectively) were used as primers to amplify the first portion of EgD5 (FIG. 5A). Primer YL794 contained a NcoI site and primer YL797 contained a HindIII site. Then, primers YL796 and YL795 (SEQ ID NOs:46 and 47, respectively) were used as primers to amplify the second portion of EgD5. Primer YL796 contained a HindIII site, while primer YL797 contained a NotI site. The PCR reactions, using primer pairs YL794/YL797 or YL796NYL795, with *Euglena gracilis* cDNA (Example 2) as template, were individually carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 72° C. for 10 min.

The individual PCR products were purified using a Qiagen PCR purification kit. The PCR products from the reaction amplified with primers YL794NYL797 were digested with NcoI and HindIII, while the PCR products from the reaction amplified with primers YL796/YL795 were digested with HindIII and NotI. The NcoI/HindIII- and the HindIII/NotI-digested DNA fragments were purified following gel electrophoresis in 1% (w/v) agarose, and then directionally ligated with NcoI/NotI-digested pZUF17 (FIG. 5B; SEQ ID NO:22; comprising a synthetic Δ17 desaturase gene ["D17st"] derived from *Saprolegnia diclina* (U.S. Patent Publication No. 2003/0196217 A1), codon-optimized for expression in *Yarrowia lipolytica* (PCT Publication No. WO 2004/101757)). The product of this ligation was pDMW367 (FIG. 5C; SEQ ID NO:23), which thereby contained the following components:

TABLE 6

Components Of Plasmid pDMW367 (SEQ ID NO: 23)

| RE Sites And Nucleotides Within SEQ ID NO: 23 | Description Of Fragment And Chimeric Gene Components |
|---|---|
| EcoR I/BsiW I (7416-1671) | FBAIN::EgD5::Pex20, comprising: FBAIN: *Yarrowia lipolytica* FBAIN promoter (PCT Publication No. WO 2005/049805; U.S. Pat. No. 7,202,356) EgD5: *Euglena gracilis* Δ5 desaturase (SEQ ID NO: 1 described herein; labeled as "*Euglena* D5DS" in Figure) Pex20: Pex20 terminator sequence of *Yarrowia* Pex20 gene (GenBank Accession No. AF054613) |
| 2707-1827 | ColE1 plasmid origin of replication |
| 3637-2777 | ampicillin-resistance gene (Amp$^R$) for selection in *E. coli* |
| 4536-5840 | *Yarrowia* autonomous replication sequence (ARS18; GenBank Accession No. A17608) |
| 7373-5886 | *Yarrowia* Ura 3 gene (GenBank Accession No. AJ306421) |

The term "FBAIN promoter" or "FBAIN promoter region" refers to the 5' upstream untranslated region in front of the 'ATG' translation initiation codon of the *Yarrowia lipolytica* fructose-bisphosphate aldolase enzyme (E.C. 4.1.2.13) encoded by the fba1 gene and that is necessary for expression, plus a portion of 5' coding region that has an intron of the fba1 gene.

Example 7

Generation of *Yarrowia lipolytica* Strain M4 to Produce About 8% DGLA of Total Lipids The present Example describes the construction of strain M4, derived from *Yarrowia lipolytica* ATCC #20362, capable of producing 8% DGLA relative to the total lipids. This strain was engineered to express the Δ6 desaturase/Δ6 elongase pathway, via introduction of construct pKUNF12T6E (FIG. 6A; SEQ ID NO:24). This construct was generated to integrate four chimeric genes (comprising a Δ12 desaturase, a Δ6 desaturase and two $C_{18/20}$ elongases) into the Ura3 loci of wild type *Yarrowia* strain ATCC #20362, to thereby enable production of DGLA. Thus, pKUNF12T6E contained the following components:

TABLE 7

Description of Plasmid pKUNF12T6E (SEQ ID NO: 24)

| RE Sites And Nucleotides Within SEQ ID NO: 24 | Description Of Fragment And Chimeric Gene Components |
|---|---|
| AscI/BsiWI (9420-8629) | 784 bp 5' portion of *Yarrowia* Ura3 gene (GenBank Accession No. AJ306421) |
| SphI/PacI (12128-1) | 516 bp 3' portion of *Yarrowia* Ura3 gene (GenBank Accession No. AJ306421) |
| SwaI/BsiWI (6380-8629) | FBAIN::EL1S::Pex20, comprising: FBAIN: *Yarrowia lipolytica* FBAIN promoter (PCT Publication No. WO 2005/049805; U.S. Pat. No. 7,202,356; labeled as "Fba1 + intron" in Figure) EL1S: codon-optimized elongase 1 gene (PCT Publication No. WO 2004/101753), derived from *Mortierella alpina* (GenBank Accession No. AX464731) Pex20: Pex20 terminator sequence from *Yarrowia* Pex20 gene (GenBank Accession No. AF054613) |
| BglII/SwaI (4221-6380) | TEF::Δ6S::Lip1, comprising: TEF: *Yarrowia lipolytica* TEF promoter (GenBank Accession No. AF054508) Δ6S: codon-optimized Δ6 desaturase gene (PCT Publication No. WO 2004/101753), derived from *Mortierella alpina* (GenBank Accession No. AF465281) Lip1: Lip1 terminator sequence from *Yarrowia* Lip1 gene (GenBank Accession No. Z50020) |
| PmeI/ClaI (4207-1459) | FBA::F.Δ12::Lip2, comprising: FBA: *Yarrowia lipolytica* FBA promoter (PCT Publication No. WO 2005/049805; U.S. Pat. No. 7,202,356; labeled as "FBA1" in Figure) F.Δ12: *Fusarium moniliforme* Δ12 desaturase gene (PCT Publication No. WO 2005/047485) Lip2: Lip2 terminator sequence from *Yarrowia* Lip2 gene (GenBank Accession No. AJ012632) |
| ClaI/PacI (1459-1) | TEF::EL2Syn::XPR2, comprising: TEF: *Yarrowia lipolytica* TEF promoter (GenBank Accession No. AF054508) EL2Syn: codon-optimized elongase gene (SEQ ID NO: 25), derived from *Thraustochytrium aureum* (U.S. Pat. No. 6,677,145) XPR2: ~100 bp of the 3' region of the *Yarrowia* Xpr gene (GenBank Accession No. M17741) |

Plasmid pKUNF12T6E was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura– strains. Single colonies of Ura– strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E, but not in the wild type *Yarrowia* control strain. Most of the selected 32 Ura⁻ strains produced about 6% DGLA of total lipids. There were 2 strains (i.e., strains M4 and 13-8) that produced about 8% DGLA of total lipids.

Example 8

Functional Analysis of EgD5 Gene in *Yarrowia lipolytica* Strain M4

Plasmid pDMW367 (Example 6; comprising a chimeric FBAIN::EgD5::Pex20 gene was transformed into strain M4

(Example 7), as described in the General Methods. The transformants were selected on MM plates. After 2 days grown at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 5.6% DGLA and 2.8% ARA of total lipids produced in all three transformants, wherein the conversion efficiency of DGLA to ARA in these three strains was determined to be about 33% (average). The conversion efficiency was measured according to the following formula: ([product]/[substrate+product])*100, where 'product' includes the immediate product and all products in the pathway derived from it. Thus, this experimental data demonstrated that the cloned *Euglena gracilis* Δ5 desaturase, described herein as SEQ ID NOs:1 and 2, efficiently desaturated DGLA to ARA.

Example 9

Synthesis of a Codon-Optimized Δ5 Desaturase Gene ("EqD5S") for Expression in *Yarrowia lipolytica*

The codon usage of the Δ5 desaturase gene of *Euglena gracilis* (SEQ ID NOs:1 and 2; EgD5) was optimized for expression in *Yarrowia lipolytica*, in a manner similar to that described in PCT Publication No. WO 2004/101753 and U.S. Pat. No. 7,125,672. Specifically, a codon-optimized Δ5 desaturase gene (designated "EgD5S", SEQ ID NO:3) was designed based on the coding sequence of the Δ5 desaturase gene of EgD5, according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene*, 265(1-2):11-23 (2001)). In addition to modification of the translation initiation site, 196 bp of the 1350 bp coding region were modified (14.5%; FIG. 7) and 189 codons were optimized (42%). The GC content was reduced from 55.5% within the wild type gene (i.e., EgD5) to 54.4% within the synthetic gene (i.e., EgD5S). A NcoI site and NotI sites were incorporated around the translation initiation codon and after the stop codon of EgD5S, respectively. None of the modifications in the codon-optimized gene changed the amino acid sequence of the encoded protein (SEQ ID NO:2). The designed EgD5S gene (SEQ ID NO:3) was synthesized by GenScript Corporation (Piscataway, N.J.) and cloned into pUC57 (GenBank Accession No. Y14837) to generate pEgD5S (FIG. 6B; SEQ ID NO:48).

Example 10

Generation of Construct pDMW369, Comprising EqD5S

The present Example describes the construction of plasmid pDMW369 comprising a chimeric FBAIN::EgD5S::Pex20 gene. Plasmid pDMW369 (FIG. 6C; SEQ ID NO:49) was constructed by replacing the Nco I/NotI fragment of pZUF17 (FIG. 5B; SEQ ID NO:22) with the Nco I/Not I EgD5S fragment from pEgD5S (FIG. 6B; SEQ ID NO:48). The product of this ligation was pDMW369, which thereby contained the following components:

TABLE 8

Components Of Plasmid pDMW369 (SEQ ID NO: 49)

| RE Sites And Nucleotides Within SEQ ID NO: 49 | Description Of Fragment And Chimeric Gene Components |
|---|---|
| EcoR I/BsiW I (6063-318) | FBAIN::EgD5S::Pex20, comprising: FBAIN: *Yarrowia lipolytica* FBAIN promoter (PCT Publication No. WO 2005/049805; U.S. Pat. No. 7,202,356; labeled as "FBA1 + Intron" in Figure) EgD5S: codon-optimized Δ5 desaturase (SEQ ID NO: 3, described herein as EgD5S), derived from *Euglena gracilis* Pex20: Pex20 terminator sequence of *Yarrowia* Pex20 gene (GenBank Accession No. AF054613) |
| 1354-474 | ColE1 plasmid origin of replication |
| 2284-1424 | ampicillin-resistance gene (Amp$^R$) for selection in *E. coli* |
| 3183-4476 | *Yarrowia* autonomous replication sequence (ARS18; GenBank Accession No. A17608) |
| 6020-4533 | *Yarrowia* Ura 3 gene (GenBank Accession No. AJ306421) |

Example 11

Expression of the Codon-Optimized Δ5 Desaturase ("EqD5S") in *Yarrowia lipolytica* Strain M4

Plasmid pDMW369 (Example 10; comprising a chimeric FBAIN::EgD5S::Pex20 gene) was transformed into strain M4 (Example 7), as described in the General Methods. The transformants were selected on MM plates. After 2 days growth at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 3.3% DGLA and 2.7% ARA of total lipids produced in all three transformants, wherein the conversion efficiency of DGLA to ARA in these three strains was determined to be about 45% (average; calculated as described in Example 8). Thus, this experimental data demonstrated that the synthetic *Euglena gracilis* Δ5 desaturase codon-optimized for expression in *Yarrowia lipolytica* (EgD5S, as set forth in SEQ ID NO:3) is about 36% more efficient desaturating DGLA to ARA than the wild type EgD5 gene (SEQ ID NO:1).

Example 12

Isolation of a *Pavlova lutheri* (CCMP459) Δ8 Desaturase

The present example describes the isolation of the *Pavlova lutheri* (CCMP459) Δ8 desaturase utilized in Example 3 and in FIG. 3 (also described in U.S. patent application Ser. No. 11/737,772 incorporated herein by reference) This required: synthesis of *Pavlova lutheri* (CCMP459) cDNA; library construction and sequencing; identification of Δ8 desaturase homologs; and, cloning of a full-length Δ8 desaturase from genomic DNA.

*Pavlova lutheri* (CCMP459) cDNA Synthesis, Library Construction and Sequencing

A cDNA library of *Pavlova lutheri* (CCMP459) was synthesized as described in PCT Publication No. WO 2004/071467 (published Aug. 26, 2004). Briefly, frozen pellets of Pav459 were obtained from the Provasoli-Guillard National Center for Culture of Marine Phytoplankton (CCMP, West Boothbay Harbor, Me.). These pellets were crushed in liquid nitrogen and total RNA was extracted from Pav459 by using the Qiagen RNeasy® Maxi Kit (Qiagen, Valencia, Calif.), per the manufacturer's instructions. From this total RNA, mRNA was isolated using oligo dT cellulose resin, which was then used for the construction of a cDNA library using the pSport1 vector (Invitrogen, Carlsbad, Calif.). The cDNA thus produced was directionally cloned (5' SalI/3' NotI) into pSport1 vector. The Pav459 library contained approximately $6.1 \times 10^5$ clones per mL, each with an average insert size of approximately 1200 bp. The *Pavlova lutheri* library was named eps1c.

For sequencing, clones first were recovered from archived glycerol cultures grown/frozen in 384-well freezing media plates, and inoculated with an automatic QPix® colony picker (Genetix) in 96-well deep-well plates containing LB+100 mg/mL ampicillin. After growing 20 hrs at 37° C., cells were pelleted by centrifugation and stored at −20° C. Plasmids then were isolated on an Eppendorf 5Prime robot, using a modified 96-well format alkaline lysis miniprep method (Eppendorf PerfectPrep®). Briefly, a filter and vacuum manifold was used to facilitate removal of cellular debris after acetate precipitation. Plasmid DNA was then bound on a second filter plate directly from the filtrate, washed, dried and eluted.

Plasmids were end-sequenced in 384-well plates, using vector-primed T7 primer (SEQ ID NO:50) and the ABI Big-Dye version 3 Prism sequencing kit. For the sequencing reaction, 100-200 ng of template and 6.4 pmoL of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

Identification of Δ8 Desaturase Enzyme Homologs from *Pavlova lutheri* cDNA Library eps1c cDNA clones encoding *Pavlova lutheri* Δ8 desaturase homologs (hereby called Δ8 desaturases) were identified by conducting BLAST searches for similarity to sequences contained in the BLAST "nr" database (as described in Example 3). The P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone eps1c.pk002.f22 revealed similarity of the protein encoded by the cDNA to the Δ6 desaturase from *Rhizopus stolonifer* (SEQ ID NO:51) (NCBI Accession No. AAX22052 (GI 60499699), locus AAX22052, CDS AY795076; Lu et al., unpublished). The sequence of a portion of the cDNA insert from clone eps1c.pk002.f22 is shown in SEQ ID NO:52 (5' end of cDNA insert). Subsequently, the full insert sequence (eps1c.pk002.f22:fis) was obtained and is shown in SEQ ID NO:53. Sequence for the deduced amino acid sequence (from nucleotide 1 of SEQ ID NO:53 to the first stop codon at nucleotide 864 of SEQ ID NO:53) is shown in SEQ ID NO:54. Full insert sequencing was carried out using a modified transposition protocol. Clones identified for full insert sequencing were recovered from archived glycerol stocks as single colonies, and plasmid DNA was isolated via alkaline lysis. Plasmid templates were transposed via the Template Generation System (TGS II) transposition kit (Finnzymes Oy, Espoo, Finland), following the manufacturer's protocol. The transposed DNA was transformed into EH10B electro-competent cells (Edge BioSystems, Gaithersburg, Md.) via electroporation. Multiple transformants were randomly selected from each transposition reaction, plasmid DNA was prepared, and templates were sequenced as above (ABI BigDye v3.1) outward from the transposition event site, utilizing unique primers SeqE (SEQ ID NO:55) and SeqW (SEQ ID NO:56).

Sequence data was collected (ABI Prism Collections software) and assembled using the Phrap sequence assembly program (P. Green, University of Washington, Seattle). Assemblies were viewed by the Consed sequence editor (D. Gordon, University of Washington, Seattle) for final editing.

The amino acid sequence set forth in SEQ ID NO:54 was evaluated by BLASTP, yielding a pLog value of 19.52 (E value of 3e-20) versus the Δ6 desaturase from *Mortierella alpina* (NCBI Accession No. BAC82361 (GI 34221934), locus BAC82361, CDS AB070557; Sakuradani and Shimizu, *Biosci. Biotechnol. Biochem.*, 67:704-711 (2003)). Based on the results from the BLASTP comparison to the *Mortierella alpina* and other fatty acid desaturases, the *Pavlova lutheri* Δ8 desaturase was not full length and was lacking sequence at the 5' end.

Cloning A Full-Length Δ8 Desaturase from *Pavlova lutheri* Genomic DNA

Genomic DNA was isolated from *Pavlova lutheri* (CCMP459) using the Qiagen DNeasy® Plant Maxi Prep Kit according to the manufacturer's protocol. Using 1 maxi column per 1 gm of frozen cell pellet, a total of 122 μg of genomic DNA was isolated from 4 gm of *Pavlova lutheri* culture. The final concentration of genomic DNA was 22.8 ng/μL. GenomeWalker libraries were synthesized using the Universal GenomeWalker™ kit (BD Biosciences Clonetech, Palo Alto, Calif.) following the manufacturer's protocol (Prot # PT3042-1, version PRO3300). Briefly, four restriction digests were set up as per the protocol using 300 ng of genomic DNA per reaction. After phenol clean up, pellets were dissolved in 4 μL of water and adapters were ligated as per the protocol.

For the primary PCR, the Advantage®-GC Genomic PCR kit (BD Biosciences Clonetech) was used following the manufacturer's protocol (Prot # PT3090-1, version PR1X433). For each restriction digest, 1 μL of library was combined with 22.8 μL of PCR grade water, 10 μL of 5×GC Genomic PCR Reaction Buffer, 2.2 μL of 25 mM Mg(CH$_3$CO$_2$)$_2$, 10 μL of GC-Melt (5 M), 1 μL of 50× dNTP mix (10 mM each), 1 μL of Advantage-GC Genomic Pol. Mix (50×), 1 μL of Universal GenomeWalker™ primer AP1 (10 μM, SEQ ID NO:57) and 1 μL of GSP PvDES (10 μM, SEQ ID NO:58). After denaturation at 95° C., the following reaction conditions were repeated 35 times: 94° C. for 30 sec, 68° C. for 6 min. After these reaction conditions, an additional extension at 68° C. was carried out for 6 min followed by cooling to 15° C. until removed.

The primary PCR reaction for each library was analyzed by agarose gel electrophoresis and DNA bands with molecular weights around 6 kB, 3.5 kB, 2.5 kB and 1.2 kB were observed. DNA bands for each library were purified using the Zymoclean™ Gel DNA Recovery Kit (Zymo Research, Orange, Calif.) following the manufacturer's protocol. The resulting DNA was cloned into the PGEM®-T Easy Vector (Promega) following the manufacturer's protocol and inserts were sequenced using the T7 (SEQ ID NO:50) and M13-28Rev (SEQ ID NO:59) primers as described above. Additional sequence was then obtained using a gene-specific sequencing primer PavDES seq (SEQ ID NO:60) that was derived from the newly acquired sequence data. The full 5' end sequence obtained by genome walking is shown in SEQ ID NO:61. The sequence of the overlapping regions of the genomic sequence (SEQ ID NO:61) and the fully sequenced EST eps1c.pk002.f22:fis (SEQ ID NO:53) were aligned using Sequencher™ (Version 4.2, Gene Codes Corporation, Ann Arbor, Mich.) using the Large Gap assembly algorithm. Interestingly, the comparison showed that the EST that was originally sequenced (SEQ ID NO:53) was lacking 459 bp when compared to the genomic sequence (SEQ ID NO:61). This missing sequence in the EST appeared to be a deletion rather than an intron as no clear intron splice sites were identified in the genomic DNA at the 5' end of the gene. The genomic sequence for the 5' end (SEQ ID NO:61) was combined with the 3' end of the EST sequence (SEQ ID NO:53) to yield SEQ ID NO:62. Using EditSeq™ 6.1 sequence analysis software (DNASTAR Inc., Madison, Wis.), an ORF was identified (SEQ ID NO:17). The amino acid sequence coded for by SEQ ID NO:17 is shown in SEQ ID NO:18.

The amino acid sequence set forth in SEQ ID NO:18 was evaluated by BLASTP, yielding a pLog value of 35.10 (E value of 8e-36) versus the Δ6 desaturase from *Rhizopus stolonifer* (SEQ ID NO:63) (NCBI Accession No. ABB96724 (GI 83027409), locus ABB96724, CDS DQ291156; Zhang et al., unpublished). Furthermore, the *Pavlova lutheri* Δ8 desaturase is 78.0% identical to the *Pavlova salina* Δ8 desaturase sequence (SEQ ID NO:64) disclosed in PCT Publication No. WO 2005/103253 (published Apr. 22, 2005) using the Jotun Hein method. Sequence percent identity calculations performed by the Jotun Hein method (Hein, J. J., *Meth. Enz.,* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). The *Pavlova lutheri* Δ8 desaturase is 76.4% identical to the *Pavlova salina* Δ8 desaturase sequence using the Clustal V method. Sequence percent identity calculations performed by the Clustal V method (Higgins, D. G. and Sharp, P. M., *Comput. Appl. Biosci,.* 5:151-153 (1989); Higgins et al., *Comput. Appl. Biosci.,* 8:189-191 (1992)) were done using the MegAlign™ v6.1 program of the LASERGENE bioinformatics computing suite (DNASTAR Inc.) with the default parameters for pairwise alignment (KTUPLE=1, GAP PENALTY=3, WINDOW=5, DIAGONALS SAVED=5 and GAP LENGTH PENALTY=10). BLAST scores and probabilities indicate that the fragment of SEQ ID NO:17 encodes an entire *Pavlova lutheri* Δ8 desaturase.

FIGS. 8A and 8B show a Clustal V alignment (with default parameters) of SEQ ID NO:18 (the amino acid sequence of the *Pavlova lutheri* Δ8 desaturase), SEQ ID NO:64 (the amino acid sequence of *Pavlova salina* Δ8 desaturase sequence, supra), SEQ ID NO:16 (the amino acid sequence of *Euglena gracilis* Δ8 desaturase sequence disclosed as SEQ ID NO:2 in PCT Publication No. WO 2006/012325; published Feb. 2, 2006), SEQ ID NO:63 (the amino acid sequence for the *Rhizopus stolonifer* Δ6 fatty acid desaturase (NCBI Accession No. ABB96724, supra)) and SEQ ID NO:51 (the amino acid sequence for the *Rhizopus stolonifer* Δ6 fatty acid desaturase (NCBI Accession No. AAX22052, supra)). The results of the Clustal V alignment show that SEQ ID NO:18 is 76.4%, 22.6%, 22.2% and 22.2% identical to SEQ ID NO:64, SEQ ID NO:16, SEQ ID NO:63 and SEQ ID NO:51, respectively.

Example 13

Comparing the Substrate Specificity of the *Mortierella alpina* Δ5 Desaturase (MaD5) with the *Euglena gracilis* Δ5 Desaturase (EgD5) in *Yarrowia lipolytica*

The present Example describes comparison of the substrate specificity of a *Mortierella alpina* Δ5 desaturase (MaD5; SEQ ID NOs:67 and 68), which is described in U.S. Pat. No. 6,075,183 and PCT Publications No. WO 2004/071467 and No. WO 2005/047479) to that of EgD5 (SEQ ID NO:2) in *Yarrowia lipolytica*.

This work included the following steps: (1) construction of Yarrowia expression vector pY98 comprising MaD5; (2) transformation of pY98 and pDMW367 into *Yarrowia* strain Y2224; and, 3.) comparison of lipid profiles within transformant organisms comprising pY98 or pDMW367 after feeding fatty acid substrates.

Construction of *Yarrowia* Expression Vector pY98, Comprising MaD5

Plasmid pY5-22 (SEQ ID NO:69) is a shuttle plasmid that can replicate both in *E. coli* and *Yarrowia lipolytica*, containing the following: a *Yarrowia* autonomous replication sequence (ARS18; GenBank Accession No. M91600); a ColE1 plasmid origin of replication; an ampicillin-resistance gene (Amp$^R$) for selection in *E. coli*; a *Yarrowia* URA3 gene (GenBank Accession No. AJ306421) for selection in *Yarrowia*; and, a chimeric TEF::NcoI/NotI::XPR cassette, wherein "XPR" was ~100 bp of the 3' region of the *Yarrowia* Xpr gene (GenBank Accession No. M17741). Although the construction of plasmid pY5-22 is not described herein in detail, it was derived from pY5 (previously described in PCT Publication No. WO 2004/101757).

Plasmid pY5-22GPD (SEQ ID NO:70) was created from pY5-22 (SEQ ID NO:69), by replacing the TEF promoter with the *Yarrowia lipolytica* GPD promoter (SEQ ID NO:71) using techniques well known to one skilled in the art. The *Yarrowia* "GPD promoter" refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (PCT Publication No. WO 2005/003310). More specifically, the *Yarrowia lipolytica* GPD promoter was amplified from plasmid pYZDE2-S (SEQ ID NO:72; which was previously described in U.S. Patent Application No. 60/795,810 (the contents of which are hereby incorporated by reference)) using oligonucleotides GPD-sense (SEQ ID NO:73) and GPDantisense (SEQ ID NO:74). The resulting DNA fragment was digested with SalI/NotI and cloned into the SalI/NotI fragment of pY5-22 (SEQ ID NO:69), thus replacing the TEF promoter and NcoI/NotI site with the GPD promoter and a unique NotI site, and thereby producing pY5-22GPD (SEQ ID NO:70).

The *Mortierella alpina* Δ5 desaturase gene (SEQ ID NO:67) was released from pKR136 (SEQ ID NO:75; which was previously described in PCT Publication No. WO 2004/071467 (the contents of which are hereby incorporated by reference)) by digestion with NotI and cloned into the NotI site of pY5-22GPD to produce pY98 (SEQ ID NO:76; FIG. 9).

Transformation of FY98 (Comprising MaD5) and pDMW367 (Comprising EgD5) into *Yarrowia* Strain Y2224 and Comparison of Lipid Profiles Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY98 (SEQ ID NO:76, FIG. 9) and pDMW367 (SEQ ID NO:23; FIG. 5C; Example 6) as described in the General Methods.

Single colonies of transformant *Yarrowia lipolytica* containing pY98 (SEQ ID NO:76) or pDMW367 (SEQ ID NO:23) were grown in 3 mL MM lacking uracil supplemented with 0.2% tergitol at 30° C. for 1 day. After this, 0.1 mL was transferred to 3 mL of the same medium supplemented with either EDA, ETrA, DGLA, ETA or no fatty acid. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.*, 276(1):38-46 (1990)) with 500 µL of 1% sodium methoxide for 30 min at 50° C. after which 500 µL of 1M NaCl and 100 µL of heptane were added. After thorough mixing and centrifugation, fatty acid methyl esters (FAMEs) were analyzed by GC.

FAMEs (5 µL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for *Yarrowia lipolytica* expressing pY98 (SEQ ID NO:76) or pDMW367 (SEQ ID NO:23) and fed various substrates are shown in FIG. 10A. In FIG. 10A shading indicates the substrates fed and products produced; fatty acids are identified as 16:0 (palmitate), 16:1, 18:0 (stearic acid), 18:1 (oleic acid), LA, GLA, ALA, STA, EDA, SCI (sciadonic acid or cis-5,11,14-eicosatrienoic acid; 20:3 ω-6), DGLA, ARA, ETrA, JUP (juniperonic acid or cis-5,11, 14,17-eicosatrienoic acid; 20:4 ω-3), ETA and EPA. Fatty acid compositions were expressed as the weight percent (wt. %) of total fatty acids.

Percent Δ5 desaturation ("% delta-5 desat") of EgD5 and MaD5 for each substrate is shown in FIG. 10B and was calculated by dividing the wt. % for product (either SCI, JUP, ARA or EPA) by the sum of the wt. % for the substrate and product (either EDA and SCI, ETrA and JUP, DGLA and ARA, or ETA and EPA, respectively) and multiplying by 100 to express as a %, depending on which substrate was fed.

The activities of EgD5 and MaD5 are compared using the ratio of the percent Δ5 desaturation ("Ratio Desat Eg/Ma") in FIG. 10B and are calculated by dividing the percent Δ5 desaturation for EgD5 on a particular substrate by the percent Δ5 desaturation for MaD5 on the same substrate.

The substrate specificity of EgD5 and MaD5 for the correct ω-6 fatty acid substrate (i.e., DGLA) versus the by-product fatty acid (i.e., SCI) or the correct ω-3 fatty acid substrate (i.e., ETA) versus the by-product fatty acid (i.e., JUP) is also shown in FIG. 10B. Specifically, the substrate specificity ("Ratio Prod/By-Prod") for ω-6 substrates was calculated by dividing the percent Δ5 desaturation (% delta-5 desat) for DGLA by the percent Δ5 desaturation (% delta-5 desat) for EDA and is shown on the same lines as the results for DGLA. The substrate specificity ("Ratio Prod/By-Prod") for ω-3 substrates was calculated by dividing the percent Δ5 desaturation (% delta-5 desat) for ETA by the percent Δ5 desaturation (% delta-5 desat) for ETrA and is shown on the same lines as the results for ETA. Furthermore, the ratio of substrate specificity ("Ratio Prod/By-Prod Eg/Ma") for ω-6 substrates was determined by dividing the substrate specificity for EgD5 on the ω-6 substrates (i.e., DGLA/EDA) by that for MaD5. The ratio of substrate specificity ("Ratio Prod/By-Prod Eg/Ma") for ω-3 substrates was calculated by dividing the substrate specificity for EgD5 on the ω-3 substrates (i.e., ETA/ETrA) by that for MaD5.

The preference of EgD5 and MaD5 for ω-6 or ω-3 substrates is compared using the ratio of the percent Δ5 desaturation ("Ratio n-6/n-3") in FIG. 10B and is calculated by dividing the percent Δ5 desaturation for EgD5 and MaD5 on a particular ω-6 substrate (either DGLA or EDA) by the percent Δ5 desaturation on the corresponding ω-3 substrate (either ETA or ETrA, respectively).

From the results in FIG. 10B, it is clear that EgD5 is approximately 2.6- to 2.9-fold more active in *Yarrowia* than MaD5 when DGLA, EDA and ETA are used as substrates. The exception is the activity for ETrA which is approximately the same for both enzymes. The substrate specificity of EgD5 and MaD5 for the correct ω-6 substrate (i.e., DGLA versus EDA) is approximately the same in *Yarrowia* but there is an approximate 2.5-fold preference of EgD5 for ETA (versus ETrA) over MaD5. The high activity and preferred substrate specificity for ETA over ETrA of EgD5 may be useful in the production of long-chain PUFAs. EgD5 also has a preference for ω-6 substrates (i.e., EDA and DGLA) over the ω-3 substrates (i.e., ETrA and ETA), respectively.

What is claimed is:

1. An isolated nucleic acid molecule selected from the group consisting of:
   (a) an isolated nucleotide sequence encoding a Δ5 desaturase enzyme as set forth in SEQ ID NO:2;
   (b) an isolated nucleotide sequence that hybridizes with (a) under the following hybridization conditions: 0.1×SSC, 0.1% SDS, 65° C. and washed with 2×SSC, 0.1% SDS, wherein said nucleotide sequence encodes a delta-5 desaturase followed by 0.1×SSC, 0.1% SDS; and,
   (c) an isolated nucleotide sequence that is completely complementary to (a) or (b).

2. The isolated nucleic acid molecule of claim 1, wherein at least 189 codons are codon-optimized for expression in Yarrowia.

3. The isolated nucleic acid molecule of claim 1 selected from the group of SEQ ID NOs:1 and 3.

4. An isolated nucleic acid fragment of claim 1 isolated from Euglena gracilis.

5. An isolated nucleic acid molecule comprising a first nucleotide sequence encoding a Δ5 desaturase enzyme of at least 449 amino acids that has at least 95% identity based on BLASTP algorithms when compared to a polypeptide having the sequence as set forth in SEQ ID NO:2;
   or a second nucleotide sequence comprising the complement of the first nucleotide sequence.

6. A chimeric gene comprising the isolated nucleic acid molecule of any one of claims 1-5 operably linked to at least one regulatory sequence.

7. A transformed Yarrowia sp. comprising the isolated nucleic acid molecule of claim 1.

8. The transformed Yarrowia sp. of claim 7 selected from the group consisting of Yarrowia lipolytica ATCC #20362, Yarrowia lipolytica ATCC #8862, Yarrowia lipolytica ATCC #18944, Yarrowia lipolytica ATCC #76982 and Yarrowia lipolytica LGAM S(7)1.

9. A method for the production of arachidonic acid comprising:

a) providing a host cell comprising:
   (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
   (ii) a source of dihomo-γ-linolenic acid;
b) growing the host cell of step (a) under conditions wherein the nucleic acid fragment encoding the Δ5 desaturase polypeptide is expressed and the dihomo-γ-linolenic acid is converted to arachidonic acid; and,
c) optionally recovering the arachidonic acid of step (b).

10. A method for the production of eicosapentaenoic acid comprising:
a) providing a host cell comprising:
   (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
   (ii) a source of eicosatetraenoic acid;
b) growing the host cell of step (a) under conditions wherein the nucleic acid fragment encoding the Δ5 desaturase polypeptide is expressed and the eicosatetraenoic acid is converted to eicosapentaenoic acid; and,
c) optionally recovering the eicosapentaenoic acid of step (b).

11. A method according to either of claims 9 or 10 wherein the isolated nucleic acid molecule encoding the Δ5 desaturase polypeptide is set forth in SEQ ID NO:2, wherein at least 189 codons are codon-optimized for expression in *Yarrowia*.

12. A method according to either of claims 9 or 10 wherein the isolated nucleic acid molecule encodes a Δ5 desaturase polypeptide having the amino acid sequence as set forth in SEQ ID NO:2.

13. A method according to either of claims 9 or 10 wherein:
a) the isolated nucleic acid molecule has the nucleic acid sequence selected from the group consisting of SEQ ID NOs:1 and SEQ ID NO:3; and,
b) the host cell is *Yarrowia lipolytica*.

14. A method according to either of claims 9 or 10, wherein the host cell is selected from the group consisting of: algae, bacteria, yeast, euglenoids and fungi.

15. A method according to claim 14 wherein the host cell is a fungus selected from the group consisting of: *Thraustochytrium*, *Schizochytrium* and *Mortierella*.

16. A method according to claim 14 wherein the yeast is an oleaginous yeast.

17. A method according to claim 16 wherein the oleaginous yeast is selected from the group consisting of: *Yarrowia, Candida, Rhodotorula, Rhodosporidium, Cryptococcus, Trichosporon* and *Lipomyces*.

* * * * *

SEQUENCE LISTING

<160> NUMBER OF SEQ ID NOS: 76

<210> SEQ ID NO 1
<211> LENGTH: 1350
<212> TYPE: DNA
<213> ORGANISM: Euglena gracilis
<220> FEATURE:
<221> NAME/KEY: misc_feature
<222> LOCATION: (1)..(1350)

<223> OTHER INFORMATION: delta-5 desaturase

<400> SEQUENCE: 1

```
atggctctca gtcttaccac agaacagctg ttagaacgcc ctgatttggt tgcgattgat     60
ggcatcctct acgaccttga agggcttgcc aaagttcatc caggaggaga tttgattctc    120
gcttctggtg cctctgatgc ctcccctctc ttttattcaa tgcatccata cgtcaaaccg    180
gagaattcca aattgcttca acagttcgtc cgagggaagc atgaccgcac ctcgaaggac    240
attgtctaca cgtatgattc tcccttcgca caagacgtta agcggacaat gcgcgaggtg    300
atgaaaggga ggaactggta cgcaaccccct ggcttctggc tgcgcaccgt tgggatcatc    360
gccgtgacgg ccttttgcga gtggcactgg ctaccacgg ggatggtgct gtggggcctg    420
ttgactggat tcatgcacat gcagatcggc ttatccatcc agcatgatgc gtcccacggg    480
gccatcagca agaagccttg ggtcaacgcc ctcttcgcct acggcattga cgtcatcgga    540
tcgtcccggt ggatttggct gcagtcgcac atcatgcggc accacaccta caccaaccag    600
cacggcctcg acctggatgc ggagtcggca gagccgttcc tggtgttcca caactacccc    660
gccgcaaaca ccgcccgaaa gtggttccac cgcttccaag cttggtacat gtaccttgtg    720
ctgggggcat acggggtatc gctggtgtac aacccgctct acattttccg gatgcagcac    780
aatgacacca tcccagagtc tgtcacggcc atgcgggaga atggctttct gcggcgctac    840
cgcacacttg cattcgtgat gcgagctttc ttcatcttcc ggaccgcatt cttgccctgg    900
tacctcactg ggacctcatt gctgatcacc attcctctgg tgcccactgc aactggtgcc    960
ttcttgacgt tcttcttcat tttgtcccac aattttgatg gctccgaacg gatccccgac   1020
aagaactgca aggttaagag ctctgagaag gacgttgagg ctgaccaaat tgactggtat   1080
cgggcgcagg tggagacgtc ctccacatac ggtggcccca tcgccatgtt cttcactggc   1140
ggtctcaatt ccagatcga gcaccactc tttccccgga tgtcgtcttg cactacccc    1200
ttcgtccagc aggcggtccg ggagtgttgc gaacgccatg gagtgcgata tgttttctac   1260
cctaccatcg tcggcaacat catctccacc ctgaagtaca tgcataaggt gggtgtcgtc   1320
cactgcgtga aggacgcaca ggattcctga                                   1350
```

<210> SEQ ID NO 2
<211> LENGTH: 449
<212> TYPE: PRT
<213> ORGANISM: Euglena gracilis

<400> SEQUENCE: 2

```
Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110
```

| | | | | | | | | | | | |
|---|---|---|---|---|---|---|---|---|---|---|---|
|Trp|Leu|Arg|Thr|Val|Gly|Ile|Ile|Ala|Val|Thr|Ala|Phe|Cys|Glu|Trp|
| |115| | | | |120| | | | |125| | | | |

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
130             135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn His Gly Leu Asp Leu Asp Ala Glu
        195                 200                 205

Ser Ala Glu Pro Phe Leu Val Phe His Asn Tyr Pro Ala Ala Asn Thr
210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
290                 295                 300

Thr Ser Leu Leu Ile Thr Ile Pro Leu Val Pro Thr Ala Thr Gly Ala
305                 310                 315                 320

Phe Leu Thr Phe Phe Ile Leu Ser His Asn Phe Asp Gly Ser Glu
            325                 330                 335

Arg Ile Pro Asp Lys Asn Cys Lys Val Lys Ser Ser Glu Lys Asp Val
                340                 345                 350

Glu Ala Asp Gln Ile Asp Trp Tyr Arg Ala Gln Val Glu Thr Ser Ser
            355                 360                 365

Thr Tyr Gly Gly Pro Ile Ala Met Phe Phe Thr Gly Gly Leu Asn Phe
        370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
            420                 425                 430

Tyr Met His Lys Val Gly Val Val His Cys Val Lys Asp Ala Gln Asp
        435                 440                 445

Ser

<210> SEQ ID NO 3
<211> LENGTH: 1350
<212> TYPE: DNA
<213> ORGANISM: Euglena gracilis
<220> FEATURE:
<221> NAME/KEY: misc_feature
<223> OTHER INFORMATION: synthetic delta-5 desaturase (codon-optimized)
      for Yarrowia lipolytica

<400> SEQUENCE: 3
atggctctct cccttactac cgagcagctg ctcgagcgac ccgacctggt tgccatcgac     60

```
ggcattctct acgatctgga aggtcttgcc aaggtccatc ccggaggcga cttgatcctc      120
gcttctggtg cctccgatgc ttctcctctg ttctactcca tgcacccctta cgtcaagccc     180 gagaactcga agctgcttca acagttcgtg cgaggcaagc acgaccgaac ctccaaggac      240
attgtctaca cctacgactc tcccttttgca caggacgtca agcgaactat gcgagaggtc    300
atgaaaggtc ggaactggta tgccacacct ggattctggc tgcgaaccgt tggcatcatt     360
gctgtcaccg cctttttgcga gtggcactgg gctactaccg gaatggtgct gtggggtctc    420
ttgactggat tcatgcacat gcagatcggc ctgtccattc agcacgatgc ctctcatggt    480
gccatcagca aaaagccctg ggtcaacgct ctctttgcct acggcatcga cgtcattgga    540
tcgtccagat ggatctggct gcagtctcac atcatgcgac atcacaccta caccaatcag    600
catggtctcg acctggatgc cgagtccgca gaaccattcc ttgtgttcca caactaccct    660
gctgccaaca ctgctcgaaa gtggtttcac cgattccagg cctggtacat gtacctcgtg    720
cttggagcct acggcgtttc gctggtgtac aaccctctct acatcttccg aatgcagcac    780
aacgacacca ttcccgagtc tgtcacagcc atgcgagaga acggctttct gcgacggtac    840
cgaacccttg cattcgttat gcgagctttc ttcatctttc gaaccgcctt cttgccctgg    900
tatctcactg gaacctccct gctcatcacc attcctctgg tgcccactgc taccggtgcc    960
ttcctcacct tcttttttcat cttgtctcac aacttcgatg gctcggagcg aatccccgac   1020
aagaactgca aggtcaagag ctccgagaag gacgttgaag ccgatcagat cgactggtac    1080
agagctcagg tggagacctc ttccacctac ggtggaccca ttgccatgtt ctttactggc    1140
ggtctcaact tccagatcga gcatcacctc tttcctcgaa tgtcgtcttg gcactatccc    1200
ttcgtgcagc aagctgtccg agagtgttgc gaacgacacg gagttcggta cgtcttctac    1260
cctaccattg tgggcaacat catttccacc ctcaagtaca tgcacaaagt cggtgtggtt    1320
cactgtgtca aggacgctca ggattcctaa                                      1350

<210> SEQ ID NO 4
<211> LENGTH: 590
<212> TYPE: DNA
<213> ORGANISM: Euglena gracilis

<400> SEQUENCE: 4
ggccaccaca tctacaccaa ccagcacggc ctcgacctgg atgcggagtc ggcagagccg      60
ttcctggtgt tccacaacta ccccgccgca aacaccgccc gaaagtggtt ccaccgcttc     120
caagcttggt acatgtacct tgtgctgggg gcatacgggg tatcgctggt gtacaacccg    180
ctctacattt tccggatgca gcacaatgac accatcccag agtctgtcac ggccatgcgg    240
gaaaatggct ttctgcggcg ctaccgcaca cttgcattcg tgatgcgagc tttcttcatc    300
ttccggaccg cattcttgcc ctggtacctc actgggacct cattgctgat caccattcct    360
ctggtgccca ccgcaactgg tgccttcttg acgttcttct tcattttgtc ccacaatttt    420
gatggctccg aacggatccc cgacaagaac tgcaaggtta agagctctga aaggacgtt     480 gaggctgacc aaaattgactg gtatcgggcg caggtggaga cgtcctccac atacggtggc    540
cccatcgcca tgttcttcac tggcggtctc aactaccaaa tcgtccacca                590

<210> SEQ ID NO 5
<211> LENGTH: 196
<212> TYPE: PRT
<213> ORGANISM: Euglena gracilis

<400> SEQUENCE: 5
```

```
Gly His His Ile Tyr Thr Asn Gln His Gly Leu Asp Leu Asp Ala Glu
1               5                   10                  15

Ser Ala Glu Pro Phe Leu Val Phe His Asn Tyr Pro Ala Ala Asn Thr
            20                  25                  30

Ala Arg Lys Trp Phe His Arg Phe Gln Ala Trp Tyr Met Tyr Leu Val
        35                  40                  45

Leu Gly Ala Tyr Gly Val Ser Leu Val Tyr Asn Pro Leu Tyr Ile Phe
    50                  55                  60

Arg Met Gln His Asn Asp Thr Ile Pro Glu Ser Val Thr Ala Met Arg
65                  70                  75                  80

Glu Asn Gly Phe Leu Arg Arg Tyr Arg Thr Leu Ala Phe Val Met Arg
                85                  90                  95

Ala Phe Phe Ile Phe Arg Thr Ala Phe Leu Pro Trp Tyr Leu Thr Gly
            100                 105                 110

Thr Ser Leu Leu Ile Thr Ile Pro Leu Val Pro Thr Ala Thr Gly Ala
        115                 120                 125

Phe Leu Thr Phe Phe Phe Ile Leu Ser His Asn Phe Asp Gly Ser Glu
    130                 135                 140

Arg Ile Pro Asp Lys Asn Cys Lys Val Lys Ser Ser Glu Lys Asp Val
145                 150                 155                 160

Glu Ala Asp Gln Ile Asp Trp Tyr Arg Ala Gln Val Glu Thr Ser Ser
                165                 170                 175

Thr Tyr Gly Gly Pro Ile Ala Met Phe Phe Thr Gly Gly Leu Asn Tyr
            180                 185                 190

Gln Ile Val His
        195

<210> SEQ ID NO 6
<211> LENGTH: 797
<212> TYPE: DNA
<213> ORGANISM: Euglena gracilis

<400> SEQUENCE: 6
cacagaacag ctgttagaac gccctgattt ggttgcgatt gatggcatcc tctacgacct    60
tgaagggctt gccaaagttc atccaggagg agatttgatt ctcgcttctg gtgcctctga   120
tgcctcccct ctcttttatt caatgcatcc atacgtcaaa ccggagaatt ccaaattgct   180
tcaacagttc gtccgaggga agcatgaccg cacctcgaag gacattgtct acacgtatga   240
ttctcccttc gcacaagacg ttaagcggac aatgcgcgag gtgatgaaag ggaggaactg   300
gtacgcaacc cctggcttct ggctgcgcac cgttgggatc atcgccgtga cggccttttg   360
cgagtggcac tgggctacca cggggatggt gctgtgggc ctgttgactg gattcatgca    420
catgcagatc ggcttatcca tccagcatga tgcgtcccac ggggccatca gcaaggagcc   480
ttgggtcaac gccctcttcg cctacggcat tgacgtcatc ggatcgtccc ggtggatttg   540
gctgcagtca cacatcatgc ggcaccacac ctacaccaac cagcacggcc tcgacctgga   600
tgcggagtcg gcagagccgt tcctggtgtt ccacagctac cccgccgcaa acaccgcccg   660
aaagtggttc caccgcttcc aagcttggta catgtacctt gcgctggggg catacggggt   720
atcgctggtg tacaacccgc tctacatttt ccggatgcag cacaatgaca ccatcccaga   780
gtctgtcacg gccatgc                                                  797

<210> SEQ ID NO 7
<211> LENGTH: 559
```

<212> TYPE: DNA
<213> ORGANISM: Euglena gracilis

<400> SEQUENCE: 7

```
cacagaacag ctgttagaac gccctgattt ggttgcgatt gatggcatcc tctacgacct      60
tgaagggctt gccaaagttc atccaggagg agatttgatt ctcgcttctg gtgcctctga     120
tgcctcccct ctcttttatt caatgcatcc atacgtcaaa ccggagaatt ccaaattgct     180
tcaacagttc gtccgaggga agcatgaccg cacctcgaag gacattgtct acacgtatga     240
ttctcccttc gcacaagacg ttaagcggac aatgcgcgag gtgatgaaag ggaggaactg     300
gtacgcaacc cctggcttct ggctgcgcac cgttgggatc atcgccgtga cggccttttg     360
cgagtggcac tgggctacca cggggatggt gctgtggggc ctgttgactg gattcatgca     420
catgcagatc ggcttatcca tccagcatga tgcgtcccac ggggccatca gcaaggagcc     480
ttgggtcaac gccctcttcg cctacggcat tgacgtcatc ggatcgtccc ggtggatttg     540
gctgcagtca cacatcatg                                                  559
```

<210> SEQ ID NO 8
<211> LENGTH: 273
<212> TYPE: DNA
<213> ORGANISM: Euglena gracilis

<400> SEQUENCE: 8

```
ggaatggctc tcagtcttac cacagaacag ctgttagaac gccctgattt ggttgcgatt      60
gatggcatcc tctacgacct tgaagggctt gccaaagttc atccaggagg agatttgatt     120
ctcgcttctg gtgcctctga tgcctcccct ctcttttatt caatgcatcc atacgtcaaa     180
ccggagaatt ccaaattgct tcaacagttc gtccgaggga agcatgaccg cacctcgaag     240
gacattgtct acacgtatga ttctcccttc gca                                  273
```

<210> SEQ ID NO 9
<211> LENGTH: 20
<212> TYPE: DNA
<213> ORGANISM: Euglena gracilis

<400> SEQUENCE: 9

```
ggaatggctc tcagtcttac                                                  20
```

<210> SEQ ID NO 10
<211> LENGTH: 728
<212> TYPE: DNA
<213> ORGANISM: Euglena gracilis

<400> SEQUENCE: 10

```
cctcactggg acctcattgc tgatcaccat tcctctggtg cccacygcaa ctggtgcctt      60
cttgacgttc ttcttcattt tgtcccacaa ttttgatggc tccgaacgga tcccgacaa      120
gaactgcaag gttaagagct ctgagaagga cgttgaggct gaccaaattg actggtatcg     180
ggcgcaggtg gagacgtcct ccacatacgg tggcccatc gccatgttct tcactggcgg      240
tctcaatttc cagatcgagc accacctctt tccccggatg tcgtcttggc actacccctt     300
cgtccagcag gcggtccggg agtgttgcga acgccatgga gtgcgatatg ttttctaccc     360
taccatcgtc ggcaacatca tctccaccct gaagtacatg cataaggtgg gtgtcgtcca     420
ctgcgtgaag gacgcacagg attcctgagg ggcagggtga ccaagaacga tcatcgatgt     480
gttcttctgg cccttggtg gggtactcgc cagattgctc cactgaaccg tatcctaact     540
```

-continued

```
ctgaccctct ccaaccctgt gttgagtgtt tgctttatgc tccaaagtgg cttcttattt      600
ggtgacccgt ggggcagcgg cacctgtgcc atgcagctga taacccaggc tgctactcta      660
agttggatgg ccaatcgtct ggcattgata tccctgctca gcgttgcatt ccaatggttt      720
gcttatcc                                                                728
```

<210> SEQ ID NO 11
<211> LENGTH: 464
<212> TYPE: DNA
<213> ORGANISM: Euglena gracilis

<400> SEQUENCE: 11

```
cctctttccc cggatgtcgt cttggcacta ccccttcgtc cagcaggcgg tccgggagtg       60
ttgcgaacgc catggagtgc gatatgtttt ctaccctacc atcgtcggca acatcatctc      120
caccctgaag tacatgcata aggtgggtgt cgtccactgc gtgaaggacg cacaggattc      180 ctgagggca gggtgaccaa gaacgatcat cgatgtgttc ttctggccct tggtggggt       240 actcgccaga ttgctccact gaaccgtatc ctaactctga ccctctccaa ccctgtgttg      300
agtgtttgct ttatgctcca aagtggcttc ttatttggtg acccgtgggg cagcggcacc      360
tgtgccatgc agctgataac ccaggctgct actctaagtt ggatggccaa tcgtctggca      420
ttgatatccc tgctcagcgt tgcattccaa tggtttgctt atcc                        464
```

<210> SEQ ID NO 12
<211> LENGTH: 456
<212> TYPE: PRT
<213> ORGANISM: Pythium irregulare (GenBank Accession No. AAL13311)
<220> FEATURE:
<221> NAME/KEY: MISC_FEATURE
<223> OTHER INFORMATION: delta-5 desaturase

<400> SEQUENCE: 12

```
Met Gly Thr Asp Gln Gly Lys Thr Phe Thr Trp Gln Glu Val Ala Lys
  1               5                  10                  15

His Asn Thr Ala Lys Ser Ala Trp Val Ile Ile Arg Gly Glu Val Tyr
             20                  25                  30

Asp Val Thr Glu Trp Ala Asp Lys His Pro Gly Gly Ser Glu Leu Ile
         35                  40                  45

Val Leu His Ser Gly Arg Glu Cys Thr Asp Thr Phe Tyr Ser Tyr His
     50                  55                  60

Pro Phe Ser Asn Arg Ala Asp Lys Ile Leu Ala Lys Tyr Lys Ile Gly
 65                  70                  75                  80

Lys Leu Val Gly Gly Tyr Glu Phe Pro Val Phe Lys Pro Asp Ser Gly
                 85                  90                  95

Phe Tyr Lys Glu Cys Ser Glu Arg Val Ala Glu Tyr Phe Lys Thr Asn
            100                 105                 110

Asn Leu Asp Pro Lys Ala Ala Phe Ala Gly Leu Trp Arg Met Val Phe
        115                 120                 125

Val Phe Ala Val Ala Leu Ala Tyr Met Gly Met Asn Glu Leu Ile
    130                 135                 140

Pro Gly Asn Val Tyr Ala Gln Tyr Ala Trp Gly Val Val Phe Gly Val
145                 150                 155                 160

Phe Gln Ala Leu Pro Leu Leu His Val Met His Asp Ser Ser His Ala
                165                 170                 175

Ala Cys Ser Ser Ser Pro Ala Met Trp Gln Ile Ile Gly Arg Gly Val
            180                 185                 190
```

```
Met Asp Trp Phe Ala Gly Ala Ser Met Val Ser Trp Leu Asn Gln His
        195                 200                 205

Val Val Gly His His Ile Tyr Thr Asn Val Ala Gly Ala Asp Pro Asp
    210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                245                 250                 255

Tyr Gly Val Leu Gly Leu Lys Phe Arg Ile Gln Asp Val Phe Glu Thr
            260                 265                 270

Phe Val Ser Leu Thr Asn Gly Pro Val Arg Val Asn Pro His Pro Val
        275                 280                 285

Ser Asp Trp Val Gln Met Ile Phe Ala Lys Ala Phe Trp Thr Phe Tyr
    290                 295                 300

Arg Ile Tyr Ile Pro Leu Val Trp Leu Lys Ile Thr Pro Ser Thr Phe
305                 310                 315                 320

Trp Gly Val Phe Phe Leu Ala Glu Phe Thr Thr Gly Trp Tyr Leu Ala
                325                 330                 335

Phe Asn Phe Gln Val Ser His Val Ser Thr Glu Cys Glu Tyr Pro Cys
            340                 345                 350

Gly Asp Ala Pro Ser Ala Glu Val Gly Asp Glu Trp Ala Ile Ser Gln
        355                 360                 365

Val Lys Ser Ser Val Asp Tyr Ala His Gly Ser Pro Leu Ala Ala Phe
    370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Asp Val
                405                 410                 415

Cys Lys Lys Tyr Asn Ile Lys Tyr Thr Val Leu Pro Thr Phe Thr Glu
            420                 425                 430

Ala Leu Leu Ala His Phe Lys His Leu Lys Asn Met Gly Glu Leu Gly
        435                 440                 445

Lys Pro Val Glu Ile His Met Gly
    450                 455

<210> SEQ ID NO 13
<211> LENGTH: 477
<212> TYPE: PRT
<213> ORGANISM: Phytophthora megasperma (GenBank Accession No. CAD53323)
<220> FEATURE:
<221> NAME/KEY: MISC_FEATURE
<223> OTHER INFORMATION: delta-5 desaturase

<400> SEQUENCE: 13

Met Ala Pro Ile Glu Thr Val Lys Asp Ala Asn Glu Gly Leu His Gln
1               5                   10                  15

Arg Lys Gly Ala Ala Ala Ser Lys Asp Thr Thr Phe Thr Trp
            20                  25                  30

Gln Asp Val Ala Lys His Asn Thr Ala Lys Ser Ala Trp Val Thr Ile
        35                  40                  45

Arg Gly Val Val Tyr Asp Val Thr Glu Trp Ala Asp Arg His Pro Gly
    50                  55                  60

Gly Arg Glu Leu Val Leu Leu His Ser Gly Arg Glu Cys Thr Asp Thr
65                  70                  75                  80

Phe Asp Ser Tyr His Pro Phe Ser Asp Arg Ala Asp Lys Ile Leu Ala
                85                  90                  95
```

```
Lys Tyr Ala Ile Gly Lys Leu Val Gly Gly Ser Glu Phe Pro Thr Tyr
                100                 105                 110
Lys Pro Asp Thr Gly Phe Tyr Lys Glu Cys Cys Asp Arg Val Asn Gln
            115                 120                 125
Tyr Phe Lys Asp Asn Lys Leu Asp Pro Arg Ser Pro Tyr Ser Gly Leu
        130                 135                 140
Trp Arg Met Ile Leu Val Ala Ile Val Gly Ala Val Ala Tyr Met Gly
145                 150                 155                 160
Met Asn Gln Leu Leu Pro Gly Asn Ile Tyr Ala His Tyr Ala Trp Gly
                165                 170                 175
Ala Leu Phe Gly Val Cys Gln Ala Leu Pro Leu Leu His Val Met His
            180                 185                 190
Asp Ala Ser His Ala Ala Ile Thr Ser Ser Pro Thr Gly Trp Arg Leu
        195                 200                 205
Ile Gly Arg Leu Ala Met Asp Trp Val Gly Ala Asn Met Val Ser
210                 215                 220
Trp Leu Asn Gln His Val Val Gly His His Ile Tyr Thr Asn Val Ala
225                 230                 235                 240
Gly Ala Asp Pro Asp Leu Pro Val Asp Phe Lys Ser Asp Val Arg Arg
                245                 250                 255
Ile Val Tyr Arg Gln Val Leu Leu Pro Ile Tyr Lys Tyr Gln His Leu
            260                 265                 270
Tyr Leu Pro Pro Leu Tyr Gly Val Leu Gly Leu Lys Phe Arg Val Gln
        275                 280                 285
Asp Val Phe Glu Thr Phe Val Thr Leu Thr Asn Gly Pro Leu Arg Val
        290                 295                 300
Asn Pro Leu Ser Val Gly Asp Trp Ala Glu Met Ile Leu Ser Lys Ala
305                 310                 315                 320
Phe Trp Val Phe Tyr Arg Ile Tyr Leu Pro Leu Ala Val Leu Gln Val
                325                 330                 335
Asp Pro Ala Arg Phe Trp Gly Val Phe Phe Leu Ala Glu Phe Ser Thr
            340                 345                 350
Gly Trp Tyr Leu Ala Phe Asn Phe Gln Val Ser His Val Ser Thr Ala
        355                 360                 365
Cys Glu Tyr Pro Gly Gly Asp Glu Glu Val Thr Ser Ile Asp Asp Glu
        370                 375                 380
Trp Ala Ile Ser Gln Val Lys Ser Ser Val Asp Tyr Gly His Gly Ser
385                 390                 395                 400
Phe Ile Thr Thr Phe Leu Thr Gly Ala Leu Asn Tyr Gln Val Thr His
                405                 410                 415
His Leu Phe Pro Gly Val Ser Gln Tyr His Tyr Pro Ala Ile Ala Pro
            420                 425                 430
Leu Ile Leu Asp Val Cys His Lys Tyr Lys Val Lys Tyr Asn Val Leu
        435                 440                 445
Pro Asp Phe Thr Ala Ala Met Ala Gly His Phe Asp His Leu Val Ile
        450                 455                 460
Met Gly Lys Met Gly Lys Arg Val Thr Ile His Met Gly
465                 470                 475

<210> SEQ ID NO 14
<211> LENGTH: 469
<212> TYPE: PRT
<213> ORGANISM: Phaeodactylum tricornutum (GenBank Accession No.
      AAL92562)
```

```
<220> FEATURE:
<221> NAME/KEY: MISC_FEATURE
<223> OTHER INFORMATION: delta-5 desaturase

<400> SEQUENCE: 14
```

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
370                 375                 380

Gly Phe Leu Ser Gly Cys Phe Thr Gly Gly Leu Asn Phe Gln Val Glu

```
385                 390                 395                 400
His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 15
<211> LENGTH: 467
<212> TYPE: PRT
<213> ORGANISM: Dictyostelium discoideum (GenBank Accession No.
      XP_640331)
<220> FEATURE:
<221> NAME/KEY: MISC_FEATURE
<223> OTHER INFORMATION: delta-5 desaturase

<400> SEQUENCE: 15

Met Met Glu Thr Asn Asn Glu Asn Lys Glu Lys Leu Lys Leu Tyr Thr
1               5                   10                  15

Trp Asp Glu Val Ser Lys His Asn Gln Lys Asn Asp Leu Trp Ile Ile
            20                  25                  30

Val Asp Gly Lys Val Tyr Asn Ile Thr Lys Trp Val Pro Leu His Pro
        35                  40                  45

Gly Gly Glu Asp Ile Leu Leu Leu Ser Ala Gly Arg Asp Ala Thr Asn
    50                  55                  60

Leu Phe Glu Ser Tyr His Pro Met Thr Asp Lys His Tyr Ser Leu Ile
65                  70                  75                  80

Lys Gln Tyr Glu Ile Gly Tyr Ile Ser Ser Tyr Glu His Pro Lys Tyr
                85                  90                  95

Val Glu Lys Ser Glu Phe Tyr Ser Thr Leu Lys Gln Arg Val Arg Lys
            100                 105                 110

His Phe Gln Thr Ser Ser Gln Asp Pro Lys Val Ser Val Gly Val Phe
        115                 120                 125

Thr Arg Met Val Leu Ile Tyr Leu Phe Leu Phe Val Thr Tyr Tyr Leu
    130                 135                 140

Ser Gln Phe Ser Thr Asp Arg Phe Trp Leu Asn Cys Ile Phe Ala Val
145                 150                 155                 160

Leu Tyr Gly Val Ala Asn Ser Leu Phe Gly Leu His Thr Met His Asp
                165                 170                 175

Ala Cys His Thr Ala Ile Thr His Asn Pro Met Thr Trp Lys Ile Leu
            180                 185                 190

Gly Ala Thr Phe Asp Leu Phe Ala Gly Ala Ser Phe Tyr Ala Trp Cys
        195                 200                 205

His Gln His Val Ile Gly His His Leu Tyr Thr Asn Val Arg Asn Ala
    210                 215                 220

Asp Pro Asp Leu Gly Gln Gly Glu Ile Asp Phe Arg Val Val Thr Pro
225                 230                 235                 240

Tyr Gln Ala Arg Ser Trp Tyr His Lys Tyr Gln His Ile Tyr Ala Pro
                245                 250                 255

Ile Leu Tyr Gly Val Tyr Ala Leu Lys Tyr Arg Ile Gln Asp His Glu
            260                 265                 270
```

```
Ile Phe Thr Lys Lys Ser Asn Gly Ala Ile Arg Tyr Ser Pro Ile Ser
        275                 280                 285

Thr Ile Asp Thr Ala Ile Phe Ile Leu Gly Lys Leu Val Phe Ile Ile
        290                 295                 300

Ser Arg Phe Ile Leu Pro Leu Ile Tyr Asn His Ser Phe Ser His Leu
305                 310                 315                 320

Ile Cys Phe Phe Leu Ile Ser Glu Leu Val Leu Gly Trp Tyr Leu Ala
                325                 330                 335

Ile Ser Phe Gln Val Ser His Val Val Glu Asp Leu Gln Phe Met Ala
                340                 345                 350

Thr Pro Glu Ile Phe Asp Gly Ala Asp His Pro Leu Pro Thr Thr Phe
        355                 360                 365

Asn Gln Asp Trp Ala Ile Leu Gln Val Lys Thr Thr Gln Asp Tyr Ala
        370                 375                 380

Gln Asp Ser Val Leu Ser Thr Phe Phe Ser Gly Gly Leu Asn Leu Gln
385                 390                 395                 400

Val Ile His His Cys Phe Pro Thr Ile Ala Gln Asp Tyr Tyr Pro Gln
                405                 410                 415

Ile Val Pro Ile Leu Lys Glu Val Cys Lys Glu Tyr Asn Val Thr Tyr
                420                 425                 430

His Tyr Lys Pro Thr Phe Thr Glu Ala Ile Lys Ser His Ile Asn Tyr
        435                 440                 445

Leu Tyr Lys Met Gly Asn Asp Pro Asp Tyr Val Arg Lys Pro Val Asn
        450                 455                 460

Lys Asn Asp
465

<210> SEQ ID NO 16
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012325
<311> PATENT FILING DATE: 2005-06-24
<312> PUBLICATION DATE: 2006-02-02
<313> RELEVANT RESIDUES: (1)..(421)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012326
<311> PATENT FILING DATE: 2005-06-24
<312> PUBLICATION DATE: 2006-02-02
<313> RELEVANT RESIDUES: (1)..(421)

<400> SEQUENCE: 16

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Pro Gln Ala Ala Val Asn Glu Ala Gln Glu
65                  70                  75                  80
```

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Met Pro Ser Ile
        275                 280                 285

Leu Thr Ser Leu Leu Val Phe Val Ser Glu Leu Val Gly Gly Phe
290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 17
<211> LENGTH: 1269
<212> TYPE: DNA
<213> ORGANISM: Pavlova lutheri
<220> FEATURE:
<221> NAME/KEY: misc_feature
<223> OTHER INFORMATION: delta-8 desaturase

<400> SEQUENCE: 17
atgggcaagg gtggagacgg cggcgcgcag gcggtgagcg ggaccgacgc gtctctcgct      60

```
gaggtgagct ccgtcgatag caagagcgtg cacgtcgtgc tctacggcaa gcgcgtggat      120
gtcacaaagt tccagaaggc acacccgggc gggagcaagg tgttccgcat cttccaggag      180
cgcgacgcga cggagcagtt cgagtcttac cactcgccca aggccatcaa gatgatggag      240
ggcatgctca agaagtcgga ggatgcgccc gcttccgtgc ccctgccctc gcggtccacc      300
atgggcacgg agttcaagga gatgattgag cgccacaaga gggctggtct ctacgaccct      360
tgcccgttgg acgagctgtt caagctcacc atcgtccttg cgcccatctt cgtgggcgcc      420
tatctcgtgc ggagcggcgt ctcgcccctc gcgggcgcgc tctccatggg ctttggcttc      480
tacctcgacg gctggcttgc tcacgactac ctgcatcacg cagtcttcaa gggctcggtc      540
aacacgctcg tcaaggcgaa caacgccatg ggatacgccc tcggcttcct ccagggctac      600
gacgtggcct ggtggcgcgc gcgccataac acgcaccacg tgtgcaccaa cgaggatggt      660
tcggacccgg acatcaagac ggcgcccctg ctcatctacg tgcgagagaa cccgtccatt      720
gccaagcggc tcaacttctt ccagcgctgg cagcagtact actatgtgcc gaccatggcc      780
atcctcgacc tctactggcg cctggagtcc atcgcgtacg tggctgtgcg cctgcctaag      840
atgtggatgc aggccgccgc tcttgccgct cactacgcgc tcctgtgctg ggtcttcgca      900
gcgcatctca acctcatccc tctcatgatg gttgcacgcg gcttcgcgac gggcatcgtt      960
gtctttgcaa cccactatgg tgaggacatc ctcgaccgcg agcacgtcga gggcatgacg     1020
ctcgtcgagc agaccgccaa gacctcccgt aacatcacgg gcggctggct agtgaacgtg     1080
ctcacgggct tcatctccct gcagaccgag catcacctct tccccatgat gcccaccggc     1140
aacctaatga ctatccagcc cgaggtacgc gacttcttca gaagcatggg cctcgagtac     1200
cgcgagggca acctcttcca gtgcgtgcac cagaacatca aggctctcgc cttcgagcac     1260
ctcctccac                                                             1269
```

<210> SEQ ID NO 18
<211> LENGTH: 423
<212> TYPE: PRT
<213> ORGANISM: Pavlova lutheri

<400> SEQUENCE: 18

```
Met Gly Lys Gly Gly Asp Gly Gly Ala Gln Ala Val Ser Gly Thr Asp
1               5                   10                  15

Ala Ser Leu Ala Glu Val Ser Ser Val Asp Ser Lys Ser Val His Val
            20                  25                  30

Val Leu Tyr Gly Lys Arg Val Asp Val Thr Lys Phe Gln Lys Ala His
        35                  40                  45

Pro Gly Gly Ser Lys Val Phe Arg Ile Phe Gln Glu Arg Asp Ala Thr
    50                  55                  60

Glu Gln Phe Glu Ser Tyr His Ser Pro Lys Ala Ile Lys Met Met Glu
65                  70                  75                  80

Gly Met Leu Lys Lys Ser Glu Asp Ala Pro Ala Ser Val Pro Leu Pro
                85                  90                  95

Ser Arg Ser Thr Met Gly Thr Glu Phe Lys Glu Met Ile Glu Arg His
            100                 105                 110

Lys Arg Ala Gly Leu Tyr Asp Pro Cys Pro Leu Asp Glu Leu Phe Lys
        115                 120                 125

Leu Thr Ile Val Leu Ala Pro Ile Phe Val Gly Ala Tyr Leu Val Arg
    130                 135                 140

Ser Gly Val Ser Pro Leu Ala Gly Ala Leu Ser Met Gly Phe Gly Phe
```

```
                145                 150                 155                 160
Tyr Leu Asp Gly Trp Leu Ala His Asp Tyr Leu His His Ala Val Phe
                    165                 170                 175
Lys Gly Ser Val Asn Thr Leu Val Lys Ala Asn Asn Ala Met Gly Tyr
                180                 185                 190
Ala Leu Gly Phe Leu Gln Gly Tyr Asp Val Ala Trp Trp Arg Ala Arg
            195                 200                 205
His Asn Thr His His Val Cys Thr Asn Glu Asp Gly Ser Asp Pro Asp
        210                 215                 220
Ile Lys Thr Ala Pro Leu Leu Ile Tyr Val Arg Glu Asn Pro Ser Ile
225                 230                 235                 240
Ala Lys Arg Leu Asn Phe Phe Gln Arg Trp Gln Gln Tyr Tyr Tyr Val
                245                 250                 255
Pro Thr Met Ala Ile Leu Asp Leu Tyr Trp Arg Leu Glu Ser Ile Ala
                260                 265                 270
Tyr Val Ala Val Arg Leu Pro Lys Met Trp Met Gln Ala Ala Ala Leu
            275                 280                 285
Ala Ala His Tyr Ala Leu Leu Cys Trp Val Phe Ala Ala His Leu Asn
        290                 295                 300
Leu Ile Pro Leu Met Met Val Ala Arg Gly Phe Ala Thr Gly Ile Val
305                 310                 315                 320
Val Phe Ala Thr His Tyr Gly Glu Asp Ile Leu Asp Arg Glu His Val
                325                 330                 335
Glu Gly Met Thr Leu Val Glu Gln Thr Ala Lys Thr Ser Arg Asn Ile
                340                 345                 350
Thr Gly Gly Trp Leu Val Asn Val Leu Thr Gly Phe Ile Ser Leu Gln
            355                 360                 365
Thr Glu His His Leu Phe Pro Met Met Pro Thr Gly Asn Leu Met Thr
        370                 375                 380
Ile Gln Pro Glu Val Arg Asp Phe Phe Lys Lys His Gly Leu Glu Tyr
385                 390                 395                 400
Arg Glu Gly Asn Leu Phe Gln Cys Val His Gln Asn Ile Lys Ala Leu
                405                 410                 415
Ala Phe Glu His Leu Leu His
            420

<210> SEQ ID NO 19
<211> LENGTH: 7
<212> TYPE: PRT
<213> ORGANISM: Artificial Sequence
<220> FEATURE:
<223> OTHER INFORMATION: Conserved region #1 within delta-5 and delta-8
      desaturases
<220> FEATURE:
<221> NAME/KEY: MISC_FEATURE
<222> LOCATION: (4)..(4)
<223> OTHER INFORMATION: X = Ile or Val

<400> SEQUENCE: 19

Gly His His Xaa Tyr Thr Asn
1               5

<210> SEQ ID NO 20
<211> LENGTH: 7
<212> TYPE: PRT
<213> ORGANISM: Artificial Sequence
<220> FEATURE:
<223> OTHER INFORMATION: Conserved region #2 within delta-5 and delta-8
      desaturases
```

```
<220> FEATURE:
<221> NAME/KEY: MISC_FEATURE
<222> LOCATION: (2)..(2)
<223> OTHER INFORMATION: X = Y or F
<220> FEATURE:
<221> NAME/KEY: MISC_FEATURE
<222> LOCATION: (4)..(4)
<223> OTHER INFORMATION: X = Val or Ile

<400> SEQUENCE: 20

Asn Xaa Gln Xaa Glu His His
1               5

<210> SEQ ID NO 21
<211> LENGTH: 476
<212> TYPE: PRT
<213> ORGANISM: Thalassiosira pseudonana (GenBank Accession No.
      AAX14502)
<220> FEATURE:
<221> NAME/KEY: MISC_FEATURE
<223> OTHER INFORMATION: delta-8 desaturase

<400> SEQUENCE: 21

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asn Asp Pro Ala Thr Gln
            20                  25                  30

Ser Val Arg Thr Leu Lys Ser Leu Lys Gly Asn Glu Val Val Ile Asn
        35                  40                  45

Gly Thr Ile Tyr Asp Ile Ala Asp Phe Val His Pro Gly Gly Glu Val
    50                  55                  60

Val Lys Phe Phe Gly Gly Asn Asp Val Thr Ile Gln Tyr Asn Met Ile
65                  70                  75                  80

His Pro Tyr His Thr Gly Lys His Leu Glu Lys Met Lys Ala Val Gly
                85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Phe Tyr Ile Ala Leu
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175

Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
        195                 200                 205

Thr Asp Leu Ile Gly Ser Asn Lys Trp Asn Trp Met Ala Gln His Trp
    210                 215                 220

Thr His His Ala Tyr Thr Asn His Ser Glu Lys Asp Pro Asp Ser Phe
225                 230                 235                 240

Ser Ser Glu Pro Met Phe Ala Phe Asn Asp Tyr Pro Ile Gly His Pro
                245                 250                 255

Lys Arg Lys Trp Trp His Arg Phe Gln Gly Gly Tyr Phe Leu Phe Met
            260                 265                 270

Leu Gly Leu Tyr Trp Leu Pro Thr Val Phe Asn Pro Gln Phe Ile Asp
        275                 280                 285
```

```
Leu Arg Gln Arg Gly Ala Gln Tyr Val Gly Ile Gln Met Glu Asn Asp
        290                 295                 300

Phe Ile Val Lys Arg Arg Lys Tyr Ala Val Ala Leu Arg Met Met Tyr
305                 310                 315                 320

Ile Tyr Leu Asn Ile Val Ser Pro Phe Met Asn Asn Gly Leu Ser Trp
                325                 330                 335

Ser Thr Phe Gly Ile Ile Met Leu Met Gly Ile Ser Glu Ser Leu Thr
            340                 345                 350

Leu Ser Val Leu Phe Ser Leu Ser His Asn Phe Ile Asn Ser Asp Arg
        355                 360                 365

Asp Pro Thr Ala Asp Phe Lys Lys Thr Gly Glu Gln Val Cys Trp Phe
370                 375                 380

Lys Ser Gln Val Glu Thr Ser Ser Thr Tyr Gly Gly Phe Ile Ser Gly
385                 390                 395                 400

Cys Leu Thr Gly Gly Leu Asn Phe Gln Val Glu His His Leu Phe Pro
                405                 410                 415

Arg Met Ser Ser Ala Trp Tyr Pro Tyr Ile Ala Pro Thr Val Arg Glu
            420                 425                 430

Val Cys Lys Lys His Gly Met Ser Tyr Ala Tyr Tyr Pro Trp Ile Gly
        435                 440                 445

Gln Asn Leu Val Ser Thr Phe Lys Tyr Met His Arg Ala Gly Ser Gly
    450                 455                 460

Ala Asn Trp Glu Leu Lys Pro Leu Ser Gly Ser Ala
465                 470                 475

<210> SEQ ID NO 22
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 22
gtacgagccg gaagcataaa gtgtaaagcc tggggtgcct aatgagtgag ctaactcaca    60
ttaattgcgt tgcgctcact gcccgctttc cagtcgggaa acctgtcgtg ccagctgcat   120
taatgaatcg gccaacgcgc ggggagaggc ggtttgcgta ttgggcgctc ttccgcttcc   180
tcgctcactg actcgctgcg ctcggtcgtt cggctgcggc gagcggtatc agctcactca   240
aaggcggtaa tacggttatc cacagaatca ggggataacg caggaaagaa catgtgagca   300
aaaggccagc aaaaggccag gaaccgtaaa aaggccgcgt tgctggcgtt tttccatagg   360
ctccgccccc ctgacgagca tcacaaaaat cgacgctcaa gtcagaggtg gcgaaacccg   420
acaggactat aaagatacca ggcgtttccc cctggaagct ccctcgtgcg ctctcctgtt   480
ccgaccctgc cgcttaccgg atacctgtcc gcctttctcc cttcgggaag cgtggcgctt   540
tctcatagct cacgctgtag gtatctcagt tcggtgtagg tcgttcgctc caagctgggc   600
tgtgtgcacg aaccccccgt tcagcccgac cgctgcgcct tatccggtaa ctatcgtctt   660
gagtccaacc cggtaagaca cgacttatcg ccactggcag cagccactgg taacaggatt   720
agcagagcga ggtatgtagg cggtgctaca gagttcttga agtggtggcc taactacggc   780
tacactagaa ggacagtatt tggtatctgc gctctgctga agccagttac cttcggaaaa   840
agagttggta gctcttgatc cggcaaacaa accaccgctg gtagcggtgg ttttttgtt   900 tgcaagcagc agattacgcg cagaaaaaaa ggatctcaag aagatccttt gatcttttct   960
```

```
acggggtctg acgctcagtg gaacgaaaac tcacgttaag ggattttggt catgagatta    1020
tcaaaaagga tcttcaccta gatccttta aattaaaaat gaagttttaa atcaatctaa    1080
agtatatatg agtaaacttg gtctgacagt taccaatgct taatcagtga ggcacctatc    1140
tcagcgatct gtctatttcg ttcatccata gttgcctgac tccccgtcgt gtagataact    1200
acgatacggg agggcttacc atctggcccc agtgctgcaa tgataccgcg agacccacgc    1260
tcaccggctc cagatttatc agcaataaac cagccagccg aagggccga gcgcagaagt    1320 ggtcctgcaa ctttatccgc ctccatccag tctattaatt gttgccggga agctagagta    1380
agtagttcgc cagttaatag tttgcgcaac gttgttgcca ttgctacagg catcgtggtg    1440
tcacgctcgt cgtttggtat ggcttcattc agctccggtt cccaacgatc aaggcgagtt    1500
acatgatccc ccatgttgtg caaaaaagcg gttagctcct tcggtcctcc gatcgttgtc    1560
agaagtaagt tggccgcagt gttatcactc atggttatgg cagcactgca taattctctt    1620
actgtcatgc catccgtaag atgcttttct gtgactggtg agtactcaac caagtcattc    1680
tgagaatagt gtatgcggcg accgagttgc tcttgcccgg cgtcaatacg ggataatacc    1740
gcgccacata gcagaacttt aaaagtgctc atcattggaa aacgttcttc ggggcgaaaa    1800
ctctcaagga tcttaccgct gttgagatcc agttcgatgt aacccactcg tgcacccaac    1860
tgatcttcag catcttttac tttcaccagc gtttctgggt gagcaaaaac aggaaggcaa    1920
aatgccgcaa aaaagggaat aagggcgaca cggaaatgtt gaatactcat actcttcctt    1980
tttcaatatt attgaagcat ttatcagggt tattgtctca tgagcggata catatttgaa    2040
tgtatttaga aaaataaaca aataggggtt ccgcgcacat ttccccgaaa agtgccacct    2100
gacgcgccct gtagcggcgc attaagcgcg gcgggtgtgg tggttacgcg cagcgtgacc    2160
gctacacttg ccagcgccct agcgcccgct cctttcgctt tcttcccttc ctttctcgcc    2220
acgttcgccg gctttccccg tcaagctcta aatcggggc tccctttagg gttccgattt    2280
agtgctttac ggcacctcga ccccaaaaaa cttgattagg gtgatggttc acgtagtggg    2340
ccatcgccct gatagacggt ttttcgccct ttgacgttgg agtccacgtt ctttaatagt    2400
ggactcttgt tccaaactgg aacaacactc aaccctatct cggtctattc ttttgattta    2460
taagggattt tgccgatttc ggcctattgg ttaaaaaatg agctgattta acaaaaattt    2520
aacgcgaatt ttaacaaaat attaacgctt acaatttcca ttcgccattc aggctgcgca    2580
actgttggga agggcgatcg gtgcgggcct cttcgctatt acgccagctg gcgaaagggg    2640
gatgtgctgc aaggcgatta agttgggtaa cgccagggtt ttcccagtca cgacgttgta    2700
aaacgacggc cagtgaattg taatacgact cactataggg cgaattgggt accgggcccc    2760
ccctcgaggt cgatggtgtc gataagcttg atatcgaatt catgtcacac aaaccgatct    2820
tcgcctcaag gaaacctaat tctacatccg agagactgcc gagatccagt ctacactgat    2880
taattttcgg gccaataatt taaaaaaatc gtgttatata atattatatg tattatatat    2940
atacatcatg atgatactga cagtcatgtc ccattgctaa atagacagac tccatctgcc    3000
gcctccaact gatgttctca atatttaagg ggtcatctcg cattgtttaa taataaacag    3060
actccatcta ccgcctccaa atgatgttct caaatatat tgtatgaact tatttttatt    3120
acttagtatt attagacaac ttacttgctt tatgaaaaac acttcctatt taggaaacaa    3180
tttataatgg cagttcgttc atttaacaat ttatgtagaa taaatgttat aaatgcgtat    3240
gggaaatctt aaatatggat agcataaatg atatctgcat tgcctaattc gaaatcaaca    3300
gcaacgaaaa aaatcccttg tacaacataa atagtcatcg agaaatatca actatcaaag    3360
```

```
aacagctatt cacacgttac tattgagatt attattggac gagaatcaca cactcaactg    3420
tctttctctc ttctagaaat acaggtacaa gtatgtacta ttctcattgt tcatacttct    3480
agtcatttca tcccacatat tccttggatt tctctccaat gaatgacatt ctatcttgca    3540
aattcaacaa ttataataag ataccaaa gtagcggtat agtggcaatc aaaaagcttc      3600
tctggtgtgc ttctcgtatt tattttat ctaatgatcc attaaaggta tatttatt        3660 tcttgttata taatccttt gtttattaca tgggctggat acataaaggt attttgattt     3720 aatttttgc ttaaattcaa tcccccctcg ttcagtgtca actgtaatgg taggaaatta     3780
ccatactttt gaagaagcaa aaaaatgaa agaaaaaaa aatcgtattt ccaggttaga      3840
cgttccgcag aatctagaat gcggtatgcg gtacattgtt cttcgaacgt aaaagttgcg    3900
ctccctgaga tattgtacat ttttgctttt acaagtacaa gtacatcgta caactatgta    3960
ctactgttga tgcatccaca acagtttgtt ttgttttttt ttgttttttt ttttctaat     4020 gattcattac cgctatgtat acctacttgt acttgtagta agccgggtta ttggcgttca    4080
attaatcata gacttatgaa tctgcacggt gtgcgctgcg agttactttt agcttatgca    4140
tgctacttgg gtgtaatatt gggatctgtt cggaaatcaa cggatgctca atcgatttcg    4200
acagtaatta attaagtcat acacaagtca gctttcttcg agcctcatat aagtataagt    4260
agttcaacgt attagcactg tacccagcat ctccgtatcg agaaacacaa caacatgccc    4320
cattggacag atcatgcgga tacacaggtt gtgcagtatc atacatactc gatcagacag    4380
gtcgtctgac catcatacaa gctgaacaag cgctccatac ttgcacgctc tctatataca    4440
cagttaaatt acatatccat agtctaacct ctaacagtta atcttctggt aagcctccca    4500
gccagccttc tggtatcgct tggcctcctc aataggatct cggttctggc cgtacagacc    4560
tcggccgaca attatgatat ccgttccggt agacatgaca tcctcaacag ttcggtactg    4620
ctgtccgaga gcgtctccct tgtcgtcaag acccacccg gggtcagaa taagccagtc      4680 ctcagagtcg ccccttaggtc ggttctgggc aatgaagcca accacaaact cggggtcgga   4740
tcgggcaagc tcaatggtct gcttggagta ctcgccagtg ccagagagc ccttgcaaga     4800 cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag gaagaaaccg tgcttaagag caagttcctt    5100 gaggggagc acagtgccgg cgtaggtgaa gtcgtcaatg atgtcgatat gggttttgat     5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg ggcagtgaa     5400 gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
```

```
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggccttt tatatggcca agccaagctc tccacgtcgg ttgggctgca cccaacaata   5940
aatgggtagg gttgcaccaa caaagggatg ggatggggg tagaagatac gaggataacg    6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaagtga gggcgctgag gtcgagcagg    6240
gtggtgtgac ttgttatagc ctttagagct gcgaaagcgc gtatggattt ggctcatcag   6300
gccagattga gggtctgtgg acacatgtca tgttagtgta cttcaatcgc ccctggata   6360
tagccccgac aataggccgt ggcctcattt ttttgccttc cgcacattc cattgctcgg    6420
tacccacacc ttgcttctcc tgcacttgcc aaccttaata ctggtttaca ttgaccaaca   6480
tcttacaagc gggggcttg tctagggtat atataaacag tggctctccc aatcggttgc    6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga cgacgcgt tttgtgtaat gacacaatcc     6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
ctttgagtcc aacctcggac tctcgctcta ctacactgcc cgagcgatct tcaacgcatc   6900
tgcctctgct gctctgctct acgctgcccg atctactccc ttcattgccg ataacgttct   6960
gctccacgct ctggtttgcg ccacctacat ctacgtgcag ggtgtcatct tctgggtttt   7020
ctttaccgtc ggtcacgact gtggtcactc tgccttctcc cgataccact ccgtcaactt   7080
catcattggc tgcatcatgc actctgccat tctgactccc ttcgagtcct ggcgagtgac   7140
ccaccgacac catcacaaga acactggcaa cattgataag gacgagatct tctaccctca   7200
tcggtccgtc aaggacctcc aggacgtgcg acaatgggtc tacaccctcg gaggtgcttg   7260
gtttgtctac ctgaaggtcg atatgctcc tcgaaccatg tcccactttg accctgga     7320
ccctctcctg cttcgacgag cctccgctgt catcgtgtcc ctcggagtct gggctgcctt   7380
cttcgctgcc tacgcctacc tcacatactc gctcggcttt gccgtcatgg gcctctacta   7440
ctatgctcct ctctttgtct ttgcttcgtt cctcgtcatt actaccttct tgcatcacaa   7500
cgacgaagct actccctggt acggtgactc ggagtggacc tacgtcaagg gcaacctgag   7560
ctccgtcgac cgatcgtacg gagctttcgt ggacaacctg tctcaccaca ttggcaccca   7620
ccaggtccat cacttgttcc ctatcattcc ccactacaag ctcaacgaag ccaccaagca   7680
ctttgctgcc gcttaccctc acctcgtgag acgtaacgac gagcccatca ttactgcctt   7740
cttcaagacc gctcacctct ttgtcaacta cggagctgtg cccgagactg ctcagatttt   7800
cacccctcaa agagtctgccg ctgcagccaa ggccaagagc gactaagcgg ccgcaagtgt   7860
ggatgggaa gtgagtgccc ggttctgtgt gcacaattgg caatccaaga tggatggatt   7920
caacacaggg atatagcgag ctacgtggtg gtgcgaggat atagcaacgg atatttatgt   7980
ttgacacttg agaatgtacg atacaagcac tgtccaagta caatactaaa catactgtac   8040
atactcatac tcgtacccgg gcaacggttt cacttgagtg cagtggctag tgctcttact   8100
```

-continued

| cgtacagtgt gcaatactgc gtatcatagt ctttgatgta tatcgtattc attcatgtta | 8160 |
| gttgc | 8165 |

<210> SEQ ID NO 23
<211> LENGTH: 8438
<212> TYPE: DNA
<213> ORGANISM: Artificial Sequence
<220> FEATURE:
<223> OTHER INFORMATION: Plasmid pDMW367

<400> SEQUENCE: 23

| catggctctc agtcttacca cagaacagct gttagaacgc cctgatttgg ttgcgattga | 60 |
| tggcatcctc tacgaccttg aagggcttgc caaagttcat ccaggaggag atttgattct | 120 |
| cgcttctggt gcctctgatg cctcccctct cttttattca atgcatccat acgtcaaacc | 180 |
| ggagaattcc aaaattgctt caacagttcgt ccgagggaag catgaccgca cctcgaagga | 240 |
| cattgtctac acgtatgatt ctcccttcgc acaagacgtt aagcggacaa tgcgcgaggt | 300 |
| gatgaaaggg aggaactggt acgcaacccc tggcttctgg ctgcgcaccg ttgggatcat | 360 |
| cgccgtgacg gccttttgcg agtggcactg ggctaccacg gggatggtgc tgtggggcct | 420 |
| gttgactgga ttcatgcaca tgcagatcgg cttatccatc cagcatgatg cgtcccacgg | 480 |
| ggccatcagc aagaagcctt gggtcaacgc cctcttcgcc tacggcattg acgtcatcgg | 540 |
| atcgtcccgg tggatttggc tgcagtcgca catcatgcgg caccacacct acaccaacca | 600 |
| gcacggcctc gacctggatg cggagtcggc agagccgttc ctggtgttcc acaactaccc | 660 |
| cgccgcaaac accgcccgaa agtggttcca ccgcttccaa gcttggtaca tgtaccttgt | 720 |
| gctggggca tacggggtat cgctggtgta caacccgctc tacattttcc ggatgcagca | 780 |
| caatgacacc atcccagagt ctgtcacggc catgcgggaa aatggctttc tgcggcgcta | 840 |
| ccgcacactt gcattcgtga tgcgagcttt cttcatcttc cggaccgcat tcttgccctg | 900 |
| gtacctcact gggacctcat tgctgatcac cattcctctg gtgcccaccg caactggtgc | 960 |
| cttcttgacg ttcttcttca ttttgtccca caattttgat ggctccgaac ggatccccga | 1020 |
| caagaactgc aaggttaaga gatctgagaa ggacgttgag gctgaccaaa ttgactggta | 1080 |
| tcgggcgcag gtggagacgt cctccacata cggtggcccc atcgccatgt tcttcactgg | 1140 |
| cggtctcaat ttccagatcg agcaccacct cttttccccg gatgtcgtctt ggcactaccc | 1200 |
| cttcgtccag caggcggtcc gggagtgttg cgaacgccat ggagtgcgat atgttttcta | 1260 |
| ccctaccatc gtcggcaaca tcatctccac cctgaagtac atgcataagg tgggtgtcgt | 1320 |
| ccactgcgtg aaggacgcac aggattccta agcggccgca agtgtggatg gggaagtgag | 1380 |
| tgcccggttc tgtgtgcaca attggcaatc aagatggat ggattcaaca cagggatata | 1440 |
| gcgagctacg tggtggtgcg aggatatagc aacggatatt tatgtttgac acttgagaat | 1500 |
| gtacgataca agcactgtcc aagtacaata ctaaacatac tgtacatact catactcgta | 1560 |
| cccgggcaac ggtttcactt gagtgcagtg gctagtgctc ttactcgtac agtgtgcaat | 1620 |
| actgcgtatc atagtctttg atgtatatcg tattcattca tgttagttgc gtacgagccg | 1680 |
| gaagcataaa gtgtaaagcc tggggtgcct aatgagtgag ctaactcaca ttaattgcgt | 1740 |
| tgcgctcact gcccgctttc cagtcgggaa acctgtcgtg ccagctgcat taatgaatcg | 1800 |
| gccaacgcgc ggggagaggc ggtttgcgta ttgggcgctc ttccgcttcc tcgctcactg | 1860 |
| actcgctgcg ctcggtcgtt cggctgcggc gagcggtatc agctcactca aaggcggtaa | 1920 |

```
tacggttatc cacagaatca ggggataacg caggaaagaa catgtgagca aaaggccagc    1980
aaaaggccag gaaccgtaaa aaggccgcgt tgctggcgtt tttccatagg ctccgccccc    2040
ctgacgagca tcacaaaaat cgacgctcaa gtcagaggtg gcgaaaccog acaggactat    2100 aaagatacca ggcgtttccc cctggaagct ccctcgtgcg ctctcctgtt ccgaccctgc    2160
cgcttaccgg atacctgtcc gcctttctcc cttcgggaag cgtggcgctt tctcatagct    2220
cacgctgtag gtatctcagt tcggtgtagg tcgttcgctc caagctgggc tgtgtgcacg    2280
aaccccccgt tcagcccgac cgctgcgcct tatccggtaa ctatcgtctt gagtccaacc    2340
cggtaagaca cgacttatcg ccactggcag cagccactgg taacaggatt agcagagcga    2400
ggtatgtagg cggtgctaca gagttcttga agtggtggcc taactacggc tacactagaa    2460
ggacagtatt tggtatctgc gctctgctga agccagttac cttcggaaaa agagttggta    2520
gctcttgatc cggcaaacaa accaccgctg gtagcggtgg tttttttgtt tgcaagcagc    2580
agattacgcg cagaaaaaaa ggatctcaag aagatccttt gatcttttct acggggtctg    2640
acgctcagtg gaacgaaaac tcacgttaag ggattttggt catgagatta tcaaaaagga    2700
tcttcaccta gatccttttaa aattaaaaat gaagttttaa atcaatctaa agtatatatg    2760
agtaaacttg gtctgacagt taccaatgct taatcagtga ggcacctatc tcagcgatct    2820
gtctatttcg ttcatccata gttgcctgac tccccgtcgt gtagataact acgatacggg    2880
agggcttacc atctggcccc agtgctgcaa tgataccgcg agacccacgc tcaccggctc    2940
cagatttatc agcaataaac cagccagccg gaagggccga gcgcagaagt ggtcctgcaa    3000
ctttatccgc ctccatccag tctattaatt gttgccggga agctagagta agtagttcgc    3060
cagttaatag tttgcgcaac gttgttgcca ttgctacagg catcgtggtg tcacgctcgt    3120
cgtttggtat ggcttcattc agctccggtt cccaacgatc aaggcgagtt acatgatccc    3180
ccatgttgtg caaaaaagcg gttagctcct tcggtcctcc gatcgttgtc agaagtaagt    3240
tggccgcagt gttatcactc atggttatgg cagcactgca taattctctt actgtcatgc    3300
catccgtaag atgcttttct gtgactggtg agtactcaac caagtcattc tgagaatagt    3360
gtatgcggcg accgagttgc tcttgcccgg cgtcaatacg ggataatacc gcgccacata    3420
gcagaacttt aaaagtgctc atcattggaa aacgttcttc ggggcgaaaa ctctcaagga    3480
tcttaccgct gttgagatcc agttcgatgt aacccactcg tgcacccaac tgatcttcag    3540
catcttttac tttcaccagc gtttctgggt gagcaaaaac aggaaggcaa aatgccgcaa    3600
aaaagggaat aagggcgaca cggaaatgtt gaatactcat actcttcctt tttcaatatt    3660
attgaagcat ttatcagggt tattgtctca tgagcggata catatttgaa tgtatttaga    3720
aaaataaaca aataggggtt ccgcgcacat ttccccgaaa agtgccacct gacgcgcccc    3780
gtagcggcgc attaagcgcg gcgggtgtgg tggttacgcg cagcgtgacc gctacacttg    3840
ccagcgccct agcgcccgct cctttcgctt tcttcccttc ctttctcgcc acgttcgccg    3900
gctttccccg tcaagctcta aatcgggggc tccctttagg gttccgattt agtgctttac    3960
ggcacctcga ccccaaaaaa cttgattagg gtgatggttc acgtagtggg ccatcgccct    4020
gatagacggt ttttcgccct ttgacgttgg agtccacgtt ctttaatagt ggactcttgt    4080
tccaaactgg aacaacactc aaccctatct cggtctattc ttttgattta agggattt    4140 tgccgatttc ggcctattgg ttaaaaaatg agctgattta acaaaaattt aacgcgaatt    4200
ttaacaaaat attaacgctt acaatttcca ttcgccattc aggctgcgca actgttggga    4260
agggcgatcg gtgcgggcct cttcgctatt acgccagctg gcgaaagggg gatgtgctgc    4320
```

```
aaggcgatta agttgggtaa cgccagggtt ttcccagtca cgacgttgta aaacgacggc    4380
cagtgaattg taatacgact cactataggg cgaattgggt accgggcccc ccctcgaggt    4440
cgatggtgtc gataagcttg atatcgaatt catgtcacac aaaccgatct tcgcctcaag    4500
gaaacctaat tctacatccg agagactgcc gagatccagt ctacactgat taattttcgg    4560
gccaataatt taaaaaaatc gtgttatata atattatatg tattatatat atacatcatg    4620
atgatactga cagtcatgtc ccattgctaa atagacagac tccatctgcc gcctccaact    4680
gatgttctca atatttaagg ggtcatctcg cattgtttaa taataaacag actccatcta    4740
ccgcctccaa atgatgttct caaaatatat tgtatgaact tatttttatt acttagtatt    4800
attagacaac ttacttgctt tatgaaaaac acttcctatt taggaaacaa tttataatgg    4860
cagttcgttc atttaacaat ttatgtagaa taaatgttat aaatgcgtat gggaaatctt    4920
aaatatggat agcataaatg atatctgcat tgcctaattc gaaatcaaca gcaacgaaaa    4980
aaatcccttg tacaacataa atagtcatcg agaaatatca actatcaaag aacagctatt    5040
cacacgttac tattgagatt attattggac gagaatcaca cactcaactg tctttctctc    5100
ttctagaaat acaggtacaa gtatgtacta ttctcattgt tcatacttct agtcatttca    5160
tcccacatat tccttggatt tctctccaat gaatgacatt ctatcttgca aattcaacaa    5220
ttataataag ataccaaa gtagcggtat agtggcaatc aaaaagcttc tctggtgtgc    5280
ttctcgtatt tatttttatt ctaatgatcc attaaaggta tatatttatt tcttgttata    5340 taatccttt gttattaca tgggctggat acataaaggt attttgattt aattttttgc    5400
ttaaattcaa tccccctcg ttcagtgtca actgtaatgg taggaaatta ccatactttt    5460
gaagaagcaa aaaaatgaa agaaaaaaa atcgtatttt ccaggttaga cgttccgcag    5520
aatctagaat gcggtatgcg gtacattgtt cttcgaacgt aaaagttgcg ctccctgaga    5580
tattgtacat ttttgctttt acaagtacaa gtacatcgta caactatgta ctactgttga    5640
tgcatccaca acagtttgtt ttgttttttt ttgtttttt tttttctaat gattcattac    5700
cgctatgtat acctacttgt acttgtagta agccgggtta ttggcgttca attaatcata    5760
gacttatgaa tctgcacggt gtgcgctgcg agttacttt agcttatgca tgctacttgg    5820
gtgtaatatt gggatctgtt cggaaatcaa cggatgctca atcgatttcg acagtaatta    5880
attaagtcat acacaagtca gctttcttcg agcctcatat aagtataagt agttcaacgt    5940
attagcactg tacccagcat ctccgtatcg agaaacacaa caacatgccc cattggacag    6000
atcatgcgga tacacaggtt gtgcagtatc atacatactc gatcagacag gtcgtctgac    6060
catcatacaa gctgaacaag cgctccatac ttgcacgctc tctatataca cagttaaatt    6120
acatatccat agtctaacct ctaacagtta atcttctggt aagcctccca gccagccttc    6180
tggtatcgct tggcctcctc aataggatct cggttctggc cgtacagacc tcggccgaca    6240
attatgatat ccgttccggt agacatgaca tcctcaacag ttcggtactg ctgtccgaga    6300
gcgtctccct tgtcgtcaag acccaccccg ggggtcagaa taagccagtc ctcagagtcg    6360
cccttaggtc ggttctgggc aatgaagcca accacaaact cggggtcgga tcgggcaagc    6420
tcaatggtct gcttggagta ctcgccagtg gccagagagc ccttgcaaga cagctcggcc    6480
agcatgagca gacctctggc cagcttctcg ttgggagagg ggactaggaa ctccttgtac    6540
tgggagttct cgtagtcaga gacgtcctcc ttcttctgtt cagagacagt ttcctcggca    6600
ccagctcgca ggccagcaat gattccggtt ccgggtacac cgtgggcgtt ggtgatatcg    6660
```

```
gaccactcgg cgattcggtg acaccggtac tggtgcttga cagtgttgcc aatatctgcg    6720
aactttctgt cctcgaacag aagaaaccg tgcttaagag caagttcctt gagggggagc    6780
acagtgccgg cgtaggtgaa gtcgtcaatg atgtcgatat gggttttgat catgcacaca    6840
taaggtccga ccttatcggc aagctcaatg agctccttgg tggtggtaac atccagagaa    6900
gcacacaggt tggttttctt ggctgccacg agcttgagca ctcgagcggc aaaggcggac    6960
ttgtggacgt tagctcgagc ttcgtaggag ggcattttgg tggtgaagag gagactgaaa    7020
taaatttagt ctgcagaact ttttatcgga accttatctg gggcagtgaa gtatatgtta    7080
tggtaatagt tacgagttag ttgaacttat agatagactg gactatacgg ctatcggtcc    7140
aaattagaaa gaacgtcaat ggctctctgg gcgtcgcctt tgccgacaaa aatgtgatca    7200
tgatgaaagc cagcaatgac gttgcagctg atattgttgt cggccaaccg cgccgaaaac    7260
gcagctgtca gacccacagc ctccaacgaa gaatgtatcg tcaaagtgat ccaagcacac    7320
tcatagttgg agtcgtactc caaaggcggc aatgacgagt cagacagata ctcgtcgact    7380
caggcgacga cggaattcct gcagcccatc tgcagaattc aggagagacc gggttggcgg    7440
cgtatttgtg tcccaaaaaa cagccccaat tgccccggag aagacggcca ggccgcctag    7500
atgacaaatt caacaactca cagctgactt tctgccattg ccactagggg ggggcctttt    7560
tatatggcca agccaagctc tccacgtcgg ttgggctgca cccaacaata aatgggtagg    7620
gttgcaccaa caaagggatg ggatgggggg tagaagatac gaggataacg gggctcaatg    7680
gcacaaataa gaacgaatac tgccattaag actcgtgatc cagcgactga caccattgca    7740
tcatctaagg gcctcaaaac tacctcggaa ctgctgcgct gatctggaca ccacagaggt    7800
tccgagcact ttaggttgca ccaaatgtcc caccaggtgc aggcagaaaa cgctggaaca    7860
gcgtgtacag tttgtcttaa caaaaagtga gggcgctgag gtcgagcagg gtggtgtgac    7920
ttgttatagc ctttagagct gcgaaagcgc gtatggattt ggctcatcag gccagattga    7980
gggtctgtgg acacatgtca tgttagtgta cttcaatcgc ccctggata tagccccgac    8040 aataggccgt ggcctcattt ttttgccttc cgcacatttc cattgctcgg tacccacacc    8100
ttgcttctcc tgcacttgcc aaccttaata ctggtttaca ttgaccaaca tcttacaagc    8160 gggggggcttg tctagggtat atataaacag tggctctccc aatcggttgc cagtctcttt    8220
tttcctttct ttccccacag attcgaaatc taaactacac atcacacaat gcctgttact    8280
gacgtcctta agcgaaagtc cggtgtcatc gtcggcgacg atgtccgagc cgtgagtatc    8340
cacgacaaga tcagtgtcga gacgacgcgt tttgtgtaat gacacaatcc gaaagtcgct    8400
agcaacacac actctctaca caaactaacc cagctctc                            8438
```

<210> SEQ ID NO 24
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 24

```
taaccctcac taagggaac aaaagctgga gctccaccgc ggacacaata tctggtcaaa     60
```

-continued

```
tttcagtttc gttacataaa tcgttatgtc aaaggagtgt gggaggttaa gagaattatc    120
accggcaaac tatctgttaa ttgctaggta cctctagacg tccacccggg tcgcttggcg    180
gccgaagagg ccggaatctc gggccgcggt ggcggccgct tagttggtct tggacttctt    240
gggcttcttc aggtaggact ggacaaagaa gttgccgaac agagcgagca gggtgatcat    300
gtacacgccg agcagctgga ccagagcctg agggtagtcg caggggaaga ggtagtcgta    360
cagggactgc accagcatag ccatgaactg ggtcatctgc agagtggtga tgtagggctt    420
gatgggcttg acgaagccga agccctgaga ggaaaagaag tagtaggcgt acatgacggt    480
gtggacgaag gagttgagga tgacggagaa gtaggcgtcg ccaccaggag cgtacttggc    540
aatagcccac cagatggcga agatggtggc atggtggtac acgtgcagga aggagacctg    600
gttgaacttc ttgcacagga tcatgatagc ggtgtccagg aactcgtagg ccttggagac    660
gtagaacacg tagacgattc gggacatgcc ctgagcgtgg gactcgttgc ccttctccat    720
gtcgttgccg aagaccttgt agccacccag gatagcctgt cggatggtct cgacgcacat    780
gtagagggac agtccgaaga ggaacaggtt gtggagcagc ttgatggtct tcagctcgaa    840
gggcttctcc atctgcttca tgatgggaat gccgaagagc agcatggcca tgtagccgac    900
ctcgaaggcg agcatggtgg agacgtccat catgggcaga ccgtcggtca gagcgtaggg    960
cttagctccg tccatccact ggtcgacacc ggtctcgact cgtccgacca cgtcgtccca   1020
gacagaggag ttggccatgg tgaatgattc ttatactcag aaggaaatgc ttaacgattt   1080
cgggtgtgag ttgacaagga gagagagaaa agaagaggaa aggtaattcg gggacggtgg   1140
tcttttatac ccttggctaa agtcccaacc acaaagcaaa aaaattttca gtagtctatt   1200
ttgcgtccgg catgggttac ccggatggcc agacaaagaa actagtacaa agtctgaaca   1260
agcgtagatt ccagactgca gtaccctacg cccttaacgg caagtgtggg aaccggggga   1320
ggtttgatat gtggggtgaa gggggctctc gccggggttg ggcccgctac tgggtcaatt   1380
tggggtcaat ggggcaattg gggctgtttt tttgggacac aaatacgccg ccaacccggt   1440
ctctcctgaa ttctgcatcg atcgaggaag aggacaagcg gctgcttctt aagtttgtga   1500
catcagtatc caaggcacca ttgcaaggat tcaaggcttt gaacccgtca tttgccattc   1560
gtaacgctgg tagacaggtt gatcggttcc ctacggcctc cacctgtgtc aatcttctca   1620
agctgcctga ctatcaggac attgatcaac ttcggaagaa acttttgtat gccattcgat   1680
cacatgctgt tttcgatttg tcttagagga acgcatatac agtaatcata gagaataaac   1740
gatattcatt tattaaagta gatagttgag gtagaagttg taaagagtga taaatagcgg   1800
ccgcgcctac ttaagcaacg ggcttgataa cagcggggggg ggtgcccacg ttgttgcggt   1860
tgcggaagaa cagaacaccc ttaccagcac cctcggcacc agcgctgggc tcaacccact   1920
ggcacatacg cgcactgcgg tacatggcgc ggatgaagcc acgaggacca tcctggacat   1980
cagcccggta gtgcttgccc atgatgggct taatggcctc ggtggcctcg tccgcgttgt   2040
agaaggggat gctgctgacg tagtggtgga ggacatgagt ctcgatgatg ccgtggagaa   2100
ggtggcggcc gatgaagccc atctcacggt caatggtagc agcggcacca cggacgaagt   2160
tccactcgtc gttggtgtag tggggaaggg tagggtcggt gtgctggagg aaggtgatgg   2220
caacgagcca gtggttaacc cagaggtagg gaacaaagta ccagatggcc atgttgtaga   2280
aaccgaactt ctgaacgagg aagtacagag cagtggccat cagaccgata ccaatatcgc   2340
tgaggacgat gagcttagcg tcactgttct cgtacagagg gctgcgggga tcgaagtggt   2400
```

```
taacaccacc gccgaggccg ttatgcttgc ccttgccgcg accctcacgc tggcgctcgt    2460
ggtagttgtg gccggtaaca ttggtgatga ggtagttggg ccagccnacg annnnctcag    2520
taagatgagc gagctcgtgg gtcatctttc cgagacgagt agcctgctgc tcgcgggttc    2580
ggggaacgaa gaccatgtca cgctccatgt tgccagtggc cttgtggtgc tttcggtggg    2640
agatttgcca gctgaagtag gggacaagga gggaagagtg aagaacccag ccagtaatgt    2700
cgttgatgat gcgagaatcg gagaaagcac cgtgaccgca ctcatgggca ataacccaga    2760
gaccagtacc gaaaagaccc tgaagaacgg tgtacacggc ccacagacca gcgcgggcgg    2820
gggtggaggg gatatattcg ggggtcacaa agttgtacca gatgctgaaa gtggtagtca    2880
ggaggacaat gtcgcggagg atataaccgt atcccttgag agcggagcgc ttgaagcagt    2940
gcttagggat ggcattgtag atgtccttga tggtaaagtc gggaacctcg aactggttgc    3000
cgtaggtgtc gagcatgaca ccatactcgg acttgggctt ggcgatatca acctcggaca    3060
tggacgagag cgatgtggaa gaggccgagt ggcggggaga gtctgaagga gagacggcgg    3120
cagactcaga atccgtcaca gtagttgagg tgacggtgcg tctaagcgca gggttctgct    3180
tgggcagagc cgaagtggac gccatggaga gctgggttag tttgtgtaga gagtgtgtgt    3240
tgctagcgac tttcggattg tgtcattaca caaaacgcgt cgtctcgaca ctgatcttgt    3300
cgtggatact cacggctcgg acatcgtcgc cgacgatgac accggacttt cgcttaagga    3360
cgtcagtaac aggcattgtg tgatgtgtag tttagatttc gaatctgtgg ggaaagaaag    3420
gaaaaaagag actggcaacc gattgggaga gccactgttt atatataccc tagacaagcc    3480
ccccgcttgt aagatgttgg tcaatgtaaa ccagtattaa ggttggcaag tgcaggagaa    3540
gcaaggtgtg ggtaccgagc aatggaaatg tgcggaaggc aaaaaaatga ggccacggcc    3600
tattgtcggg gctatatcca gggggcgatt gaagtacact aacatgacat gtgtccacag    3660
accctcaatc tggcctgatg agccaaatcc atacgcgctt tcgcagctct aaaggctata    3720
acaagtcaca ccaccctgct cgacctcagc gccctcactt tttgttaaga caaactgtac    3780
acgctgttcc agcgttttct gcctgcacct ggtgggacat ttggtgcaac ctaaagtgct    3840
cggaacctct gtggtgtcca gatcagcgca gcagttccga ggtagttttg aggcccttag    3900
atgatgcaat ggtgtcagtc gctggatcac gagtcttaat ggcagtattc gttcttattt    3960
gtgccattga gccccgttat cctcgtatct tctaccccc atcccatccc tttgttggtg    4020
caaccctacc catttattgt tgggtgcagc ccaaccgacg tggagagctt ggcttggcca    4080
tataaaaagg ccccccccta gtggcaatgg cagaaagtca gctgtgagtt gttgaatttg    4140
tcatctaggc ggcctggccg tcttctccgg ggcaattgtt cctctatagt actgcgtaca    4200
ctgtttaaac agtgtacgca gatctgcgac gacggaattc ctgcagccca tctgcagaat    4260
tcaggagaga ccgggttggc ggcgtatttg tgtcccaaaa aacagcccca attgcccaa    4320
ttgaccccaa attgacccag tagcgggccc aaccccggcg agagcccct tcaccccaca    4380
tatcaaacct ccccggttc ccacacttgc cgttaagggc gtagggtact gcagtctgga    4440
atctacgctt gttcagactt tgtactagtt tctttgtctg gccatccggg taacccatgc    4500
cggacgcaaa atagactact gaaaattttt ttgctttgtg gttgggactt tagccaaggg    4560
tataaaagac caccgtcccc gaattacctt tcctcttctt ttctctctct ccttgtcaac    4620
tcacacccga aatcgttaag catttccttc tgagtataag aatcattcac catggctgcc    4680
gctccctctg tgcgaacctt tacccgagcc gaggttctga acgctgaggc tctgaacgag    4740
ggcaagaagg acgctgaggc tcccttcctg atgatcatcg acaacaaggt gtacgacgtc    4800
```

-continued

```
cgagagttcg tccctgacca tcctggaggc tccgtgattc tcacccacgt tggcaaggac    4860
ggcaccgacg tctttgacac ctttcatccc gaggctgctt gggagactct cgccaacttc    4920
tacgttggag acattgacga gtccgaccga gacatcaaga acgatgactt tgccgctgag    4980
gtccgaaagc tgcgaaccct gttccagtct ctcggctact acgactcctc taaggcctac    5040
tacgccttca aggtctcctt caacctctgc atctggggac tgtccaccgt cattgtggcc    5100
aagtggggtc agacctccac cctcgccaac gtgctctctg ctgccctgct cggcctgttc    5160
tggcagcagt gcggatggct ggctcacgac tttctgcacc accaggtctt ccaggaccga    5220
ttctggggtg atctcttcgg agccttcctg ggaggtgtct gccagggctt ctcctcttcc    5280
tggtggaagg acaagcacaa cactcaccat gccgctccca acgtgcatgg cgaggatcct    5340
gacattgaca cccacccTct cctgacctgg tccgagcacg ctctggagat gttctccgac    5400
gtccccgatg aggagctgac ccgaatgtgg tctcgattca tggtcctgaa ccagacctgg    5460
ttctacttcc ccattctctc cttcgctcga ctgtcttggt gcctccagtc cattctcttt    5520
gtgctgccca acgtcaggc tcacaagccc tccggagctc gagtgcccat ctccctggtc    5580
gagcagctgt ccctcgccat gcactggacc tggtacctcg ctaccatgtt cctgttcatc    5640
aaggatcctg tcaacatgct cgtgtacttc ctggtgtctc aggctgtgtg cggaaacctg    5700
ctcgccatcg tgttctccct caaccacaac ggtatgcctg tgatctccaa ggaggaggct    5760
gtcgacatgg atttctttac caagcagatc atcactggtc gagatgtcca tcctggactg    5820
ttcgccaact ggttcaccgg tggcctgaac taccagatcg agcatcacct gttcccttcc    5880
atgcctcgac acaacttctc caagatccag cctgccgtcg agaccctgtg caagaagtac    5940
aacgtccgat accacaccac tggtatgatc gagggaactg ccgaggtctt ctcccgactg    6000
aacgaggtct ccaaggccac ctccaagatg gcaaggctc agtaagcggc cgcatgagaa    6060
gataaatata taaatacatt gagatattaa atgcgctaga ttagagagcc tcatactgct    6120
cggagagaag ccaagacgag tactcaaagg ggattacacc atccatatcc acagacacaa    6180
gctggggaaa ggttctatat acactttccg gaataccgta gtttccgatg ttatcaatgg    6240
gggcagccag gatttcaggc acttcggtgt ctcggggtga atggcgttc ttggcctcca    6300
tcaagtcgta ccatgtcttc atttgcctgt caaagtaaaa cagaagcaga tgaagaatga    6360
acttgaagtg aaggaattta aattgccccg gagaagacgg ccaggccgcc tagatgacaa    6420
attcaacaac tcacagctga cttttctgcca ttgccactag gggggggcct ttttatatgg    6480
ccaagccaag ctctccacgt cggttgggct gcacccaaca ataaatgggt agggttgcac    6540
caacaaaggg atgggatggg gggtagaaga tacgaggata acggggctca atggcacaaa    6600
taagaacgaa tactgccatt aagactcgtg atccagcgac tgacaccatt gcatcatcta    6660
agggcctcaa aactacctcg gaactgctgc gctgatctgg acaccacaga ggttccgagc    6720
actttaggtt gcaccaaatg tcccaccagg tgcaggcaga aaacgctgga acagcgtgta    6780
cagtttgtct taacaaaaag tgagggcgct gaggtcgagc agggtggtgt gacttgttat    6840
agcctttaga gctgcgaaag cgcgtatgga tttggctcat caggccagat tgagggtctg    6900
tggacacatg tcatgttagt gtacttcaat cgccccctgg atatagcccc gacaataggc    6960
cgtggcctca tttttttgcc ttccgcacat ttccattgct cggtacccac accttgcttc    7020
tcctgcactt gccaacctta atactggttt acattgacca acatcttaca agcgggggc    7080
ttgtctaggg tatatataaa cagtggctct cccaatcggt tgccagtctc ttttttcctt    7140
```

```
tctttcccca cagattcgaa atctaaacta cacatcacac aatgccctgtt actgacgtcc   7200
ttaagcgaaa gtccggtgtc atcgtcggcg acgatgtccg agccgtgagt atccacgaca   7260
agatcagtgt cgagacgacg cgttttgtgt aatgacacaa tccgaaagtc gctagcaaca   7320
cacactctct acacaaacta acccagctct ccatggagtc cattgctccc ttcctgccct   7380
ccaagatgcc tcaggacctg ttcatggacc tcgccagcgc tatcggtgtc cgagctgctc   7440
cctacgtcga tcccctggag gctgcccctgg ttgcccaggc cgagaagtac attcccacca   7500
ttgtccatca cactcgaggc ttcctggttg ccgtggagtc tccctggct cgagagctgc   7560
ctctgatgaa ccccttccac gtgctcctga tcgtgctcgc ctacctggtc accgtgtttg   7620
tgggtatgca gatcatgaag aactttgaac gattcgaggt caagaccttc tccctcctgc   7680
acaacttctg tctggtctcc atctccgcct acatgtgcgg tggcatcctg tacgaggctt   7740
atcaggccaa ctatggactg tttgagaacg ctgccgatca caccttcaag ggtctcccta   7800
tggctaagat gatctggctc ttctacttct ccaagatcat ggagtttgtc gacaccatga   7860
tcatggtcct caagaagaac aaccgacaga tttccttttct gcacgtgtac caccactctt   7920
ccatcttcac catctggtgg ctggtcacct tcgttgctcc caacggtgaa gcctacttct   7980
ctgctgccct gaactccttc atccacgtca tcatgtacgg ctactacttt ctgtctgccc   8040
tgggcttcaa gcaggtgtcg ttcatcaagt tctacatcac tcgatcccag atgacccagt   8100
tctgcatgat gtctgtccag tcttcctggg acatgtacgc catgaaggtc cttggccgac   8160
ctggataccc cttcttcatc accgctctgc tctggttcta catgtggacc atgctcggtc   8220
tcttctacaa cttttaccga aagaacgcca agctcgccaa gcaggccaag gctgacgctg   8280
ccaaggagaa ggccagaaag ctccagtaag cggccgcaag tgtggatggg gaagtgagtg   8340
cccggttctg tgtgcacaat tggcaatcca agatggatgg attcaacaca gggatatagc   8400
gagctacgtg gtggtgcgag gatatagcaa cggatattta tgtttgacac ttgagaatgt   8460
acgatacaag cactgtccaa gtacaatact aaacatactg tacatactca tactcgtacc   8520
cgggcaacgg tttcacttga gtgcagtggc tagtgctctt actcgtacag tgtgcaatac   8580
tgcgtatcat agtctttgat gtatatcgta ttcattcatg ttagttgcgt acgaagtcgt   8640
caatgatgtc gatatgggtt tgatcatgc acacataagg tccgacctta tcggcaagct   8700
caatgagctc cttggtggtg gtaacatcca gagaagcaca caggttggtt ttcttggctg   8760
ccacgagctt gagcactcga gcggcaaagg cggacttgtg gacgttagct cgagcttcgt   8820
aggagggcat tttggtggtg aagaggagac tgaaataaat ttagtctgca gaactttttta   8880
tcggaacctt atctggggca gtgaagtata tgttatggta atagttacga gttagttgaa   8940
cttatagata gactggacta tacggctatc ggtccaaatt agaaagaacg tcaatggctc   9000
tctgggcgtc gcctttgccg acaaaaatgt gatcatgatg aaagccagca atgacgttgc   9060
agctgatatt gttgtcggcc aaccgcgccg aaaacgcagc tgtcagaccc acagcctcca   9120
acgaagaatg tatcgtcaaa gtgatccaag cacactcata gttggagtcg tactccaaag   9180
gcggcaatga cgagtcagac agatactcgt cgacctttc cttgggaacc accaccgtca   9240
gcccttctga ctcacgtatt gtagccaccg acacaggcaa cagtccgtgg atagcagaat   9300
atgtcttgtc ggtccatttc tcaccaactt taggcgtcaa gtgaatgttg cagaagaagt   9360
atgtgccttc attgagaatc ggtgttgctg atttcaataa agtcttgaga tcagtttggc   9420
gcgccagctg cattaatgaa tcggccaacg cgcggggaga ggcggttttgc gtattgggcg   9480
ctcttccgct tcctcgctca ctgactcgct gcgctcggtc gttcggctgc ggcgagcggt   9540
```

```
atcagctcac tcaaaggcgg taatacggtt atccacagaa tcaggggata acgcaggaaa   9600
gaacatgtga gcaaaaggcc agcaaaaggc caggaaccgt aaaaaggccg cgttgctggc   9660
gtttttccat aggctccgcc ccctgacga gcatcacaaa aatcgacgct caagtcagag    9720
gtggcgaaac ccgacaggac tataaagata ccaggcgttt ccccctggaa gctccctcgt   9780
gcgctctcct gttccgaccc tgccgcttac cggatacctg tccgcctttc tcccttcggg   9840
aagcgtggcg ctttctcata gctcacgctg taggtatctc agttcggtgt aggtcgttcg   9900
ctccaagctg ggctgtgtgc acgaacccc cgttcagccc gaccgctgcg ccttatccgg    9960
taactatcgt cttgagtcca acccggtaag acacgactta tcgccactgg cagcagccac  10020
tggtaacagg attagcagag cgaggtatgt aggcggtgct acagagttct tgaagtggtg  10080
gcctaactac ggctacacta agaacagt atttggtatc tgcgctctgc tgaagccagt    10140
taccttcgga aaaagagttg gtagctcttg atccggcaaa caaaccaccg ctggtagcgg  10200
tggtttttt gtttgcaagc agcagattac gcgcagaaaa aaggatctc aagaagatcc    10260
tttgatcttt tctacggggt ctgacgctca gtggaacgaa aactcacgtt aagggatttt  10320
ggtcatgaga ttatcaaaaa ggatcttcac ctagatcctt ttaaattaaa aatgaagttt  10380
taaatcaatc taaagtatat atgagtaaac ttggtctgac agttaccaat gcttaatcag  10440
tgaggcacct atctcagcga tctgtctatt tcgttcatcc atagttgcct gactcccgt   10500
cgtgtagata actacgatac gggagggctt accatctggc cccagtgctg caatgatacc  10560
gcgagaccca cgctcaccgg ctccagattt atcagcaata aaccagccag ccggaagggc  10620
cgagcgcaga gtggtcctg caactttatc cgcctccatc cagtctatta attgttgccg   10680
ggaagctaga gtaagtagtt cgccagttaa tagtttgcgc aacgttgttg ccattgctac  10740
aggcatcgtg gtgtcacgct cgtcgtttgg tatggcttca ttcagctccg gttcccaacg  10800
atcaaggcga gttacatgat cccccatgtt gtgcaaaaaa gcggttagct ccttcggtcc  10860
tccgatcgtt gtcagaagta agttggccgc agtgttatca ctcatggtta tggcagcact  10920
gcataattct cttactgtca tgccatccgt aagatgcttt tctgtgactg gtgagtactc  10980
aaccaagtca ttctgagaat agtgtatgcg gcgaccgagt tgctcttgcc cggcgtcaat  11040
acgggataat accgcgccac atagcagaac tttaaaagtg ctcatcattg gaaaacgttc  11100
ttcggggcga aaactctcaa ggatcttacc gctgttgaga tccagttcga tgtaacccac  11160
tcgtgcaccc aactgatctt cagcatcttt tactttcacc agcgtttctg ggtgagcaaa  11220
aacaggaagg caaaatgccg caaaaaggg aataagggcg acacggaaat gttgaatact   11280
catactcttc ctttttcaat attattgaag catttatcag ggttattgtc tcatgagcgg  11340
atacatattt gaatgtattt agaaaaataa acaaataggg gttccgcgca catttccccg  11400
aaaagtgcca cctgatgcgg tgtgaaatac cgcacagatg cgtaaggaga aaataccgca  11460
tcaggaaatt gtaagcgtta atattttgtt aaaattcgcg ttaaattttt gttaaatcag  11520
ctcattttt aaccaatagg ccgaaatcgg caaaatccct tataaatcaa agaatagac    11580
cgagataggg ttgagtgttg ttccagtttg gaacaagagt ccactattaa agaacgtgga  11640
ctccaacgtc aaagggcgaa aaaccgtcta tcagggcgat ggcccactac gtgaaccatc  11700
accctaatca agttttttgg ggtcgaggtg ccgtaaagca ctaaatcgga acctaaagg   11760
gagcccccga tttagagctt gacggggaaa gccggcgaac gtggcgagaa aggaagggaa  11820
gaaagcgaaa ggagcgggcg ctagggcgct ggcaagtgta gcggtcacgc tgcgcgtaac  11880
```

-continued

```
caccacaccc gccgcgctta atgcgccgct acagggcgcg tccattcgcc attcaggctg    11940
cgcaactgtt gggaagggcg atcggtgcgg gcctcttcgc tattacgcca gctggcgaaa    12000
gggggatgtg ctgcaaggcg attaagttgg gtaacgccag ggttttccca gtcacgacgt    12060
tgtaaaacga cggccagtga attgtaatac gactcactat agggcgaatt gggcccgacg    12120
tcgcatgcag tggtggtatt gtgactgggg atgtagttga gaataagtca tacacaagtc    12180
agctttcttc gagcctcata taagtataag tagttcaacg tattagcact gtacccagca    12240
tctccgtatc gagaaacaca acaacatgcc ccattggaca gatcatgcgg atacacaggt    12300
tgtgcagtat catacatact cgatcagaca ggtcgtctga ccatcataca agctgaacaa    12360
gcgctccata cttgcacgct ctctatatac acagttaaat tacatatcca tagtctaacc    12420
tctaacagtt aatcttctgg taagcctccc agccagcctt ctggtatcgc ttggcctcct    12480
caataggatc tcggttctgg ccgtacagac ctcggccgac aattatgata tccgttccgg    12540
tagacatgac atcctcaaca gttcggtact gctgtccgag agcgtctccc ttgtcgtcaa    12600
gacccacccc gggggtcaga ataagccagt cctcagagtc gcccttaat                12649
```

<210> SEQ ID NO 25
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized) for
      Yarrowia lipolytica

<400> SEQUENCE: 25

```
atggccaact cctctgtctg ggacgacgtg gtcggacgag tcgagaccgg tgtcgaccag     60
tggatggacg gagctaagcc ctacgctctg accgacggtc tgcccatgat ggacgtctcc    120
accatgctcg ccttcgaggt cggctacatg gccatgctgc tcttcggcat tcccatcatg    180
aagcagatgg agaagccctt cgagctgaag accatcaagc tgctccacaa cctgttcctc    240
ttcggactgt ccctctacat gtgcgtcgag accatccgac aggctatcct gggtggctac    300
aaggtcttcg gcaacgacat ggagaagggc aacgagtccc acgctcaggg catgtcccga    360
atcgtctacg tgttctacgt ctccaaggcc tacgagttcc tggacaccgc tatcatgatc    420
ctgtgcaaga agttcaacca ggtctccttc ctgcacgtgt accaccatgc caccatcttc    480
gccatctggt gggctattgc caagtacgct cctggtggcg acgcctactt ctccgtcatc    540
ctcaactcct tcgtccacac cgtcatgtac gcctactact tcttttcctc tcagggcttc    600
ggcttcgtca gcccatcaa gccctacatc accactctgc agatgaccca gttcatggct    660
atgctggtgc agtccctgta cgactacctc ttccctgcg actaccctca ggctctggtc    720
cagctgctcg gcgtgtacat gatcacccty ctcgctctgt tcggcaactt ctttgtccag    780
tcctacctga agaagcccaa gaagtccaag accaactaa                           819
```

<210> SEQ ID NO 26
<211> LENGTH: 272
<212> TYPE: PRT
<213> ORGANISM: Thraustochytrium aureum

<400> SEQUENCE: 26

```
Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30
```

```
Gly Leu Pro Met Met Asp Val Ser Thr Met Leu Ala Phe Glu Val Gly
             35                  40                  45

Tyr Met Ala Met Leu Leu Phe Gly Ile Pro Ile Met Lys Gln Met Glu
 50                  55                  60

Lys Pro Phe Glu Leu Lys Thr Ile Lys Leu Leu His Asn Leu Phe Leu
 65                  70                  75                  80

Phe Gly Leu Ser Leu Tyr Met Cys Val Glu Thr Ile Arg Gln Ala Ile
                 85                  90                  95

Leu Gly Gly Tyr Lys Val Phe Gly Asn Asp Met Glu Lys Gly Asn Glu
                100                 105                 110

Ser His Ala Gln Gly Met Ser Arg Ile Val Tyr Val Phe Tyr Val Ser
                115                 120                 125

Lys Ala Tyr Glu Phe Leu Asp Thr Ala Ile Met Ile Leu Cys Lys Lys
                130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
                180                 185                 190

Tyr Phe Phe Ser Ser Gln Gly Phe Gly Phe Val Lys Pro Ile Lys Pro
                195                 200                 205

Tyr Ile Thr Thr Leu Gln Met Thr Gln Phe Met Ala Met Leu Val Gln
                210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
                260                 265                 270

<210> SEQ ID NO 27
<211> LENGTH: 20
<212> TYPE: DNA
<213> ORGANISM: Artificial Sequence
<220> FEATURE:
<223> OTHER INFORMATION: Primer 5-1A

<400> SEQUENCE: 27
gghcaycayr tbtayacaaa                                                   20

<210> SEQ ID NO 28
<211> LENGTH: 20
<212> TYPE: DNA
<213> ORGANISM: Artificial Sequence
<220> FEATURE:
<223> OTHER INFORMATION: Primer 5-1B

<400> SEQUENCE: 28
gghcaycayr tbtayaccaa                                                   20

<210> SEQ ID NO 29
<211> LENGTH: 20
<212> TYPE: DNA
<213> ORGANISM: Artificial Sequence
<220> FEATURE:
<223> OTHER INFORMATION: Primer 5-1C

<400> SEQUENCE: 29
```

```
gghcaycayr tbtayacgaa                                                20
```

<210> SEQ ID NO 30
<211> LENGTH: 20
<212> TYPE: DNA
<213> ORGANISM: Artificial Sequence
<220> FEATURE:
<223> OTHER INFORMATION: Primer 5-1D

<400> SEQUENCE: 30

```
gghcaycayr tbtayactaa                                                20
```

<210> SEQ ID NO 31
<211> LENGTH: 20
<212> TYPE: DNA
<213> ORGANISM: Artificial Sequence
<220> FEATURE:
<223> OTHER INFORMATION: Primer 5-5AR

<400> SEQUENCE: 31

```
tgrtgvacaa yytgrwartt                                                20
```

<210> SEQ ID NO 32
<211> LENGTH: 20
<212> TYPE: DNA
<213> ORGANISM: Artificial Sequence
<220> FEATURE:
<223> OTHER INFORMATION: Primer 5-5BR

<400> SEQUENCE: 32

```
tgrtgvacta yytgrwartt                                                20
```

<210> SEQ ID NO 33
<211> LENGTH: 20
<212> TYPE: DNA
<213> ORGANISM: Artificial Sequence
<220> FEATURE:
<223> OTHER INFORMATION: Primer 5-5CR

<400> SEQUENCE: 33

```
tgrtgvacca yytgrwartt                                                20
```

<210> SEQ ID NO 34
<211> LENGTH: 20
<212> TYPE: DNA
<213> ORGANISM: Artificial Sequence
<220> FEATURE:
<223> OTHER INFORMATION: Primer 5-5DR

<400> SEQUENCE: 34

```
tgrtgvacga yytgrwartt                                                20
```

<210> SEQ ID NO 35
<211> LENGTH: 27
<212> TYPE: DNA
<213> ORGANISM: Artificial Sequence
<220> FEATURE:
<223> OTHER INFORMATION: Primer ODMW480

<400> SEQUENCE: 35

```
ccgataccag tcaatttggt cagcctc                                        27
```

<210> SEQ ID NO 36
<211> LENGTH: 23
<212> TYPE: DNA

-continued

<213> ORGANISM: Artificial Sequence
<220> FEATURE:
<223> OTHER INFORMATION: CDSIII 5' primer

<400> SEQUENCE: 36
aagcagtggt atcaacgcag agt                                              23

<210> SEQ ID NO 37
<211> LENGTH: 28
<212> TYPE: DNA
<213> ORGANISM: Artificial Sequence
<220> FEATURE:
<223> OTHER INFORMATION: Primer ODMW479

<400> SEQUENCE: 37
cttaaccttg cagttcttgt cggggatc                                         28

<210> SEQ ID NO 38
<211> LENGTH: 22
<212> TYPE: DNA
<213> ORGANISM: Artificial Sequence
<220> FEATURE:
<223> OTHER INFORMATION: Primer DNR CDS 5'

<400> SEQUENCE: 38
caacgcagag tggccattac gg                                               22

<210> SEQ ID NO 39
<211> LENGTH: 27
<212> TYPE: DNA
<213> ORGANISM: Artificial Sequence
<220> FEATURE:
<223> OTHER INFORMATION: Primer YL791

<400> SEQUENCE: 39
cacctcgcgc attgtccgct taacgtc                                          27

<210> SEQ ID NO 40
<211> LENGTH: 27
<212> TYPE: DNA
<213> ORGANISM: Artificial Sequence
<220> FEATURE:
<223> OTHER INFORMATION: Primer YL792

<400> SEQUENCE: 40
tgcgaaggga gaatcatacg tgtagac                                          27

<210> SEQ ID NO 41
<211> LENGTH: 26
<212> TYPE: DNA
<213> ORGANISM: Artificial Sequence
<220> FEATURE:
<223> OTHER INFORMATION: Primer ODMW469

<400> SEQUENCE: 41
cttcatcttc cggaccgcat tcttgc                                           26

<210> SEQ ID NO 42
<211> LENGTH: 20
<212> TYPE: DNA
<213> ORGANISM: Artificial Sequence
<220> FEATURE:
<223> OTHER INFORMATION: Primer AUAP

<400> SEQUENCE: 42
ggccacgcgt cgactagtac                                                  20

<210> SEQ ID NO 43
<211> LENGTH: 28
<212> TYPE: DNA
<213> ORGANISM: Artificial Sequence
<220> FEATURE:
<223> OTHER INFORMATION: Primer ODMW470

<400> SEQUENCE: 43
cctcactggg acctcattgc tgatcacc                                          28

<210> SEQ ID NO 44
<211> LENGTH: 32
<212> TYPE: DNA
<213> ORGANISM: Artificial Sequence
<220> FEATURE:
<223> OTHER INFORMATION: Primer YL794

<400> SEQUENCE: 44
tttccatggc tctcagtctt accacagaac ag                                     32

<210> SEQ ID NO 45
<211> LENGTH: 27
<212> TYPE: DNA
<213> ORGANISM: Artificial Sequence
<220> FEATURE:
<223> OTHER INFORMATION: Primer YL797

<400> SEQUENCE: 45
gtacatgtac caagcttgga agcggtg                                           27

<210> SEQ ID NO 46
<211> LENGTH: 27
<212> TYPE: DNA
<213> ORGANISM: Artificial Sequence
<220> FEATURE:
<223> OTHER INFORMATION: Primer YL796

<400> SEQUENCE: 46
caccgcttcc aagcttggta catgtac                                           27

<210> SEQ ID NO 47
<211> LENGTH: 39
<212> TYPE: DNA
<213> ORGANISM: Artificial Sequence
<220> FEATURE:
<223> OTHER INFORMATION: Primer YL795

<400> SEQUENCE: 47
tttgcggccg cttaggaatc ctgtgcgtcc ttcacgcag                              39

<210> SEQ ID NO 48
<211> LENGTH: 4070
<212> TYPE: DNA
<213> ORGANISM: Artificial Sequence
<220> FEATURE:
<223> OTHER INFORMATION: Plasmid pEgD5S

<400> SEQUENCE: 48
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acctcgcgaa    420
tgcatctaga tccatggctc tctcccttac taccgagcag ctgctcgagc gacccgacct    480
ggttgccatc gacggcattc tctacgatct ggaaggtctt gccaaggtcc atcccggagg    540
cgacttgatc ctcgcttctg gtgcctccga tgcttctcct ctgttctact ccatgcaccc    600
ttacgtcaag cccgagaact cgaagctgct caacagttc gtgcgaggca agcacgaccg     660
aacctccaag gacattgtct acacctacga ctctcccttt gcacaggacg tcaagcgaac    720
tatgcgagag gtcatgaaag gtcggaactg gtatgccaca cctggattct ggctgcgaac    780
cgttggcatc attgctgtca ccgccttttg cgagtggcac tgggctacta ccggaatggt    840
gctgtggggt ctcttgactg gattcatgca catgcagatc ggcctgtcca ttcagcacga    900
tgcctctcat ggtgccatca gcaaaaagcc ctgggtcaac gctctctttg cctacggcat    960
cgacgtcatt ggatcgtcca gatggatctg gctgcagtct cacatcatgc gacatcacac    1020
ctacaccaat cagcatggtc tcgacctgga tgccgagtcc gcagaaccat tccttgtgtt    1080
ccacaactac cctgctgcca acactgctcg aaagtggttt caccgattcc aggcctggta    1140
catgtacctc gtgcttggag cctacggcgt ttcgctggtg tacaaccctc tctacatctt    1200
ccgaatgcag cacaacgaca ccattcccga gtctgtcaca gccatgcgag agaacggctt    1260
tctgcgacgg taccgaaccc ttgcattcgt tatgcgagct ttcttcatct ttcgaaccgc    1320
cttcttgccc tggtatctca ctggaacctc cctgctcatc accattcctc tggtgcccac    1380
tgctaccggt gccttcctca ccttcttttt catcttgtct cacaacttcg atggctcgga    1440
gcgaatcccc gacaagaact gcaaggtcaa gagctccgag aaggacgttg aagccgatca    1500
gatcgactgg tacagagctc aggtggagac ctcttccacc tacggtggac ccattgccat    1560
gttctttact ggcggtctca acttccagat cgagcatcac ctctttcctc gaatgtcgtc    1620
ttggcactat cccttcgtgc agcaagctgt ccgagagtgt tgcgaacgac acggagttcg    1680
gtacgtcttc taccctacca ttgtgggcaa catcatttcc accctcaagt acatgcacaa    1740
agtcggtgtg gttcactgtg tcaaggacgc tcaggattcc taagcggccg catcggatcc    1800
cgggcccgtc gactgcagag gcctgcatgc aagcttggcg taatcatggt catagctgtt    1860
tcctgtgtga aattgttatc cgctcacaat tccacacaac atacgagccg gaagcataaa    1920
gtgtaaagcc tggggtgcct aatgagtgag ctaactcaca ttaattgcgt tgcgctcact    1980
gcccgctttc cagtcgggaa acctgtcgtg ccagctgcat taatgaatcg gccaacgcgc    2040
ggggagaggc ggtttgcgta ttgggcgctc ttccgcttcc tcgctcactg actcgctgcg    2100
ctcggtcgtt cggctgcggc gagcggtatc agctcactca aaggcggtaa tacggttatc    2160
cacagaatca ggggataacg caggaaagaa catgtgagca aaaggccagc aaaaggccag    2220
gaaccgtaaa aaggccgcgt tgctggcgtt tttccatagg ctccgccccc ctgacgagca    2280
tcacaaaaat cgacgctcaa gtcagaggtg gcgaaacccg acaggactat aaagatacca    2340
ggcgtttccc cctggaagct ccctcgtgcg ctctcctgtt ccgaccctgc cgcttaccgg    2400
atacctgtcc gcctttctcc cttcgggaag cgtggcgctt tctcatagct cacgctgtag    2460
gtatctcagt tcggtgtagg tcgttcgctc caagctgggc tgtgtgcacg aaccccccgt    2520
tcagcccgac cgctgcgcct tatccggtaa ctatcgtctt gagtccaacc cggtaagaca    2580
cgacttatcg ccactggcag cagccactgg taacaggatt agcagagcga ggtatgtagg    2640
```

-continued

```
cggtgctaca gagttcttga agtggtggcc taactacggc tacactagaa gaacagtatt    2700
tggtatctgc gctctgctga agccagttac cttcggaaaa agagttggta gctcttgatc    2760
cggcaaacaa accaccgctg gtagcggtgg ttttttttgtt tgcaagcagc agattacgcg    2820
cagaaaaaaa ggatctcaag aagatccttt gatcttttct acggggtctg acgctcagtg    2880
gaacgaaaac tcacgttaag ggattttggt catgagatta tcaaaaagga tcttcaccta    2940 gatccttttaa aattaaaaat gaagttttaa atcaatctaa agtatatatg agtaaacttg    3000
gtctgacagt taccaatgct taatcagtga ggcacctatc tcagcgatct gtctatttcg    3060
ttcatccata gttgcctgac tccccgtcgt gtagataact acgatacggg agggcttacc    3120
atctggcccc agtgctgcaa tgataccgcg agacccacgc tcaccggctc cagatttatc    3180
agcaataaac cagccagccg gaagggccga gcgcagaagt ggtcctgcaa ctttatccgc    3240
ctccatccag tctattaatt gttgccggga agctagagta agtagttcgc cagttaatag    3300
tttgcgcaac gttgttgcca ttgctacagg catcgtggtg tcacgctcgt cgtttggtat    3360
ggcttcattc agctccggtt cccaacgatc aaggcgagtt acatgatccc ccatgttgtg    3420
caaaaaagcg gttagctcct tcggtcctcc gatcgttgtc agaagtaagt tggccgcagt    3480
gttatcactc atggttatgg cagcactgca taattctctt actgtcatgc catccgtaag    3540
atgcttttct gtgactggtg agtactcaac caagtcattc tgagaatagt gtatgcggcg    3600
accgagttgc tcttgcccgg cgtcaatacg ggataatacc gcgccacata gcagaacttt    3660
aaaagtgctc atcattggaa aacgttcttc ggggcgaaaa ctctcaagga tcttaccgct    3720
gttgagatcc agttcgatgt aacccactcg tgcacccaac tgatcttcag catcttttac    3780
tttcaccagc gtttctgggt gagcaaaaac aggaaggcaa aatgccgcaa aaaagggaat    3840
aagggcgaca cggaaatgtt gaatactcat actcttcctt tttcaatatt attgaagcat    3900
ttatcagggt tattgtctca tgagcggata catatttgaa tgtatttaga aaaataaaca    3960
aataggggtt ccgcgcacat ttccccgaaa agtgccacct gacgtctaag aaaccattat    4020
tatcatgaca ttaacctata aaaataggcg tatcacgagg cccttttcgtc              4070
```

<210> SEQ ID NO 49
<211> LENGTH: 8438
<212> TYPE: DNA
<213> ORGANISM: Artificial Sequence
<220> FEATURE:
<223> OTHER INFORMATION: Plasmid pDMW369

<400> SEQUENCE: 49

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
```

```
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca gctctaaat cggggggctcc   2580 ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg cgatcggtg cgggcctctt cgctattacg   2940
ccagctggcg aaagggggat gtgctgcaag gcgattaagt tgggtaacgc cagggttttc   3000
```

-continued

```
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa atatattgt    3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tactttgaa gaagcaaaaa aaatgaaaga aaaaaaaat     4140
cgtatttcca ggttagacgt tccgcagaat ctagaatgcg gtatgcgta cattgttctt    4200
cgaacgtaaa agttgcgctc cctgagatat tgtacatttt tgcttttaca agtacaagta   4260
catcgtacaa ctatgtacta ctgttgatgc atccacaaca gtttgttttg ttttttttg    4320
ttttttttt ttctaatgat tcattaccgc tatgtatacc tacttgtact tgtagtaagc    4380
cgggttattg gcgttcaatt aatcatagac ttatgaatct gcacggtgtg cgctgcgagt   4440
tactttagc ttatgcatgc tacttgggtg taatattggg atctgttcgg aaatcaacgg    4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
```

```
tgcttgacag tgttgccaat atctgcgaac tttctgtcct cgaacaggaa gaaaccgtgc  5400
ttaagagcaa gttccttgag ggggagcaca gtgccggcgt aggtgaagtc gtcaatgatg  5460
tcgatatggg ttttgatcat gcacacataa ggtccgacct tatcggcaag ctcaatgagc  5520
tccttggtgg tggtaacatc cagagaagca cacaggttgg ttttcttggc tgccacgagc  5580
ttgagcactc gagcggcaaa ggcggacttg tggacgttag ctcgagcttc gtaggagggc  5640
attttggtgg tgaagaggag actgaaataa atttagtctg cagaactttt tatcggaacc  5700
ttatctgggg cagtgaagta tatgttatgg taatagttac gagttagttg aacttataga  5760
tagactggac tatacggcta tcggtccaaa ttagaaagaa cgtcaatggc tctctgggcg  5820 tcgccttgc cgacaaaaat gtgatcatga tgaaagccag caatgacgtt gcagctgata  5880
ttgttgtcgg ccaaccgcgc cgaaaacgca gctgtcagac ccacagcctc caacgaagaa  5940
tgtatcgtca aagtgatcca agcacactca tagttggagt cgtactccaa aggcggcaat  6000
gacgagtcag acagatactc gtcgactcag gcgacgacgg aattcctgca gcccatctgc  6060
agaattcagg agagaccggg ttggcggcgt atttgtgtcc caaaaaacag ccccaattgc  6120
cccggagaag acgccaggc cgcctagatg acaaattcaa caactcacag ctgactttct  6180
gccattgcca ctagggggg gccttttta atggccaagc caagctctcc acgtcggttg  6240
ggctgcaccc aacaataaat gggtagggtt gcaccaacaa agggatggga tgggggtag  6300 aagatacgag gataacgggg ctcaatggca caaataagaa cgaatactgc cattaagact  6360
cgtgatccag cgactgacac cattgcatca tctaagggcc tcaaaactac ctcggaactg  6420
ctgcgctgat ctggacacca cagaggttcc gagcacttta ggttgcacca aatgtcccac  6480
caggtgcagg cagaaaacgc tggaacagcg tgtacagttt gtcttaacaa aaagtgaggg  6540
cgctgaggtc gagcagggtg gtgtgacttg ttatagcctt tagagctgcg aaagcgcgta  6600
tggatttggc tcatcaggcc agattgaggg tctgtggaca catgtcatgt tagtgtactt  6660
caatcgcccc ctggatatag ccccgacaat aggccgtggc ctcatttttt tgccttccgc  6720
acatttccat tgctcggtac ccacaccttg cttctcctgc acttgccaac cttaatactg  6780
gtttacattg accaacatct tacaagcggg gggcttgtct agggtatata taaacagtgg  6840
ctctcccaat cggttgccag tctctttttt cctttctttc cccacagatt cgaaatctaa  6900
actacacatc acacaatgcc tgttactgac gtccttaagc gaaagtccgg tgtcatcgtc  6960
ggcgacgatg tccgagccgt gagtatccac gacaagatca gtgtcgagac gacgcgtttt  7020
gtgtaatgac acaatccgaa agtcgctagc aacacacact ctctacacaa actaacccag  7080
ctctccatgg ctctctccct tactaccgag cagctgctcg agcgacccga cctggttgcc  7140
atcgacggca ttctctacga tctggaaggt cttgccaagg tccatcccgg aggcgacttg  7200
atcctcgctt ctggtgcctc cgatgcttct cctctgttct actccatgca cccttacgtc  7260
aagcccgaga actcgaagct gcttcaacag ttcgtgcgag gcaagcacga ccgaacctcc  7320
aaggacattg tctacaccta cgactctccc tttgcacagg acgtcaagcg aactatgcga  7380
gaggtcatga aaggtcggaa ctggtatgcc acacctggat tctggctgcg aaccgttggc  7440
atcattgctg tcaccgcctt ttgcgagtgg cactgggcta ctaccggaat ggtgctgtgg  7500
ggtctcttga ctggattcat gcacatgcag atcggcctgt ccattcagca cgatgcctct  7560
catggtgcca tcagcaaaaa gccctgggtc aacgctctct ttgcctacgg catcgacgtc  7620
attggatcgt ccagatggat ctggctgcag tctcacatca tgcgacatca cacctacacc  7680
aatcagcatg gtctcgacct ggatgccgag tccgcagaac cattccttgt gttccacaac  7740
```

-continued

```
taccctgctg ccaacactgc tcgaaagtgg tttcaccgat tccaggcctg gtacatgtac    7800
ctcgtgcttg gagcctacgg cgtttcgctg gtgtacaacc ctctctacat cttccgaatg    7860
cagcacaacg acaccattcc cgagtctgtc acagccatgc gagagaacgg ctttctgcga    7920
cggtaccgaa cccttgcatt cgttatgcga gctttcttca tctttcgaac cgccttcttg    7980
ccctggtatc tcactggaac ctccctgctc atcaccattc ctctggtgcc cactgctacc    8040
ggtgccttcc tcaccttctt tttcatcttg tctcacaact tcgatggctc ggagcgaatc    8100
cccgacaaga actgcaaggt caagagctcc gagaaggacg ttgaagccga tcagatcgac    8160
tggtacagag ctcaggtgga gacctcttcc acctacggtg gacccattgc catgttcttt    8220
actggcggtc tcaacttcca gatcgagcat cacctctttc ctcgaatgtc gtcttggcac    8280
tatcccttcg tgcagcaagc tgtccgagag tgttgcgaac gacacggagt tcggtacgtc    8340
ttctacccta ccattgtggg caacatcatt tccaccctca agtacatgca caaagtcggt    8400
gtggttcact gtgtcaagga cgctcaggat tcctaagc                            8438
```

<210> SEQ ID NO 50
<211> LENGTH: 19
<212> TYPE: DNA
<213> ORGANISM: Artificial Sequence
<220> FEATURE:
<223> OTHER INFORMATION: Primer T7

<400> SEQUENCE: 50
ggaaacagct atgaccatg                                                    19

<210> SEQ ID NO 51
<211> LENGTH: 459
<212> TYPE: PRT
<213> ORGANISM: Rhizopus stolonifer (GenBank Accession No. AAX22052)

<400> SEQUENCE: 51

```
Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Leu Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
```

-continued

```
               180              185              190
Val Phe Leu Gly Asn Phe Cys Gln Gly Phe Ser Leu Ser Trp Trp Lys
        195              200              205
Asn Lys His Asn Thr His His Ala Ser Thr Asn Val His Gly Gln Asp
        210              215              220
Pro Asp Ile Asp Thr Ala Pro Val Leu Leu Trp Asp Glu Tyr Ala Ser
225              230              235              240
Ala Ala Tyr Tyr Ala Ser Leu Asp Gln Glu Pro Thr Met Val Ser Arg
                245              250              255
Phe Leu Ala Glu Gln Val Leu Pro His Gln Thr Arg Tyr Phe Phe Phe
            260              265              270
Ile Leu Ala Phe Ala Arg Leu Ser Trp Ala Leu Gln Ser Leu Ser Tyr
        275              280              285
Ser Phe Lys Lys Glu Ser Ile Asn Lys Ser Arg Gln Leu Asn Leu Phe
        290              295              300
Glu Arg Val Cys Ile Val Gly His Trp Ala Leu Phe Ala Phe Cys Ile
305              310              315              320
Tyr Ser Trp Cys Ser Asn Val Tyr His Met Val Leu Phe Phe Leu Val
                325              330              335
Ser Gln Ala Thr Thr Gly Tyr Thr Leu Ala Leu Val Phe Ala Leu Asn
            340              345              350
His Asn Gly Met Pro Val Ile Thr Glu Glu Lys Ala Glu Ser Met Glu
        355              360              365
Phe Phe Glu Ile Gln Val Ile Thr Gly Arg Asp Val Thr Leu Ser Pro
        370              375              380
Leu Gly Asp Trp Phe Met Gly Gly Leu Asn Tyr Gln Ile Glu His His
385              390              395              400
Val Phe Pro Asn Met Pro Arg His Asn Leu Pro Thr Val Lys Pro Met
                405              410              415
Val Lys Ser Leu Cys Gln Lys Tyr Asp Ile Asn Tyr His Asp Thr Gly
            420              425              430
Phe Leu Lys Gly Thr Leu Glu Val Leu Gln Thr Leu Asp Ile Thr Ser
        435              440              445
Lys Leu Ser Leu Gln Leu Ser Lys Lys Ser Phe
        450              455

<210> SEQ ID NO 52
<211> LENGTH: 695
<212> TYPE: DNA
<213> ORGANISM: Pavlova lutheri

<400> SEQUENCE: 52
agggccaagg gtgccaacca ccttccacgt gagactacac accgtaggcc gatgggcaag     60
ggtggagacg gcggcgcgca ggcggtgagc gggaccgacg cgtctctcgc tgaggtgagc    120
tccgtcgata gcaagagcgt gcacgtcgtg ctctacggca agcgcgtgga tgtcacaaag    180
ttccagggct acgacgtggc ctggtggcgc gcgcgccata acacgcacca cgtgtgcacc    240
aacgaggatg gttcggaccc ggacatcaag acggcgcccc tgctcatcta cgtgcgagag    300
aacccgtcca ttgccaagcg gctcaacttc ttccagcgct ggcagcagta ctactatgtg    360
ccgaccatgg ccatcctcga cctctactgg cgcctggagt ccatcgcgta cgtggctgtg    420
cgcctgccta agatgtggat gcaggccgcc gctcttgccg ctcactacgc gctcctgtgc    480
tgggtcttcg cagcgcatct caacctcatc cctctcatga tggttgcacg cggcttcgcg    540
```

```
acgggcatcg ttgtctttgc aacccactat ggtgaggaca tcctcgaccg cgagcacgtc    600
gagggcatga cgctcgtcga gcagaccgcc aagacctccc gtaacatcac gggcggctgg    660
ctagtgaacg tgctcacggg cttcatctcc ctgca                               695
```

<210> SEQ ID NO 53
<211> LENGTH: 1106
<212> TYPE: DNA
<213> ORGANISM: Pavlova lutheri

<400> SEQUENCE: 53

```
agggccaagg gtgccaacca ccttccacgt gagactacac accgtaggcc gatgggcaag     60
ggtggagacg gcggcgcgca ggcggtgagc gggaccgacg cgtctctcgc tgaggtgagc    120
tccgtcgata gcaagagcgt gcacgtcgtg ctctacggca agcgcgtgga tgtcacaaag    180
ttccagggct acgacgtggc ctggtggcgc gcgcgccata acacgcacca cgtgtgcacc    240
aacgaggatg gttcggaccc ggacatcaag acggcgcccc tgctcatcta cgtgcgagag    300
aacccgtcca ttgccaagcg gctcaacttc ttccagcgct ggcagcagta ctactatgtg    360
ccgaccatgg ccatcctcga cctctactgg cgcctggagt ccatcgcgta cgtggctgtg    420
cgcctgccta agatgtggat gcaggccgcc gctcttgccg ctcactacgc gctcctgtgc    480
tgggtcttcg cagcgcatct caacctcatc cctctcatga tggttgcacg cggcttcgcg    540
acgggcatcg ttgtctttgc aacccactat ggtgaggaca tcctcgaccg cgagcacgtc    600
gagggcatga cgctcgtcga gcagaccgcc aagacctccc gtaacatcac gggcggctgg    660
ctagtgaacg tgctcacggg cttcatctcc ctgcagaccg agcatcacct cttccccatg    720
atgcccaccg caacctaat gactatccag cccgaggtac gcgacttctt caagaagcat    780
ggcctcgagt accgcgaggg caacctcttc cagtgcgtgc accagaacat caaggctctc    840
gccttcgagc acctcctcca ctgagcgtca ccactcaagc gtcctaagtg cacaggtact    900
gtcttctgac cgatggccgc gcggctccct cggctggcag tggggccaac gagtggcctc    960
gcgggatcgg gcacgatcgg gcctccatga aacttcagtg ttcagagaca agccgacaac   1020
ctccgcatcg tgagaaatct tttaaagcag tatgttccat cacgccgctt ttgcagtcaa   1080
taacattacc caaaaaaaaa aaaaaa                                        1106
```

<210> SEQ ID NO 54
<211> LENGTH: 287
<212> TYPE: PRT
<213> ORGANISM: Pavlova lutheri

<400> SEQUENCE: 54

```
Arg Ala Lys Gly Ala Asn His Leu Pro Arg Glu Thr Thr His Arg Arg
1               5                   10                  15

Pro Met Gly Lys Gly Gly Asp Gly Ala Gln Ala Val Ser Gly Thr
            20                  25                  30

Asp Ala Ser Leu Ala Glu Val Ser Val Asp Ser Lys Ser Val His
        35                  40                  45

Val Val Leu Tyr Gly Lys Arg Val Asp Val Thr Lys Phe Gln Gly Tyr
    50                  55                  60

Asp Val Ala Trp Trp Arg Ala Arg His Asn Thr His His Val Cys Thr
65                  70                  75                  80

Asn Glu Asp Gly Ser Asp Pro Asp Ile Lys Thr Ala Pro Leu Leu Ile
                85                  90                  95

Tyr Val Arg Glu Asn Pro Ser Ile Ala Lys Arg Leu Asn Phe Phe Gln
```

```
              100                 105                 110
Arg Trp Gln Gln Tyr Tyr Tyr Val Pro Thr Met Ala Ile Leu Asp Leu
        115                 120                 125

Tyr Trp Arg Leu Glu Ser Ile Ala Tyr Val Ala Val Arg Leu Pro Lys
130                 135                 140

Met Trp Met Gln Ala Ala Ala Leu Ala Ala His Tyr Ala Leu Leu Cys
145                 150                 155                 160

Trp Val Phe Ala Ala His Leu Asn Leu Ile Pro Leu Met Met Val Ala
                165                 170                 175

Arg Gly Phe Ala Thr Gly Ile Val Val Phe Ala Thr His Tyr Gly Glu
            180                 185                 190

Asp Ile Leu Asp Arg Glu His Val Glu Gly Met Thr Leu Val Glu Gln
                195                 200                 205

Thr Ala Lys Thr Ser Arg Asn Ile Thr Gly Gly Trp Leu Val Asn Val
210                 215                 220

Leu Thr Gly Phe Ile Ser Leu Gln Thr Glu His Leu Phe Pro Met
225                 230                 235                 240

Met Pro Thr Gly Asn Leu Met Thr Ile Gln Pro Glu Val Arg Asp Phe
                245                 250                 255

Phe Lys Lys His Gly Leu Glu Tyr Arg Glu Gly Asn Leu Phe Gln Cys
                260                 265                 270

Val His Gln Asn Ile Lys Ala Leu Ala Phe Glu His Leu Leu His
                275                 280                 285

<210> SEQ ID NO 55
<211> LENGTH: 20
<212> TYPE: DNA
<213> ORGANISM: Artificial Sequence
<220> FEATURE:
<223> OTHER INFORMATION: Primer SeqE

<400> SEQUENCE: 55
cgacacactc caatctttcc                                              20

<210> SEQ ID NO 56
<211> LENGTH: 20
<212> TYPE: DNA
<213> ORGANISM: Artificial Sequence
<220> FEATURE:
<223> OTHER INFORMATION: Primer SeqW

<400> SEQUENCE: 56
ggtggctgga gttagacatc                                              20

<210> SEQ ID NO 57
<211> LENGTH: 22
<212> TYPE: DNA
<213> ORGANISM: Artificial Sequence
<220> FEATURE:
<223> OTHER INFORMATION: Primer AP1

<400> SEQUENCE: 57
gtaatacgac tcactatagg gc                                           22

<210> SEQ ID NO 58
<211> LENGTH: 20
<212> TYPE: DNA
<213> ORGANISM: Artificial Sequence
<220> FEATURE:
<223> OTHER INFORMATION: Primer GSP PvDES
```

<400> SEQUENCE: 58
ctgcgaagac ccagcacagg						20

<210> SEQ ID NO 59
<211> LENGTH: 22
<212> TYPE: DNA
<213> ORGANISM: Artificial Sequence
<220> FEATURE:
<223> OTHER INFORMATION: Primer M13-28Rev

<400> SEQUENCE: 59
gtaatacgac tcactatagg gc					22

<210> SEQ ID NO 60
<211> LENGTH: 21
<212> TYPE: DNA
<213> ORGANISM: Artificial Sequence
<220> FEATURE:
<223> OTHER INFORMATION: Primer PavDes seq

<400> SEQUENCE: 60
ttgtggcgct caatcatctc c						21

<210> SEQ ID NO 61
<211> LENGTH: 1294
<212> TYPE: DNA
<213> ORGANISM: Pavlova lutheri

<400> SEQUENCE: 61
ctttgcgagc gcggcgcaga cgattgcggc ccgtagtgat cgcggtgcgc attgctgtgt			60
ttctagtttt gctgacgccc ggcccgataa tgacaccttc tcccgtttga aatactaata			120
agtaactata ttataatatt caaaggtggc gactatggat ctccttttct aaagttcagc			180
ggaattggga atcggagaaa tttcgagata tgtcataatc acgtgctcta tctcgaatga			240
accgcggccg gtgagcgatt actcgggaag ccaattccta ttaacgagtc agggggatc			300
tttgaggtga tcggccacg cagagagagc aaggaatcat cctcatccgc cgttctcgag			360
aaagagccaa gggtgccaac caccttccac gtgagactac acaccgtagg ccgatgggca			420
agggtggaga cggcgcgcg caggcggcga gcgggaccga cgcatctctc gctgaggtga			480
gctccgtcga tagcaagagc gtgcgcgtcg tgctctacgg caagcgcgtg gatgtcacaa			540
agttccagag ggcacacccg ggcgggagca aggtgttccg catcttccag gagcgcgacg			600
cgacggagca gttcgagtct taccactcgc ccaaggccat caagatgatg gagggcatgc			660
tcaagaagtc ggaggatgcg cccgcttccg tgccctgcc ctcgcggtcc accatgggca			720
cggagttcaa ggagatgatt gagcgccaca agagggctgg tctctacgac ccttgcccgt			780
tggacgagct gttcaagctc accatcgtcc ttgcgcccat cttcgtgggc gcctatctcg			840
tgcggagcgg cgtctcgccc ctcgcgggcg cgctctccat gggctttggc ttctacctcg			900
acggctggct tgctcacrac tacctgcatc acgcagtctt caagggctcg gtcaacacgc			960
tcgtcaaggc gaacaacgcc atgggatacg ccctcggctt cctccagggc tacgacgtgg			1020
cctggtggcg cgcgcgccat aacacgcacc acgtgtgcac caacgaggat ggttcggacc			1080
cggacatcaa gacggcgccc ctgctcatct acgtgcgaga gaacccgtcc attgccaagc			1140
ggctcaactt cttccagcgc tggcagcagt actactatgt gccgaccatg gccatcctcg			1200
acctctactg gcgcctggag tccatcgcgt acgtggctgt gcgcctgcct aagatgtgga			1260
tgcaggccgc cgctcttgcc gctcactacg cgct					1294

<210> SEQ ID NO 62
<211> LENGTH: 1927
<212> TYPE: DNA
<213> ORGANISM: Pavlova lutheri

<400> SEQUENCE: 62

```
ctttgcgagc gcggcgcaga cgattgcggc ccgtagtgat cgcggtgcgc attgctgtgt      60
ttctagtttt gctgacgccc ggcccgataa tgacaccttc tcccgtttga atactaata     120
agtaactata ttataatatt caaaggtggc gactatggat ctccttttct aaagttcagc     180
ggaattggga atcggagaaa tttcgagata tgtcataatc acgtgctcta tctcgaatga     240
accgcggccg gtgagcgatt actcgggaag ccaattccta ttaacgagtc aggggggatc     300
tttgaggtga gtcggccacg cagagagagc aaggaatcat cctcatccgc cgttctcgag     360
aaagagccaa gggtgccaac caccttccac gtgagactac acccgtagg ccgatgggca      420
agggtggaga cggcggcgcg caggcggtga gcggaccga cgcgtctctc gctgaggtga      480
gctccgtcga tagcaagagc gtgcacgtcg tgctctacgg caagcgcgtg gatgtcacaa     540
agttccagaa ggcacacccg gcgggagca aggtgttccg catcttccag gagcgcgacg      600
cgacggagca gttcgagtct taccactcgc ccaaggccat caagatgatg gagggcatgc     660
tcaagaagtc ggaggatgcg cccgcttccg tgccctgcc ctcgcggtcc accatgggca      720
cggagttcaa ggagatgatt gagcgccaca gagggctgg tctctacgac ccttgcccgt      780
tggacgagct gttcaagctc accatcgtcc ttgcgcccat cttcgtgggc gcctatctcg     840
tgcggagcgg cgtctcgccc ctcgcgggcg cgctctccat gggctttggc ttctacctcg     900
acggctggct tgctcacgac tacctgcatc acgcagtctt caagggctcg gtcaacacgc     960
tcgtcaaggc gaacaacgcc atgggatacg ccctcggctt cctccagggc tacgacgtgg    1020
cctggtggcg cgcgcgccat aacacgcacc acgtgtgcac caacgaggat ggttcggacc    1080
cggacatcaa cacggcgccc ctgctcatct acgtgcgaga gaacccgtcc attgccaagc    1140
ggctcaactt cttccagcgc tggcagcagt actactatgt gccgaccatg ccatcctcg     1200
acctctactg gcgcctggag tccatcgcgt acgtggctgt gcgcctgcct aagatgtgga    1260
tgcaggccgc cgctcttgcc gctcactacg cgctcctgtg ctgggtcttc gcagcgcatc    1320
tcaacctcat ccctctcatg atggttgcac gcggcttcgc gacgggcatc gttgtctttg    1380
caacccacta tggtgaggac atcctcgacc gcgagcacgt cgagggcatg acgctcgtcg    1440
agcagaccgc caagacctcc cgtaacatca cgggcggctg gctagtgaac gtgctcacgg    1500
gcttcatctc cctgcagacc gagcatcacc tcttccccat gatgcccacc ggcaacctaa    1560
tgactatcca gcccgaggta cgcgacttct tcaagaagca tggcctcgag taccgcgagg    1620
gcaacctctt ccagtgcgtg caccagaaca tcaaggctct cgccttcgag cacctcctcc    1680
actgagcgtc accactcaag cgtcctaagt gcacaggtac tgtcttctga ccgatggccg    1740
cgcggctccc tcggctggca gtggggccaa cgagtggcct cgcgggatcg ggcacgatcg    1800
ggcctccatg aaacttcagt gttcagagac aagccgacaa cctccgcatc gtgagaaatc    1860
ttttaaagca gtatgttcca tcacgccgct tttgcagtca ataacattac ccaaaaaaaa    1920
aaaaaaa                                                               1927
```

<210> SEQ ID NO 63
<211> LENGTH: 459
<212> TYPE: PRT

<213> ORGANISM: Rhizopus stolonifer (GenBank Accession No. ABB96724)

<400> SEQUENCE: 63

```
Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Ala Met Lys Phe
            20                  25                  30

Ile Ile Ile Asp Lys Lys Val Tyr Asp Val Thr Glu Phe Ile Glu Asp
                35                  40                  45

His Pro Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
            115                 120                 125

Lys Val Leu Ser Thr Leu Ala Ile Cys Ile Ala Gly Leu Ser Pro Leu
130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
            195                 200                 205

Asn Lys His Asn Thr His His Ala Ser Thr Asn Val His Gly Gln Asp
210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe
            260                 265                 270

Ile Leu Ala Phe Ala Arg Leu Ser Trp Ala Leu Gln Ser Leu Ser Tyr
            275                 280                 285

Ser Phe Lys Lys Glu Ser Ile Asn Lys Ser Arg Gln Leu Asn Leu Phe
290                 295                 300

Glu Arg Val Cys Ile Val Gly His Trp Ala Leu Ser Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
            355                 360                 365

Phe Phe Glu Ile Gln Val Ile Thr Gly Arg Asp Val Thr Leu Ser Pro
370                 375                 380

Leu Gly Asp Trp Phe Met Gly Gly Leu Asn Tyr Gln Ile Glu His His
385                 390                 395                 400
```

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
    450                 455

<210> SEQ ID NO 64
<211> LENGTH: 427
<212> TYPE: PRT
<213> ORGANISM: Pavlova salina
<300> PUBLICATION INFORMATION:
<302> TITLE: SYNTHESIS OF LONG-CHAIN POLYUNSATURATED FATTY ACIDS BY
      RECOMBINANT CELLS
<310> PATENT DOCUMENT NUMBER: WO 2005/103253
<311> PATENT FILING DATE: 2005-04-22
<312> PUBLICATION DATE: 2005-11-03
<313> RELEVANT RESIDUES: (1)..(427)

<400> SEQUENCE: 64

Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
    210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro

```
                275                 280                 285
Gln Ala Leu Ala Leu Val Ala His Tyr Ala Ile Val Ala Trp Val Phe
            290                 295                 300
Ala Gly Asn Tyr His Leu Leu Pro Leu Val Thr Val Leu Arg Gly Phe
305                 310                 315                 320
Gly Thr Gly Ile Thr Val Phe Ala Thr His Tyr Gly Glu Asp Ile Leu
                325                 330                 335
Asp Ala Asp Gln Val Arg His Met Thr Leu Val Glu Gln Thr Ala Leu
            340                 345                 350
Thr Ser Arg Asn Ile Ser Gly Gly Trp Leu Val Asn Val Leu Thr Gly
        355                 360                 365
Phe Ile Ser Leu Gln Thr Glu His His Leu Phe Pro Met Met Pro Thr
370                 375                 380
Gly Asn Leu Met Thr Ile Gln Pro Glu Val Arg Ala Phe Phe Lys Lys
385                 390                 395                 400
His Gly Leu Glu Tyr Arg Glu Gly Asn Leu Ile Glu Cys Val Arg Gln
                405                 410                 415
Asn Ile Arg Ala Leu Ala Phe Glu His Leu Leu
            420                 425
```

<210> SEQ ID NO 65
<211> LENGTH: 37
<212> TYPE: DNA
<213> ORGANISM: Artificial Sequence
<220> FEATURE:
<223> OTHER INFORMATION: Primer AP

<400> SEQUENCE: 65
ggccacgcgt cgactagtac ttttttttt tttttt                        37

<210> SEQ ID NO 66
<211> LENGTH: 39
<212> TYPE: DNA
<213> ORGANISM: Artificial Sequence
<220> FEATURE:
<223> OTHER INFORMATION: Smart IV oligonucleotide primer

<400> SEQUENCE: 66
aagcagtggt atcaacgcag agtggccatt acggccggg                    39

<210> SEQ ID NO 67
<211> LENGTH: 1338
<212> TYPE: DNA
<213> ORGANISM: Mortierella alpina

<400> SEQUENCE: 67
atgggaacgg accaaggaaa accttcacc tgggaagagc tggcggccca taacaccaag      60
gacgacctac tcttggccat ccgcggcagg gtgtacgatg tcacaaagtt cttgagccgc    120
catcctggtg gagtggacac tctcctgctc ggagctggcc gagatgttac tccggtcttt    180
gagatgtatc acgcgtttgg ggctgcagat gccattatga agaagtacta tgtcggtaca    240
ctggtctcga atgagctgcc catcttccg gagccaacgg tgttccacaa aaccatcaag    300
acgagagtcg agggctactt tacgatcgg aacattgatc ccaagaatag accagagatc    360
tggggacgat acgctcttat ctttggatcc ttgatcgctt cctactacgc gcagctcttt    420
gtgcctttcg ttgtcgaacg cacatggctt caggtggtgt ttgcaatcat catgggattt    480
gcgtgcgcac aagtcggact caaccctctt catgatgcgt ctcactttc agtgacccac    540

-continued

```
aacccccactg tctggaagat tctgggagcc acgcacgact ttttcaacgg agcatcgtac      600
ctggtgtgga tgtaccaaca tatgctcggc catcacccct acaccaacat tgctggagca      660
gatcccgacg tgtcgacgtc tgagcccgat gttcgtcgta tcaagcccaa ccaaaagtgg      720
tttgtcaacc acatcaacca gcacatgttt gttccttttcc tgtacggact gctggcgttc    780
aaggtgcgca ttcaggacat caacattttg tactttgtca agaccaatga cgctattcgt     840
gtcaatccca tctcgacatg gcacactgtg atgttctggg gcggcaaggc tttctttgtc     900
tggtatcgcc tgattgttcc cctgcagtat ctgcccctgg gcaaggtgct gctcttgttc    960
acggtcgcgg acatggtgtc gtcttactgg ctggcgctga ccttccaggc gaaccacgtt   1020
gttgaggaag ttcagtggcc gttgcctgac gagaacggga tcatccaaaa ggactgggca   1080
gctatgcagg tcgagactac gcaggattac gcacacgatt cgcacctctg gaccagcatc   1140
actggcagct tgaactacca ggctgtgcac catctgttcc ccaacgtgtc gcagcaccat   1200
tatcccgata ttctggccat catcaagaac acctgcagcg agtacaaggt tccatacctt   1260
gtcaaggata cgttttggca agcatttgct tcacatttgg agcacttgcg tgttcttgga   1320
ctccgtccca aggaagag                                                  1338
```

<210> SEQ ID NO 68
<211> LENGTH: 446
<212> TYPE: PRT
<213> ORGANISM: Mortierella alpina

<400> SEQUENCE: 68

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
```

```
            225                 230                 235                 240
Phe Val Asn His Ile Asn Gln His Met Phe Val Pro Phe Leu Tyr Gly
                245                 250                 255
Leu Leu Ala Phe Lys Val Arg Ile Gln Asp Ile Asn Ile Leu Tyr Phe
            260                 265                 270
Val Lys Thr Asn Asp Ala Ile Arg Val Asn Pro Ile Ser Thr Trp His
        275                 280                 285
Thr Val Met Phe Trp Gly Gly Lys Ala Phe Phe Val Trp Tyr Arg Leu
    290                 295                 300
Ile Val Pro Leu Gln Tyr Leu Pro Leu Gly Lys Val Leu Leu Leu Phe
305                 310                 315                 320
Thr Val Ala Asp Met Val Ser Ser Tyr Trp Leu Ala Leu Thr Phe Gln
                325                 330                 335
Ala Asn His Val Val Glu Val Gln Trp Pro Leu Pro Asp Glu Asn
            340                 345                 350
Gly Ile Ile Gln Lys Asp Trp Ala Ala Met Gln Val Glu Thr Thr Gln
        355                 360                 365
Asp Tyr Ala His Asp Ser His Leu Trp Thr Ser Ile Thr Gly Ser Leu
    370                 375                 380
Asn Tyr Gln Ala Val His His Leu Phe Pro Asn Val Ser Gln His His
385                 390                 395                 400
Tyr Pro Asp Ile Leu Ala Ile Ile Lys Asn Thr Cys Ser Glu Tyr Lys
                405                 410                 415
Val Pro Tyr Leu Val Lys Asp Thr Phe Trp Gln Ala Phe Ala Ser His
            420                 425                 430
Leu Glu His Leu Arg Val Leu Gly Leu Arg Pro Lys Glu Glu
        435                 440                 445

<210> SEQ ID NO 69
<211> LENGTH: 6473
<212> TYPE: DNA
<213> ORGANISM: Artificial Sequence
<220> FEATURE:
<223> OTHER INFORMATION: Plasmid pY5-22

<400> SEQUENCE: 69
ggtggagctc cagcttttgt tccctttagt gagggttaat ttcgagcttg gcgtaatcat    60
ggtcatagct gtttcctgtg tgaaattgtt atccgctcac aattccacac aacgtacgag   120
ccggaagcat aaagtgtaaa gcctggggtg cctaatgagt gagctaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
```

-continued

```
cgaggtatgt aggcggtgct acagagttct tgaagtggtg gcctaactac ggctacacta      900
gaaggacagt atttggtatc tgcgctctgc tgaagccagt taccttcgga aaaagagttg      960
gtagctcttg atccggcaaa caaaccaccg ctggtagcgg tggttttttt gtttgcaagc     1020
agcagattac gcgcagaaaa aaaggatctc aagaagatcc tttgatcttt tctacggggt     1080
ctgacgctca gtggaacgaa aactcacgtt aagggatttt ggtcatgaga ttatcaaaaa     1140
ggatcttcac ctagatcctt ttaaattaaa aatgaagttt taaatcaatc taaagtatat     1200
atgagtaaac ttggtctgac agttaccaat gcttaatcag tgaggcacct atctcagcga     1260
tctgtctatt tcgttcatcc atagttgcct gactccccgt cgtgtagata actacgatac     1320
gggagggctt accatctggc cccagtgctg caatgatacc gcgagaccca cgctcaccgg     1380
ctccagattt atcagcaata aaccagccag ccggaagggc cgagcgcaga agtggtcctg     1440
caactttatc cgcctccatc cagtctatta attgttgccg ggaagctaga gtaagtagtt     1500
cgccagttaa tagtttgcgc aacgttgttg ccattgctac aggcatcgtg gtgtcacgct     1560
cgtcgtttgg tatggcttca ttcagctccg gttcccaacg atcaaggcga gttacatgat     1620
cccccatgtt gtgcaaaaaa gcggttagct ccttcggtcc tccgatcgtt gtcagaagta     1680
agttggccgc agtgttatca ctcatggtta tggcagcact gcataattct cttactgtca     1740
tgccatccgt aagatgcttt tctgtgactg gtgagtactc aaccaagtca ttctgagaat     1800
agtgtatgcg gcgaccgagt tgctcttgcc cggcgtcaat acgggataat accgcgccac     1860
atagcagaac tttaaaagtg ctcatcattg gaaaacgttc ttcggggcga aaactctcaa     1920
ggatcttacc gctgttgaga tccagttcga tgtaacccac tcgtgcaccc aactgatctt     1980
cagcatcttt tactttcacc agcgtttctg ggtgagcaaa aacaggaagg caaaatgccg     2040
caaaaaaggg aataagggcg acacggaaat gttgaatact catactcttc cttttcaat     2100
attattgaag catttatcag ggttattgtc tcatgagcgg atacatattt gaatgtattt     2160
agaaaaataa acaaataggg gttccgcgca catttccccg aaaagtgcca cctgacgcgc     2220
cctgtagcgg cgcattaagc gcggcgggtg tggtggttac gcgcagcgtg accgctacac     2280
ttgccagcgc cctagcgccc gctcctttcg ctttcttccc ttcctttctc gccacgttcg     2340
ccggctttcc ccgtcaagct ctaaatcggg ggctcccttt agggttccga tttagtgctt     2400
tacggcacct cgaccccaaa aaacttgatt agggtgatgg ttcacgtagt gggccatcgc     2460
cctgatagac ggtttttcgc cctttgacgt tggagtccac gttctttaat agtggactct     2520
tgttccaaac tggaacaaca ctcaacccta tctcggtcta ttcttttgat ttataaggga     2580
ttttgccgat ttcggcctat tggttaaaaa atgagctgat ttaacaaaaa tttaacgcga     2640
attttaacaa aatattaacg cttacaattt ccattcgcca ttcaggctgc gcaactgttg     2700
ggaagggcga tcggtgcggg cctcttcgct attacgccag ctggcgaaag gggatgtgc     2760
tgcaaggcga ttaagttggg taacgccagg gttttcccag tcacgacgtt gtaaaacgac     2820
ggccagtgaa ttgtaatacg actcactata gggcgaattg gtaccgggc cccccctcga     2880
ggtcgatggt gtcgataagc ttgatatcga attcatgtca cacaaaccga tcttcgcctc     2940
aaggaaacct aattctacat ccgagagact gccgagatcc agtctacact gattaatttt     3000
cgggccaata atttaaaaaa atcgtgttat ataatattat atgtattata tatatacatc     3060
atgatgatac tgacagtcat gtcccattgc taaatagaca gactccatct gccgcctcca     3120
actgatgttc tcaatattta agggtcatc tcgcattgtt taataataaa cagactccat     3180
ctaccgcctc caaatgatgt tctcaaaata tattgtatga acttattttt attacttagt     3240
```

```
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtattttga tttaattttt    3840
tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta cattttgct tttacaagta caagtacatc gtacaactat gtactactgt    4080
tgatgcatcc acaacagttt gttttgtttt ttttgtttt ttttttttct aatgattcat    4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
ttaattaagt catacacaag tcagctttct tcgagcctca tataagtata agtagttcaa    4380
cgtattagca ctgtacccag catctccgta tcgagaaaca caacaacatg ccccattgga    4440
cagatcatgc ggatacacag gttgtgcagt atcatacata ctcgatcaga caggtcgtct    4500
gaccatcata caagctgaac aagcgctcca tacttgcacg ctctctatat acacagttaa    4560
attacatatc catagtctaa cctctaacag ttaatcttct ggtaagcctc ccagccagcc    4620
ttctggtatc gcttggcctc tcaatagga tctcggttct ggccgtacag acctcggccg    4680
acaattatga tatccgttcc ggtagacatg acatcctcaa cagttcggta ctgctgtccg    4740
agagcgtctc ccttgtcgtc aagacccacc ccggggtca gaataagcca gtcctcagag    4800
tcgcccttag gtcggttctg ggcaatgaag ccaaccacaa actcggggtc ggatcgggca    4860
agctcaatgg tctgcttgga gtactcgcca gtggccagag agcccttgca agacagctcg    4920
gccagcatga gcagacctct ggccagcttc tcgttgggag aggggactag gaactccttg    4980
tactgggagt tctcgtagtc agagacgtcc tccttcttct gttcagagac agtttcctcg    5040
gcaccagctc gcaggccagc aatgattccg gttccgggta caccgtgggc gttggtgata    5100
tcggaccact cggcgattcg gtgacaccgg tactggtgct tgacagtgtt gccaatatct    5160
gcgaactttc tgtcctcgaa caggaagaaa ccgtgcttaa gagcaagttc cttgagggg    5220 agcacagtgc cggcgtaggt gaagtcgtca atgatgtcga tatgggtttt gatcatgcac    5280
acataaggtc cgaccttatc ggcaagctca atgagctcct tggtggtggt aacatccaga    5340
gaagcacaca ggttggtttt cttggctgcc acgagcttga gcactcgagc ggcaaaggcg    5400
gacttgtgga cgttagctcg agcttcgtag gagggcattt tggtggtgaa gaggagactg    5460
aaataaattt agtctgcaga acttttatc ggaaccttat ctgggcagt gaagtatatg    5520 ttatggtaat agttacgagt tagttgaact tatagataga ctggactata cggctatcgg    5580
```

-continued

```
tccaaattag aaagaacgtc aatggctctc tgggcgtcgc ctttgccgac aaaaatgtga      5640
tcatgatgaa agccagcaat gacgttgcag ctgatattgt tgtcggccaa ccgcgccgaa      5700
aacgcagctg tcagacccac agcctccaac gaagaatgta tcgtcaaagt gatccaagca      5760
cactcatagt tggagtcgta ctccaaaggc ggcaatgacg agtcagacag atactcgtcg      5820
actcaggcga cgacggaatt cctgcagccc atctgcagaa ttcaggagag accgggttgg      5880
cggcgtattt gtgtcccaaa aaacagcccc aattgcccca attgaccccca aattgaccca      5940 gtagcgggcc caaccccggc gagagccccc ttcaccccac atatcaaacc tccccggtt       6000 cccacacttg ccgttaaggg cgtagggtac tgcagtctgg aatctacgct tgttcagact      6060
ttgtactagt ttctttgtct ggccatccgg gtaacccatg ccggacgcaa aatagactac      6120
tgaaaatttt tttgctttgt ggttgggact ttagccaagg gtataaaaga ccaccgtccc      6180
cgaattacct ttcctcttct tttctctctc tccttgtcaa ctcacacccg aaatcgttaa      6240
gcatttcctt ctgagtataa gaatcattca ccatggatcc actagttcta gagcggccgc      6300
caccgcggcc cgagattccg gcctcttcgg ccgccaagcg acccgggtgg acgtctagag      6360
gtacctagca attaacagat agtttgccgg tgataattct cttaacctcc cacactcctt      6420
tgacataacg atttatgtaa cgaaactgaa atttgaccag atattgtgtc cgc            6473
```

<210> SEQ ID NO 70
<211> LENGTH: 6970
<212> TYPE: DNA
<213> ORGANISM: Artificial Sequence
<220> FEATURE:
<223> OTHER INFORMATION: Plasmid pY5-22GPD

<400> SEQUENCE: 70

```
tcgacgcagt aggatgtcct gcacgggtct ttttgtgggg tgtggagaaa ggggtgcttg        60
gagatggaag ccggtagaac cgggctgctt gtgcttggag atggaagccg gtagaaccgg       120
gctgcttggg gggatttggg gccgctgggc tccaaagagg ggtaggcatt tcgttggggt       180
tacgtaattg cggcatttgg gtcctgcgcg catgtcccat tggtcagaat tagtccggat       240
aggagactta tcagccaatc acagcgccgg atccaccgt aggttgggtt gggtgggagc       300 accctccac agagtagagt caaacagcag cagcaacatg atagttgggg gtgtgcgtgt       360
taaaggaaaa aaagaagct tgggttatat tcccgctcta tttagaggtt gcgggataga       420
cgccgacgga gggcaatggc gccatggaac cttgcggata tcgatacgcc gcggcggact       480
gcgtccgaac cagctccagc agcgtttttt ccggccatt gagccgactg cgaccccgcc       540
aacgtgtctt ggcccacgca ctcatgtcat gttggtgttg ggaggccact ttttaagtag       600
cacaaggcac ctagctcgca gcaaggtgtc cgaaccaaag aagcggctgc agtggtgcaa       660
acggggcgga aacggcggga aaagccacg ggggcacgaa ttgaggcacg ccctcgaatt        720
tgagacgagt cacggcccca ttcgcccgcg caatggctcg ccaacgcccg gtcttttgca      780
ccacatcagg ttaccccaag ccaaacccttt gtgttaaaaa gcttaacata ttataccgaa      840
cgtaggtttg gcgggcttg ctccgtctgt ccaaggcaac atttatataa gggtctgcat        900
cgccggctca attgaatctt ttttcttctt ctcttctcta tattcattct tgaattaaac      960
acacatcaat ccgcggccgc caccgcggcc cgagattccg gcctcttcgg ccgccaagcg      1020
acccgggtgg acgtctagag gtacctagca attaacagat agtttgccgg tgataattct      1080
cttaacctcc cacactcctt tgacataacg atttatgtaa cgaaactgaa atttgaccag      1140
atattgtgtc gcggtggag ctccagcttt tgttcccttt agtgagggtt aatttcgagc      1200
```

```
ttggcgtaat catggtcata gctgtttcct gtgtgaaatt gttatccgct cacaattcca   1260
cacaacgtac gagccggaag cataaagtgt aaagcctggg gtgcctaatg agtgagctaa   1320
ctcacattaa ttgcgttgcg ctcactgccc gctttccagt cgggaaacct gtcgtgccag   1380
ctgcattaat gaatcggcca acgcgcgggg agaggcggtt tgcgtattgg gcgctcttcc   1440
gcttcctcgc tcactgactc gctgcgctcg gtcgttcggc tgcggcgagc ggtatcagct   1500
cactcaaagg cggtaatacg gttatccaca gaatcagggg ataacgcagg aaagaacatg   1560
tgagcaaaag gccagcaaaa ggccaggaac cgtaaaaagg ccgcgttgct ggcgtttttc   1620
cataggctcc gcccccctga cgagcatcac aaaaatcgac gctcaagtca gaggtggcga   1680
aacccgacag gactataaag ataccaggcg tttccccctg gaagctccct cgtgcgctct   1740
cctgttccga ccctgccgct taccggatac ctgtccgcct ttctcccttc gggaagcgtg   1800
gcgctttctc atagctcacg ctgtaggtat ctcagttcgg tgtaggtcgt tcgctccaag   1860
ctgggctgtg tgcacgaacc ccccgttcag cccgaccgct gcgccttatc cggtaactat   1920
cgtcttgagt ccaacccggt aagacacgac ttatcgccac tggcagcagc cactggtaac   1980
aggattagca gagcgaggta tgtaggcggt gctacagagt tcttgaagtg gtggcctaac   2040
tacggctaca ctagaaggac agtatttggt atctgcgctc tgctgaagcc agttaccttc   2100
ggaaaaagag ttggtagctc ttgatccggc aaacaaacca ccgctggtag cggtggtttt   2160
tttgtttgca agcagcagat tacgcgcaga aaaaaaggat ctcaagaaga tcctttgatc   2220
ttttctacgg ggtctgacgc tcagtggaac gaaaactcac gttaagggat tttggtcatg   2280
agattatcaa aaaggatctt cacctagatc cttttaaatt aaaaatgaag ttttaaatca   2340
atctaaagta tatatgagta aacttggtct gacagttacc aatgcttaat cagtgaggca   2400
cctatctcag cgatctgtct atttcgttca tccatagttg cctgactccc cgtcgtgtag   2460
ataactacga tacgggaggg cttaccatct ggccccagtg ctgcaatgat accgcgagac   2520
ccacgctcac cggctccaga tttatcagca ataaaccagc cagccggaag ggccgagcgc   2580
agaagtggtc ctgcaacttt atccgcctcc atccagtcta ttaattgttg ccgggaagct   2640
agagtaagta gttcgccagt taatagtttg cgcaacgttg ttgccattgc tacaggcatc   2700
gtggtgtcac gctcgtcgtt tggtatggct tcattcagct ccggttccca acgatcaagg   2760
cgagttacat gatcccccat gttgtgcaaa aaagcggtta gctccttcgg tcctccgatc   2820
gttgtcagaa gtaagttggc cgcagtgtta tcactcatgg ttatggcagc actgcataat   2880
tctcttactg tcatgccatc cgtaagatgc ttttctgtga ctggtgagta ctcaaccaag   2940
tcattctgag aatagtgtat gcggcgaccg agttgctctt gcccggcgtc aatacgggat   3000
aataccgcgc cacatagcag aactttaaaa gtgctcatca ttggaaaacg ttcttcgggg   3060
cgaaaactct caaggatctt accgctgttg agatccagtt cgatgtaacc cactcgtgca   3120
cccaactgat cttcagcatc ttttactttc accagcgttt ctgggtgagc aaaaacagga   3180
aggcaaaatg ccgcaaaaaa gggaataagg gcgacacgga aatgttgaat actcatactc   3240
ttcctttttc aatattattg aagcatttat cagggttatt gtctcatgag cggatacata   3300
tttgaatgta tttagaaaaa taaacaaata ggggttccgc gcacatttcc ccgaaaagtg   3360
ccacctgacg cgccctgtag cggcgcatta agcgcggcgg gtgtggtggt tacgcgcagc   3420
gtgaccgcta cacttgccag cgccctagcg cccgctcctt tcgctttctt cccttccttt   3480
ctcgccacgt tcgccggctt tccccgtcaa gctctaaatc gggggctccc tttagggttc   3540
```

```
cgatttagtg ctttacggca cctcgacccc aaaaaacttg attagggtga tggttcacgt    3600
agtgggccat cgccctgata gacggttttt cgcccttga cgttggagtc cacgttcttc    3660
aatagtggac tcttgttcca aactggaaca acactcaacc ctatctcggt ctattctttt    3720
gatttataag ggattttgcc gatttcggcc tattggttaa aaaatgagct gatttaacaa    3780
aaatttaacg cgaattttaa caaaatatta acgcttacaa tttccattcg ccattcaggc    3840
tgcgcaactg ttgggaaggg cgatcggtgc gggcctcttc gctattacgc cagctggcga    3900
aaggggatg tgctgcaagg cgattaagtt gggtaacgcc agggttttcc cagtcacgac    3960
gttgtaaaac gacggccagt gaattgtaat acgactcact atagggcgaa ttgggtaccg    4020
ggccccccct cgaggtcgat ggtgtcgata agcttgatat cgaattcatg tcacacaaac    4080
cgatcttcgc ctcaaggaaa cctaattcta catccgagag actgccgaga tccagtctac    4140
actgattaat tttcgggcca ataatttaaa aaaatcgtgt tatataatat tatatgtatt    4200
atatatatac atcatgatga tactgacagt catgtcccat tgctaaatag acagactcca    4260
tctgccgcct ccaactgatg ttctcaatat ttaaggggtc atctcgcatt gtttaataat    4320
aaacagactc catctaccgc ctccaaatga tgttctcaaa atatattgta tgaacttatt    4380
tttattactt agtattatta gacaacttac ttgctttatg aaaaacactt cctatttagg    4440
aaacaattta taatggcagt tcgttcattt aacaatttat gtagaataaa tgttataaat    4500
gcgtatggga atcttaaat atggatagca taaatgatat ctgcattgcc taattcgaaa    4560
tcaacagcaa cgaaaaaaat cccttgtaca acataaatag tcatcgagaa atatcaacta    4620
tcaaagaaca gctattcaca cgttactatt gagattatta ttggacgaga atcacacact    4680
caactgtctt tctctcttct agaaatacag gtacaagtat gtactattct cattgttcat    4740
acttctagtc atttcatccc acatattcct tggatttctc tccaatgaat gacattctat    4800
cttgcaaatt caacaattat aataagatat accaaagtag cggtatagtg gcaatcaaaa    4860
agcttctctg gtgtgcttct cgtatttatt tttattctaa tgatccatta aggtatata    4920
tttatttctt gttatataat ccttttgttt attacatggg ctggatacat aaaggtattt    4980
tgatttaatt ttttgcttaa attcaatccc ccctcgttca gtgtcaactg taatggtagg    5040
aaattaccat acttttgaag aagcaaaaaa aatgaaagaa aaaaaaaatc gtatttccag    5100
gttagacgtt ccgcagaatc tagaatgcgg tatgcggtac attgttcttc gaacgtaaaa    5160
gttgcgctcc ctgagatatt gtacattttt gcttttacaa gtacaagtac atcgtacaac    5220
tatgtactac tgttgatgca tccacaacag tttgttttgt tttttttgt ttttttttt     5280
tctaatgatt cattaccgct atgtatacct acttgtactt gtagtaagcc gggttattgg    5340
cgttcaatta atcatagact tatgaatctg cacggtgtgc gctgcgagtt acttttagct    5400
tatgcatgct acttgggtgt aatattggga tctgttcgga aatcaacgga tgctcaaccg    5460
atttcgacag taattaatta agtcatacac aagtcagctt tcttcgagcc tcatataagt    5520
ataagtagtt caacgtatta gcactgtacc cagcatctcc gtatcgagaa acacaacaac    5580
atgccccatt ggacagatca tgcggataca caggttgtgc agtatcatac atactcgatc    5640
agacaggtcg tctgaccatc atacaagctg aacaagcgct ccatacttgc acgctctcta    5700
tatacacagt taaattacat atccatagtc taacctctaa cagttaatct tctggtaagc    5760
ctcccagcca gccttctggt atcgcttggc ctcctcaata ggatctcggt tctggccgta    5820
cagacctcgg ccgacaatta tgatatccgt tccggtagac atgacatcct caacagttcg    5880
gtactgctgt ccgagagcgt ctcccttgtc gtcaagaccc accccggggg tcagaataag    5940
```

```
ccagtcctca gagtcgccct taggtcggtt ctgggcaatg aagccaacca caaactcggg    6000
gtcggatcgg gcaagctcaa tggtctgctt ggagtactcg ccagtggcca gagagccctt    6060
gcaagacagc tcggccagca tgagcagacc tctggccagc ttctcgttgg gagaggggac    6120
taggaactcc ttgtactggg agttctcgta gtcagagacg tcctccttct tctgttcaga    6180
gacagtttcc tcggcaccag ctcgcaggcc agcaatgatt ccggttccgg gtacaccgtg    6240
ggcgttggtg atatcggacc actcggcgat tcggtgacac cggtactggt gcttgacagt    6300
gttgccaata tctgcgaact ttctgtcctc gaacaggaag aaaccgtgct taagagcaag    6360
ttccttgagg gggagcacag tgccggcgta ggtgaagtcg tcaatgatgt cgatatgggt    6420
tttgatcatg cacacataag gtccgacctt atcggcaagc tcaatgagct ccttggtggt    6480
ggtaacatcc agagaagcac acaggttggt tttcttggct gccacgagct tgagcactcg    6540
agcggcaaag gcggacttgt ggacgttagc tcgagcttcg taggagggca ttttggtggt    6600
gaagaggaga ctgaaataaa tttagtctgc agaactttt atcggaacct tatctggggc    6660
agtgaagtat atgttatggt aatagttacg agttagttga acttatagat agactggact    6720
atacggctat cggtccaaat tagaaagaac gtcaatggct ctctgggcgt cgcctttgcc    6780
gacaaaaatg tgatcatgat gaaagccagc aatgacgttg cagctgatat tgttgtcggc    6840
caaccgcgcc gaaaacgcag ctgtcagacc cacagcctcc aacgaagaat gtatcgtcaa    6900
agtgatccaa gcacactcat agttggagtc gtactccaaa ggcggcaatg acgagtcaga    6960
cagatactcg                                                            6970

<210> SEQ ID NO 71
<211> LENGTH: 968
<212> TYPE: DNA
<213> ORGANISM: Yarrowia lipolytica
<300> PUBLICATION INFORMATION:
<302> TITLE: GLYCERALDEHYDE-3-PHOSPHATE DEHYDROGENASE AND
      PHOSPHOGLYCERATE MUTASE PROMOTERS FOR GENE EXPRESSION IN
      OLEAGINOUS YEAST
<310> PATENT DOCUMENT NUMBER: US-2005-0014270-A1
<311> PATENT FILING DATE: 2004-06-16
<312> PUBLICATION DATE: 2005-01-20
<313> RELEVANT RESIDUES: (1)..(968)

<400> SEQUENCE: 71
tcgacgcagt aggatgtcct gcacgggtct ttttgtgggg tgtggagaaa ggggtgcttg      60
gagatggaag ccggtagaac cgggctgctt gtgcttggag atggaagccg gtagaaccgg     120
gctgcttggg gggatttggg gccgctgggc tccaaagagg ggtaggcatt tcgttgggt     180 tacgtaattg cggcatttgg gtcctgcgcg catgtcccat tggtcagaat tagtccggat     240
aggagactta tcagccaatc acagcgccgg atccacctgt aggttgggtt gggtgggagc    300
acccctccac agagtagagt caaacagcag cagcaacatg atagttgggg gtgtgcgtgt    360
taaaggaaaa aaaagaagct tgggttatat tcccgctcta tttagaggtt gcgggataga    420
cgccgacgga gggcaatggc gccatggaac cttgcggata tcgatacgcc gcggcggact    480
gcgtccgaac cagctccagc agcgtttttt ccgggccatt gagccgactg cgaccccgcc    540
aacgtgtctt ggcccacgca ctcatgtcat gttggtgttg ggaggccact ttttaagtag    600
cacaaggcac ctagctcgca gcaaggtgtc cgaaccaaag aagcggctgc agtggtgcaa    660
acggggcgga aacggcggga aaagccacg ggggcacgaa ttgaggcacg ccctcgaatt    720
tgagacgagt cacggcccca ttcgcccgcg caatggctcg ccaacgcccg gtcttttgca    780
```

-continued

| | |
|---|---|
| ccacatcagg ttaccccaag ccaaacctttt gtgttaaaaa gcttaacata ttataccgaa | 840 |
| cgtaggtttg ggcgggcttg ctccgtctgt ccaaggcaac atttatataa gggtctgcat | 900 |
| cgccggctca attgaatctt ttttcttctt ctcttctcta tattcattct tgaattaaac | 960 |
| acacatca | 968 |

<210> SEQ ID NO 72
<211> LENGTH: 8630
<212> TYPE: DNA
<213> ORGANISM: Artificial Sequence
<220> FEATURE:
<223> OTHER INFORMATION: Plasmid pYZDE2-S

<400> SEQUENCE: 72

| | |
|---|---|
| ggtggagctc cagcttttgt tccctttagt gagggttaat ttcgagcttg gcgtaatcat | 60 |
| ggtcatagct gtttcctgtg tgaaattgtt atccgctcac aattccacac aacgtacgag | 120 |
| ccggaagcat aaagtgtaaa gcctggggtg cctaatgagt gagctaactc acattaattg | 180 |
| cgttgcgctc actgcccgct ttccagtcgg gaaacctgtc gtgccagctg cattaatgaa | 240 |
| tcggccaacg cgcggggaga ggcggtttgc gtattgggcg ctcttccgct tcctcgctca | 300 |
| ctgactcgct gcgctcggtc gttcggctgc ggcgagcggt atcagctcac tcaaaggcgg | 360 |
| taatacggtt atccacagaa tcaggggata acgcaggaaa gaacatgtga gcaaaaggcc | 420 |
| agcaaaaggc caggaaccgt aaaaaggccg cgttgctggc gtttttccat aggctccgcc | 480 |
| cccctgacga gcatcacaaa aatcgacgct caagtcagag gtggcgaaac ccgacaggac | 540 |
| tataaagata ccaggcgttt ccccctggaa gctccctcgt gcgctctcct gttccgaccc | 600 |
| tgccgcttac cggatacctg tccgcctttc tcccttcggg aagcgtggcg ctttctcata | 660 |
| gctcacgctg taggtatctc agttcggtgt aggtcgttcg ctccaagctg ggctgtgtgc | 720 |
| acgaaccccc cgttcagccc gaccgctgcg ccttatccgg taactatcgt cttgagtcca | 780 |
| acccggtaag acacgactta tcgccactgg cagcagccac tggtaacagg attagcagag | 840 |
| cgaggtatgt aggcggtgct acagagttct tgaagtggtg gcctaactac ggctacacta | 900 |
| gaaggacagt atttggtatc tgcgctctgc tgaagccagt taccttcgga aaaagagttg | 960 |
| gtagctcttg atccggcaaa caaaccaccg ctggtagcgg tggttttttt gtttgcaagc | 1020 |
| agcagattac gcgcagaaaa aaaggatctc aagaagatcc tttgatcttt tctacggggt | 1080 |
| ctgacgctca gtggaacgaa aactcacgtt aagggatttt ggtcatgaga ttatcaaaaa | 1140 |
| ggatcttcac ctagatcctt ttaaattaaa aatgaagttt taaatcaatc taagtatat | 1200 |
| atgagtaaac ttggtctgac agttaccaat gcttaatcag tgaggcacct atctcagcga | 1260 |
| tctgtctatt tcgttcatcc atagttgcct gactccccgt cgtgtagata actacgatac | 1320 |
| gggagggctt accatctggc cccagtgctg caatgatacc gcgagaccca cgctcaccgg | 1380 |
| ctccagattt atcagcaata aaccagccag ccggaagggc cgagcgcaga agtggtcctg | 1440 |
| caactttatc cgcctccatc cagtctatta attgttgccg ggaagctaga gtaagtagtt | 1500 |
| cgccagttaa tagtttgcgc aacgttgttg ccattgctac aggcatcgtg gtgtcacgct | 1560 |
| cgtcgtttgg tatggcttca ttcagctccg gttcccaacg atcaaggcga gttacatgat | 1620 |
| cccccatgtt gtgcaaaaaa gcggttagct ccttcggtcc tccgatcgtt gtcagaagta | 1680 |
| agttggccgc agtgttatca ctcatggtta tggcagcact gcataattct cttactgtca | 1740 |
| tgccatccgt aagatgcttt tctgtgactg gtgagtacta accaagtca ttctgagaat | 1800 |
| agtgtatgcg gcgaccgagt tgctcttgcc cggcgtcaat acgggataat accgcgccac | 1860 |

-continued

```
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040 caaaaaggg  aataagggcg acacggaaat gttgaatact catactcttc cttttcaat     2100 attattgaag catttatcag ggttattgtc tcatgagcgg atacatattt gaatgtattt    2160
agaaaaataa acaaataggg gttccgcgca catttccccg aaaagtgcca cctgacgcgc    2220
cctgtagcgg cgcattaagc gcggcgggtg tggtggttac gcgcagcgtg accgctacac    2280
ttgccagcgc cctagcgccc gctcctttcg ctttcttccc ttcctttctc gccacgttcg    2340
ccggctttcc ccgtcaagct ctaaatcggg ggctcccttt agggttccga tttagtgctt    2400
tacggcacct cgaccccaaa aaacttgatt agggtgatgg ttcacgtagt gggccatcgc    2460
cctgatagac ggttttttcgc cctttgacgt tggagtccac gttctttaat agtggactct    2520
tgttccaaac tggaacaaca ctcaaccccta tctcggtcta ttcttttgat ttataaggga    2580
ttttgccgat ttcggcctat tggttaaaaa atgagctgat ttaacaaaaa tttaacgcga    2640
attttaacaa aatattaacg cttacaattt ccattcgcca ttcaggctgc gcaactgttg    2700
ggaagggcga tcggtgcggg cctcttcgct attacgccag ctggcgaaag ggggatgtgc    2760
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtatttga  tttaattttt    3840 tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta cattttgct  tttacaagta caagtacatc gtacaactat gtactactgt    4080
tgatgcatcc acaacagttt gttttgtttt ttttgttttt tttttttct  aatgattcat    4140 taccgctatg tatacctact tgtacttgta gtaagccggg ttattggcgt tcaattaatc    4200
```

```
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
agaggtctgt gactgtcagt acaaggtgcc ttcattatgc cctcaacctt accatacctc    4440
actgaatgta gtgtacctct aaaaatgaaa tacagtgcca aaagccaagg cactgagctc    4500
gtctaacgga cttgatatac aaccaattaa aacaaatgaa aagaaataca gttctttgta    4560
tcatttgtaa caattaccct gtacaaacta aggtattgaa atcccacaat attcccaaag    4620 tccaccccttt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactacaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc tttttataga gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
atatcggcgg tagtgatacc agcctcgacg gactccttga cggcagcctc aacagcgtca    5220
ccggcgggct tcatgttaag agagaacttg agcatcatgg cggcagacag aatggtggca    5280
atggggttga ccttctgctt gccgagatcg ggggcagatc cgtgacaggg ctcgtacaga    5340
ccgaacgcct cgttggtgtc gggcagagaa gccagagagg cggagggcag cagacccaga    5400
gaaccgggga tgacggaggc ctcgtcggag atgatatcgc caaacatgtt ggtggtgatg    5460
atgataccat tcatcttgga gggctgcttg atgaggatca tggcggccga gtcgatcagc    5520
tggtggttga gctcgagctg ggggaattcg tccttgagga ctcgagtgac agtctttcgc    5580
caaagtcgag aggaggccag cacgttggcc ttgtcaagag accacacggg aagaggggggg    5640 ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760
atacctccga cgagctctcg gacaatgatg aagtcggtgc cctcaacgtt tcggatgggg    5820
gagagatcgg cgagcttggg cgacagcagc tggcagggtc gcaggttggc gtacaggttc    5880
aggtcctttc gcagcttgag gagaccctgc tcgggtcgca cgtcggttcg tccgtcggga    5940
gtggtccata cggtgttggc agcgcctccg acagcaccga gcataataga gtcagccttt    6000
cggcagatgt cgagagtagc gtcggtgatg ggctcgccct ccttctcaat ggcagctcct    6060
ccaatgagtc ggtcctcaaa cacaaactcg gtgccggagg cctcagcaac agacttgagc    6120
accttgacgg cctcggcaat cacctcgggg ccacagaagt cgccgccgag aagaacaatc    6180
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300
gcacttttgc ccgtgctatg tggaagacta aacctccgaa gattgtgact caggtagtgc    6360
ggtatcggct agggacccaa accttgtcga tgccgatagc gctatcgaac gtaccccagc    6420
cggccgggag tatgtcggag gggacatacg agatcgtcaa gggtttgtgg ccaactggta    6480
aatttaaatg atgtcgacgc agtaggatgt cctgcacggg tcttttttgtg gggtgtggag    6540 aaaggggtgc ttggagatgg aagccggtag aaccgggctg cttgtgcttg gagatggaag    6600
```

```
ccggtagaac cgggctgctt gggggattt ggggccgctg ggctccaaag aggggtaggc    6660
atttcgttgg ggttacgtaa ttgcggcatt tgggtcctgc gcgcatgtcc cattggtcag    6720
aattagtccg gataggagac ttatcagcca atcacagcgc cggatccacc tgtaggttgg    6780
gttgggtggg agcacccctc cacagagtag agtcaaacag cagcagcaac atgatagttg    6840
ggggtgtgcg tgtaaagga aaaaaagaa gcttgggtta tattcccgct ctatttagag      6900
gttgcgggat agacgccgac ggagggcaat ggcgccatgg aaccttgcgg atatcgatac    6960 gccgcggcg actgcgtccg aaccagctcc agcagcgttt tttccgggcc attgagccga     7020
ctgcgacccc gccaacgtgt cttggcccac gcactcatgt catgttggtg ttgggaggcc    7080 acttttaag tagcacaagg cacctagctc gcagcaaggt gtccgaacca agaagcggc      7140 tgcagtggtg caaacggggc ggaaacggcg ggaaaaagcc acggggcac gaattgaggc     7200 acgccctcga atttgagacg agtcacggcc ccattcgccc gcgcaatggc tcgccaacgc    7260
ccggtctttt gcaccacatc aggttacccc aagccaaacc tttgtgttaa aaagcttaac    7320
atattatacc gaacgtaggt ttgggcgggc ttgctccgtc tgtccaaggc aacatttata    7380
taagggtctg catcgccggc tcaattgaat ctttttctt cttctcttct ctatattcat     7440
tcttgaatta aacacacatc aatccatggc aaacagcagc gtgtgggatg atgtggtggg    7500
ccgcgtggag accggcgtgg accagtggat ggatggcgcc aagccgtacg cactcaccga    7560
tgggctcccg atgatggacg tgtccaccat gctggcattc gaggtgggat acatggccat    7620
gctgctcttc ggcatcccga tcatgaagca gatggagaag ccttttgagc tcaagaccat    7680
caagctcttg cacaacttgt ttctcttcgg actttccttg tacatgtgcg tggagaccat    7740
ccgccaggct atcctcggag gctacaaagt gtttggaaac gacatggaga agggcaacga    7800
gtctcatgct cagggcatgt ctcgcatcgt gtacgtgttc tacgtgtcca aggcatacga    7860
gttcttggat accgccatca tgatcctttg caagaagttc aaccaggttt ccttcttgca    7920
tgtgtaccac catgccactc atttttgcca tctggtgggc tatccgccaa gtacgctcca    7980
ggaggtgatg cgtactttt cagtgatcct caactctttc gtgcacaccg tcatgtacgg    8040
catactactt cttctcctcc caagggttcg ggttcgtgaa gccaatcaag ccgtacatca    8100
ccacccttca gatgacccag ttcatggcaa tgcttgtgca gtccttgtac gactacctct    8160
tcccatgcga ctacccacag gctcttgtgc agctccttgg agtgtacatg atcaccttgc    8220
ttgccctctt cggcaacttt tttgtgcaga gctatcttaa aaagccaaaa aagagcaaga    8280
ccaactaaaa ctgcctgcat gatatgccgc tcgccggcgt tcgaattgac tcagaaagcg    8340
agttaaggcg acacgcaaac tctatatttt ttcaaacgtg ttgccgtcac tcattcgcca    8400
tctgtttact acgtgtctgt tcaatgagca tgttcttgaa tctaaagaat ctcgaatgtt    8460
ttttaaaaaa agaattcgat atcaagctta cgcgtcgacc cggtggacg tctagaggta    8520 cctagcaatt aacagatagt ttgccggtga taattctctt aacctccac actcctttga    8580 cataacgatt tatgtaacga aactgaaatt tgaccagata ttgtgtccgc                8630
```

<210> SEQ ID NO 73
<211> LENGTH: 18
<212> TYPE: DNA
<213> ORGANISM: Artificial Sequence
<220> FEATURE:
<223> OTHER INFORMATION: Primer GPDsense

<400> SEQUENCE: 73

```
atacgagatc gtcaaggg                                                      18
```

<210> SEQ ID NO 74
<211> LENGTH: 26
<212> TYPE: DNA
<213> ORGANISM: Artificial Sequence
<220> FEATURE:
<223> OTHER INFORMATION: Primer GPDantisense

<400> SEQUENCE: 74

```
gcggccgcgg attgatgtgt gtttaa                                             26
```

<210> SEQ ID NO 75
<211> LENGTH: 6339
<212> TYPE: DNA
<213> ORGANISM: Artificial Sequence
<220> FEATURE:
<223> OTHER INFORMATION: Plasmid pKR136
<220> FEATURE:
<221> NAME/KEY: misc_feature
<222> LOCATION: (4078)..(4078)
<223> OTHER INFORMATION: n is a, c, g, or t

<400> SEQUENCE: 75

```
ggccgcgaca caagtgtgag agtactaaat aaatgctttg gttgtacgaa atcattacac         60
taaataaaat aatcaaagct tatatatgcc ttccgctaag gccgaatgca agaaattgg         120
ttctttctcg ttatcttttg ccacttttac tagtacgtat taattactac ttaatcatct        180
ttgtttacgg ctcattatat ccgtacgtcg agtcgacctg caggcatgca agcttggcgt        240
aatcatggtc atagctgttt cctgtgtgaa attgttatcc gctcacaatt ccacacaaca        300
tacgagccgg aagcataaag tgtaaagcct ggggtgccta atgagtgagc taactcacat        360
taattgcgtt gcgctcactg cccgctttcc agtcgggaaa cctgtcgtgc cagctgcatt        420
aatgaatcgg ccaacgcgcg gggagaggcg gtttgcgtat tgggcgctct tccgcttcct        480
cgctcactga ctcgctgcgc tcggtcgttc ggctgcggcg agcggtatca gctcactcaa        540
aggcggtaat acggttatcc acagaatcag gggataacgc aggaaagaac atgtgagcaa        600
aaggccagca aaaggccagg aaccgtaaaa aggccgcgtt gctggcgttt ttccataggc        660
tccgcccccc tgacgagcat cacaaaaatc gacgctcaag tcagaggtgg cgaaacccga        720
caggactata aagataccag gcgtttcccc ctggaagctc cctcgtgcgc tctcctgttc        780
cgaccctgcc gcttaccgga tacctgtccg cctttctccc ttcgggaagc gtggcgcttt        840
ctcatagctc acgctgtagg tatctcagtt cggtgtaggt cgttcgctcc aagctgggct        900
gtgtgcacga accccccgtt cagcccgacc gctgcgcctt atccggtaac tatcgtcttg        960
agtccaaccc ggtaagacac gacttatcgc cactggcagc agccactggt aacaggatta       1020
gcagagcgag gtatgtaggc ggtgctacag agttcttgaa gtggtggcct aactacggct       1080
acactagaag gacagtattt ggtatctgcg ctctgctgaa gccagttacc ttcggaaaaa       1140
gagttggtag ctcttgatcc ggcaaacaaa ccaccgctgg tagcggtggt ttttttgttt       1200
gcaagcagca gattacgcgc agaaaaaaag gatctcaaga agatcctttg atctttcta        1260
cggggtctga cgctcagtgg aacgaaaact cacgttaagg gattttggtc atgagattat       1320
caaaaggat cttcacctag atccttttaa attaaaatg aagttttaaa tcaatctaaa         1380
gtatatatga gtaaacttgg tctgacagtt accaatgctt aatcagtgag gcacctatct       1440
cagcgatctg tctatttcgt tcatccatag ttgcctgact ccccgtcgtg tagataacta       1500
cgatacggga gggcttacca tctggcccca gtgctgcaat gataccgcga gacccacgct       1560
```

-continued

```
caccggctcc agatttatca gcaataaacc agccagccgg aagggccgag cgcagaagtg    1620
gtcctgcaac tttatccgcc tccatccagt ctattaattg ttgccgggaa gctagagtaa    1680
gtagttcgcc agttaatagt ttgcgcaacg ttgttgccat tgctacaggc atcgtggtgt    1740
cacgctcgtc gtttggtatg gcttcattca gctccggttc ccaacgatca aggcgagtta    1800
catgatcccc catgttgtgc aaaaaagcgg ttagctcctt cggtcctccg atcgttgtca    1860
gaagtaagtt ggccgcagtg ttatcactca tggttatggc agcactgcat aattctctta    1920
ctgtcatgcc atccgtaaga tgcttttctg tgactggtga gtactcaacc aagtcattct    1980
gagaatagtg tatgcggcga ccgagttgct cttgcccggc gtcaatacgg gataataccg    2040
cgccacatag cagaacttta aaagtgctca tcattggaaa acgttcttcg ggcgaaaac    2100 tctcaaggat cttaccgctg ttgagatcca gttcgatgta acccactcgt gcacccaact    2160
gatcttcagc atcttttact ttcaccagcg tttctgggtg agcaaaaaca ggaaggcaaa    2220
atgccgcaaa aagggaata agggcgacac ggaaatgttg aatactcata ctcttccttt    2280
ttcaatatta ttgaagcatt tatcagggtt attgtctcat gagcggatac atatttgaat    2340
gtatttagaa aaataaacaa ataggggttc cgcgcacatt tccccgaaaa gtgccacctg    2400
acgtctaaga aaccattatt atcatgacat aacctataa aaataggcgt atcacgaggc    2460
cctttcgtct cgcgcgtttc ggtgatgacg gtgaaaacct ctgacacatg cagctcccgg    2520
agacggtcac agcttgtctg taagcggatg ccgggagcag acaagcccgt cagggcgcgt    2580
cagcgggtgt tggcgggtgt cggggctggc ttaactatgc ggcatcagag cagattgtac    2640
tgagagtgca ccatatgcgg tgtgaaatac cgcacagatg cgtaaggaga aaataccgca    2700
tcaggcgcca ttcgccattc aggctgcgca actgttggga agggcgatcg gtgcgggcct    2760
cttcgctatt acgccagctg gcgaaagggg gatgtgctgc aaggcgatta agttgggtaa    2820
cgccagggtt ttcccagtca cgacgttgta aaacgacggc cagtgaattc gagctcggta    2880
cccggggatc ctctagacgt acgtcctcga agagaagggt taataacaca tttttttaaca    2940 tttttaacac aaattttagt tatttaaaaa tttattaaaa aatttaaaat aagaagagga    3000
actctttaaa taaatctaac ttacaaaatt tatgattttt aataagtttt caccaataaa    3060
aaatgtcata aaaatatgtt aaaaagtata ttatcaatat tctctttatg ataaataaaa    3120 agaaaaaaa aataaaagtt aagtgaaaat gagattgaag tgactttagg tgtgtataaa    3180
tatatcaacc ccgccaacaa tttatttaat ccaaatatat tgaagtatat tattccatag    3240
cctttattta tttatatatt tattatataa aagctttatt tgttctaggt tgttcatgaa    3300
atattttttt ggtttatct ccgttgtaag aaaatcatgt gctttgtgtc gccactcact    3360
attgcagctt tttcatgcat tggtcagatt gacggttgat tgtattttg tttttatgg    3420 ttttgtgtta tgacttaagt cttcatctct ttatctcttc atcaggtttg atggttacct    3480
aatatggtcc atgggtacat gcatggttaa attaggtggc caactttgtt gtgaacgata    3540 gaatttttt tatattaagt aaactatttt tatattatga ataataata aaaaaaatat    3600 tttatcatta ttaacaaaat catattagtt aatttgttaa ctctataata aagaaatac    3660 tgtaacattc acattacatg gtaacatctt tccacccttt catttgtttt tgttttgatg    3720 acttttttc ttgtttaaat ttatttccct tctttaaat ttggaataca ttatcatcat    3780
atataaacta aaatactaaa aacaggatta cacaaatgat aaataataac acaaatattt    3840
ataaatctag ctgcaatata tttaaactag ctatatcgat attgtaaaat aaaactagct    3900
```

```
gcattgatac tgataaaaaa atatcatgtg cttcctggac tgatgatgca gtatactttt    3960
gacattgcct ttattttatt tttcagaaaa gctttcttag ttctgggttc ttcattattt    4020
gtttcccatc tccattgtga attgaatcat ttgcttcgtg tcacaaatac aatttagnta    4080
ggtacatgca ttggtcagat tcacggttta ttatgtcatg acttaagttc atggtagtac    4140
attacctgcc acgcatgcat tatattggtt agatttgata ggcaaatttg gttgtcaaca    4200
atataaatat aaataatgtt tttatattac gaaataacag tgatcaaaac aaacagtttt    4260
atctttatta acaagatttt gtttttgttt gatgacgttt tttaatgttt acgctttccc    4320
ccttcttttg aatttagaac actttatcat cataaaatca aatactaaaa aaattacata    4380
tttcataaat aataacacaa atattttaa aaaatctgaa ataataatga acaatattac     4440
atattatcac gaaaattcat taataaaaat attatataaa taaaatgtaa tagtagttat    4500
atgtaggaaa aaagtactgc acgcataata tatacaaaaa gattaaaatg aactattata    4560
aataataaca ctaaattaat ggtgaatcat atcaaaataa tgaaaagta aataaaattt     4620 gtaattaact tctatatgta ttacacacac aaataataaa taatagtaaa aaaaattatg    4680
ataaatattt accatctcat aagatattta aaataatgat aaaatatag attatttttt     4740 atgcaactag ctagccaaaa agagaacacg ggtatatata aaagagtac ctttaaattc     4800 tactgtactt cctttattcc tgacgttttt atatcaagtg gacatacgtg aagattttaa    4860
ttatcagtct aaatatttca ttagcactta atactttctt gttttattcc tatcctataa    4920
gtagtcccga ttctcccaac attgcttatt cacacaacta actaagaaag tcttccatag    4980
ccccccaagc ggccgcatgg gaacggacca aggaaaaacc ttcacctggg aagagctggc    5040
ggcccataac accaaggacg acctactctt ggccatccgc ggcagggtgt acgatgtcac    5100
aaagttcttg agccgccatc ctggtggagt ggacactctc ctgctcggag ctggccgaga    5160
tgttactccg gtctttgaga tgtatcacgc gtttggggct gcagatgcca ttatgaagaa    5220
gtactatgtc ggtacactgg tctcgaatga gctgcccatc ttcccggagc caacggtgtt    5280
ccacaaaacc atcaagacga gagtcgaggg ctactttacg gatcggaaca ttgatcccaa    5340
gaatagacca gagatctggg gacgatacgc tcttatcttt ggatccttga tcgcttccta    5400
ctacgcgcag ctcttttgtgc ctttcgttgt cgaacgcaca tggcttcagg tggtgtttgc    5460
aatcatcatg ggatttgcgt gcgcacaagt cggactcaac cctcttcatg atgcgtctca    5520
cttttcagtg acccacaacc ccactgtctg gaagattctg ggagccacgc acgactttt     5580 caacggagca tcgtacctgg tgtggatgta ccaacatatg ctcggccatc accctacac     5640 caacattgct ggagcagatc ccgacgtgtc gacgtctgag cccgatgttc gtcgtatcaa    5700
gcccaaccaa aagtggtttg tcaaccacat caaccagcac atgtttgttc ctttcctgta    5760
cggactgctg gcgttcaagg tgcgcattca ggacatcaac attttgtact tgtcaagac     5820 caatgacgct attcgtgtca atcccatctc gacatgcac actgtgatgt tctggggcgg     5880
caaggctttc tttgtctggt atcgcctgat tgttcccctg cagtatctgc cctgggcaa     5940 ggtgctgctc ttgttcacgg tcgcggacat ggtgtcgtct tactggctgg cgctgacctt    6000
ccaggcgaac cacgttgttg aggaagttca gtggccgttg cctgacgaga cgggatcat     6060 ccaaaaggac tgggcagcta tgcaggtcga gactacgcag gattacgcac acgattcgca    6120
cctctggacc agcatcactg gcagcttgaa ctaccaggct gtgcaccatc tgttccccaa    6180
cgtgtcgcag caccattatc ccgatattct ggcatcatc aagaacacct gcagcgagta     6240
caaggttcca taccttgtca aggatacgtt ttggcaagca tttgcttcac atttggagca    6300
```

-continued

```
cttgcgtgtt cttggactcc gtcccaagga agagtaggc                            6339

<210> SEQ ID NO 76
<211> LENGTH: 8319
<212> TYPE: DNA
<213> ORGANISM: Artificial Sequence
<220> FEATURE:
<223> OTHER INFORMATION: Plasmid pY98

<400> SEQUENCE: 76
ggccgccacc gcggcccgag attccggcct cttcggccgc caagcgaccc gggtggacgt      60
ctagaggtac ctagcaatta acagatagtt tgccggtgat aattctctta acctcccaca    120
ctcctttgac ataacgattt atgtaacgaa actgaaattt gaccagatat tgtgtccgcg    180
gtggagctcc agcttttgtt ccctttagtg agggttaatt tcgagcttgg cgtaatcatg    240
gtcatagctg tttcctgtgt gaaattgtta tccgctcaca attccacaca acgtacgagc    300
cggaagcata aagtgtaaag cctggggtgc ctaatgagtg agctaactca cattaattgc    360
gttgcgctca ctgcccgctt tccagtcggg aaacctgtcg tgccagctgc attaatgaat    420
cggccaacgc gcggggagag gcggtttgcg tattgggcgc tcttccgctt cctcgctcac    480
tgactcgctg cgctcggtcg ttcggctgcg gcgagcggta tcagctcact caaaggcggt    540
aatacggtta tccacagaat caggggataa cgcaggaaag aacatgtgag caaaaggcca    600
gcaaaaggcc aggaaccgta aaaaggccgc gttgctggcg ttttt ccata ggctccgccc    660 ccctgacgag catcacaaaa atcgacgctc aagtcagagg tggcgaaacc cgacaggact    720
ataaagatac caggcgtttc ccctggaag ctccctcgtg cgctctcctg ttccgaccct    780
gccgcttacc ggatacctgt ccgcctttct cccttcggga agcgtggcgc tttctcatag    840
ctcacgctgt aggtatctca gttcggtgta ggtcgttcgc tccaagctgg gctgtgtgca    900 cgaaccccc gttcagcccg accgctgcgc cttatccggt aactatcgtc ttgagtccaa    960
cccggtaaga cacgacttat cgccactggc agcagccact ggtaacagga ttagcagagc   1020
gaggtatgta ggcggtgcta cagagttctt gaagtggtgg cctaactacg gctacactag   1080
aaggacagta tttggtatct gcgctctgct gaagccagtt accttcggaa aaagagttgg   1140
tagctcttga tccggcaaac aaaccaccgc tggtagcggt ggttttttg tttgcaagca   1200 gcagattacg cgcagaaaaa aaggatctca agaagatcct ttgatctttt ctacggggtc   1260
tgacgctcag tggaacgaaa actcacgtta agggattttg gtcatgagat tatcaaaaag   1320
gatcttcacc tagatccttt taaattaaaa atgaagtttt aaatcaatct aaagtatata   1380
tgagtaaact tggtctgaca gttaccaatg cttaatcagt gaggcaccta tctcagcgat   1440
ctgtctattt cgttcatcca tagttgcctg actccccgtc gtgtagataa ctacgatacg   1500
ggagggctta ccatctggcc ccagtgctgc aatgataccg cgagacccac gctcaccggc   1560
tccagattta tcagcaataa accagccagc cggaagggcc gagcgcagaa gtggtcctgc   1620
aactttatcc gcctccatcc agtctattaa ttgttgccgg gaagctagag taagtagttc   1680
gccagttaat agtttgcgca acgttgttgc cattgctaca ggcatcgtgg tgtcacgctc   1740
gtcgtttggt atggcttcat tcagctccgg ttcccaacga tcaaggcgag ttacatgatc   1800
ccccatgttg tgcaaaaaag cggttagctc cttcggtcct ccgatcgttg tcagaagtaa   1860
gttggccgca gtgttatcac tcatggttat ggcagcactg cataattctc ttactgtcat   1920
gccatccgta agatgctttt ctgtgactgg tgagtactca accaagtcat tctgagaata   1980
```

-continued

```
gtgtatgcgg cgaccgagtt gctcttgccc ggcgtcaata cgggataata ccgcgccaca    2040
tagcagaact ttaaaagtgc tcatcattgg aaaacgttct tcggggcgaa aactctcaag    2100
gatcttaccg ctgttgagat ccagttcgat gtaacccact cgtgcaccca actgatcttc    2160
agcatctttt actttcacca gcgtttctgg gtgagcaaaa acaggaaggc aaaatgccgc    2220
aaaaaaggga ataagggcga cacggaaatg ttgaatactc atactcttcc ttttcaata    2280 ttattgaagc atttatcagg gttattgtct catgagcgga tacatatttg aatgtattta    2340
gaaaaataaa caaataggggg ttccgcgcac atttccccga aaagtgccac ctgacgcgcc    2400
ctgtagcggc gcattaagcg cggcgggtgt ggtggttacg cgcagcgtga ccgctacact    2460
tgccagcgcc ctagcgcccg ctcctttcgc tttcttccct tcctttctcg ccacgttcgc    2520
cggctttccc cgtcaagctc taaatcgggg ctcccttta gggttccgat ttagtgcttt    2580
acggcacctc gaccccaaaa aacttgatta gggtgatggt tcacgtagtg gccatcgcc    2640 ctgatagacg ttttttcgcc ctttgacgtt ggagtccacg ttctttaata gtggactctt    2700
gttccaaact ggaacaacac tcaaccctat ctcggtctat tcttttgatt tataagggat    2760
tttgccgatt tcggcctatt ggttaaaaaa tgagctgatt taacaaaaat ttaacgcgaa    2820
ttttaacaaa atattaacgc ttacaatttc cattcgccat tcaggctgcg caactgttgg    2880
gaagggcgat cggtgcgggc ctcttcgcta ttacgccagc tggcgaaagg gggatgtgct    2940
gcaaggcgat taagttgggt aacgccaggg ttttcccagt cacgacgttg taaaacgacg    3000
gccagtgaat tgtaatacga ctcactatag ggcgaattgg gtaccgggcc cccctcgag    3060 gtcgatggtg tcgataagct tgatatcgaa ttcatgtcac acaaaccgat cttcgcctca    3120
aggaaaccta attctacatc cgagagactg ccgagatcca gtctacactg attaattttc    3180
gggccaataa tttaaaaaaa tcgtgttata taatattata tgtattatat atatacatca    3240
tgatgatact gacagtcatg tcccattgct aaatagacag actccatctg ccgcctccaa    3300
ctgatgttct caatatttaa ggggtcatct cgcattgttt aataataaac agactccatc    3360
taccgcctcc aaatgatgtt ctcaaaatat attgtatgaa cttatttta ttacttagta    3420 ttattagaca acttacttgc tttatgaaaa acacttccta tttaggaaac aatttataat    3480
ggcagttcgt tcatttaaca atttatgtag aataaatgtt ataaatgcgt atgggaaatc    3540
ttaaatatgg atagcataaa tgatatctgc attgcctaat tcgaaatcaa cagcaacgaa    3600
aaaaatccct tgtacaacat aaatagtcat cgagaaatat caactatcaa agaacagcta    3660
ttcacacgtt actattgaga ttattattgg acgagaatca cacactcaac tgtctttctc    3720
tcttctagaa atacaggtac aagtatgtac tattctcatt gttcatactt ctagtcattt    3780
catcccacat attccttgga tttctctcca atgaatgaca ttctatcttg caaattcaac    3840
aattataata agatatacca aagtagcggt atagtggcaa tcaaaaagct tctctggtgt    3900
gcttctcgta tttattttta ttctaatgat ccattaaagg tatatattta tttcttgtta    3960
tataatcctt ttgtttatta catgggctgg atacataaag gtattttgat ttaattttt    4020 gcttaaattc aatccccct cgttcagtgt caactgtaat ggtaggaaat taccatactt    4080
ttgaagaagc aaaaaaatg aaagaaaaaa aaatcgtat ttccaggtta gacgttccgc    4140
agaatctaga atgcggtatg cggtacattg ttcttcgaac gtaaagttg cgctccctga    4200 gatattgtac attttttgctt ttacaagtac aagtacatcg tacaactatg tactactgtt    4260
gatgcatcca caacagtttg ttttgttttt ttttgttttt ttttttttcta atgattcatt    4320 accgctatgt ataccttactt gtacttgtag taagccgggt tattggcgtt caattaatca    4380
```

```
tagacttatg aatctgcacg gtgtgcgctg cgagttactt ttagcttatg catgctactt    4440
gggtgtaata ttgggatctg ttcggaaatc aacggatgct caaccgattt cgacagtaat    4500
taattaagtc atacacaagt cagctttctt cgagcctcat ataagtataa gtagttcaac    4560
gtattagcac tgtacccagc atctccgtat cgagaaacac aacaacatgc cccattggac    4620
agatcatgcg gatacacagg ttgtgcagta tcatacatac tcgatcagac aggtcgtctg    4680
accatcatac aagctgaaca agcgctccat acttgcacgc tctctatata cacagttaaa    4740
ttacatatcc atagtctaac ctctaacagt taatcttctg gtaagcctcc cagccagcct    4800
tctggtatcg cttggcctcc tcaataggat ctcggttctg gccgtacaga cctcggccga    4860
caattatgat atccgttccg gtagacatga catcctcaac agttcggtac tgctgtccga    4920
gagcgtctcc cttgtcgtca agacccaccc cgggggtcag aataagccag tcctcagagt    4980
cgcccttagg tcggttctgg gcaatgaagc caaccacaaa ctcggggtcg gatcgggcaa    5040
gctcaatggt ctgcttggag tactcgccag tggccagaga gcccttgcaa gacagctcgg    5100
ccagcatgag cagacctctg ccagcttct cgttgggaga ggggactagg aactccttgt    5160
actgggagtt ctcgtagtca gagacgtcct ccttcttctg ttcagagaca gtttcctcgg    5220
caccagctcg caggccagca atgattccgg ttccgggtac accgtgggcg ttggtgatat    5280
cggaccactc ggcgattcgg tgacaccggt actggtgctt gacagtgttg ccaatatctg    5340
cgaactttct gtcctcgaac aggaagaaac cgtgcttaag agcaagttcc ttgaggggga    5400
gcacagtgcc ggcgtaggtg aagtcgtcaa tgatgtcgat atgggttttg atcatgcaca    5460
cataaggtcc gaccttatcg gcaagctcaa tgagctcctt ggtggtggta acatccagag    5520
aagcacacag gttggttttc ttggctgcca cgagcttgag cactcgagcg gcaaaggcgg    5580
acttgtggac gttagctcga gcttcgtagg agggcatttt ggtggtgaag aggagactga    5640
aataaattta gtctgcagaa cttttttatcg gaaccttatc tggggcagtg aagtatatgt    5700
tatggtaata gttacgagtt agttgaactt atagatagac tggactatac ggctatcggt    5760
ccaaattaga aagaacgtca atggctctct gggcgtcgcc tttgccgaca aaaatgtgat    5820
catgatgaaa gccagcaatg acgttgcagc tgatattgtt gtcggccaac cgcgccgaaa    5880
acgcagctgt cagacccaca gcctccaacg aagaatgtat cgtcaaagtg atccaagcac    5940
actcatagtt ggagtcgtac tccaaaggcg gcaatgacga gtcagacaga tactcgtcga    6000
cgcagtagga tgtcctgcac gggtcttttt gtggggtgtg gagaaagggg tgcttggaga    6060
tggaagccgg tagaaccggg ctgcttgtgc ttggagatgg aagccggtag aaccgggctg    6120
cttggggga tttggggccg ctgggctcca aagaggggta ggcatttcgt tggggttacg    6180
taattgcggc atttgggtcc tgcgcgcatg tcccattggt cagaattagt ccggatagga    6240
gacttatcag ccaatcacag cgccggatcc acctgtaggt tgggttgggt gggagcaccc    6300
ctccacagag tagagtcaaa cagcagcagc aacatgatag ttgggggtgt gcgtgttaaa    6360
ggaaaaaaaa gaagcttggg ttatattccc gctctattta gaggttgcgg gatagacgcc    6420
gacggagggc aatggcgcca tggaaccttg cggatatcga tacgccgcgg cggactgcgt    6480
ccgaaccagc tccagcagcg ttttttccgg gccattgagc cgactgcgac cccgccaacg    6540
tgtcttggcc cacgcactca tgtcatgttg gtgttgggag gccactttt aagtagcaca    6600
aggcacctag ctcgcagcaa ggtgtccgaa ccaaagaagc ggctgcagtg gtgcaaacgg    6660
ggcggaaacg gcgggaaaaa gccacggggg cacgaattga ggcacgccct cgaatttgag    6720
```

```
acgagtcacg gccccattcg cccgcgcaat ggctcgccaa cgcccggtct tttgcaccac    6780
atcaggttac cccaagccaa acctttgtgt taaaaagctt aacatattat accgaacgta    6840
ggtttgggcg ggcttgctcc gtctgtccaa ggcaacattt atataagggt ctgcatcgcc    6900
ggctcaattg aatctttttt cttcttctct tctctatatt cattcttgaa ttaaacacac    6960
atcaatccgc ggccgcatgg gaacggacca aggaaaaacc ttcacctggg aagagctggc    7020
ggcccataac accaaggacg acctactctt ggccatccgc ggcagggtgt acgatgtcac    7080
aaagttcttg agccgccatc ctggtggagt ggacactctc ctgctcggag ctggccgaga    7140
tgttactccg gtctttgaga tgtatcacgc gtttggggct gcagatgcca ttatgaagaa    7200
gtactatgtc ggtacactgg tctcgaatga gctgcccatc ttcccggagc caacggtgtt    7260
ccacaaaacc atcaagacga gagtcgaggg ctactttacg gatcggaaca ttgatcccaa    7320
gaatagacca gagatctggg gacgatacgc tcttatcttt ggatccttga tcgcttccta    7380
ctacgcgcag ctctttgtgc ctttcgttgt cgaacgcaca tggcttcagg tggtgtttgc    7440
aatcatcatg ggatttgcgt gcgcacaagt cggactcaac cctcttcatg atgcgtctca    7500
cttttcagtg acccacaacc ccactgtctg gaagattctg ggagccacgc acgacttttt    7560
caacggagca tcgtacctgg tgtggatgta ccaacatatg ctcggccatc acccctacac    7620
caacattgct ggagcagatc ccgacgtgtc gacgtctgag cccgatgttc gtcgtatcaa    7680
gcccaaccaa aagtggtttg tcaaccacat caaccagcac atgtttgttc ctttcctgta    7740
cggactgctg gcgttcaagg tgcgcattca ggacatcaac attttgtact ttgtcaagac    7800
caatgacgct attcgtgtca atcccatctc gacatggcac actgtgatgt tctggggcgg    7860
caaggctttc tttgtctggt atcgcctgat tgttcccctg cagtatctgc ccctgggcaa    7920
ggtgctgctc ttgttcacgg tcgcggacat ggtgtcgtct tactggctgg cgctgacctt    7980
ccaggcgaac cacgttgttg aggaagttca gtggccgttg cctgacgaga acgggatcat    8040
ccaaaaggac tgggcagcta tgcaggtcga gactacgcag gattacgcac acgattcgca    8100
cctctggacc agcatcactg gcagcttgaa ctaccaggct gtgcaccatc tgttccccaa    8160
cgtgtcgcag caccattatc ccgatattct ggccatcatc aagaacacct gcagcgagta    8220
caaggttcca taccttgtca aggatacgtt ttggcaagca tttgcttcac atttggagca    8280
cttgcgtgtt cttggactcc gtcccaagga agagtaggc                          8319
```